US010905758B2

(12) United States Patent
Nikolin et al.

(10) Patent No.: US 10,905,758 B2
(45) Date of Patent: Feb. 2, 2021

(54) INTRANASAL VECTOR VACCINE AGAINST PORCINE EPIDEMIC DIARRHEA

(71) Applicant: Boehringer Ingelheim Vetmedica GmbH, Ingelheim am Rhein (DE)

(72) Inventors: Veljko Nikolin, Hannover (DE); Andreas Gallei, Wedemark (DE)

( * ) Notice: Subject to any disclaimer, the term of this patent is extended or adjusted under 35 U.S.C. 154(b) by 0 days.

(21) Appl. No.: 16/575,121

(22) Filed: Sep. 18, 2019

(65) Prior Publication Data

US 2020/0093918 A1 Mar. 26, 2020

(30) Foreign Application Priority Data

Sep. 20, 2018 (EP) ..................................... 18195788
Mar. 28, 2019 (EP) ..................................... 19165985

(51) Int. Cl.
| | | |
|---|---|---|
| *A61K 39/215* | (2006.01) | |
| *C12N 7/00* | (2006.01) | |
| *C12N 15/86* | (2006.01) | |
| *C07K 14/005* | (2006.01) | |
| *A61P 31/14* | (2006.01) | |
| *A61K 39/00* | (2006.01) | |

(52) U.S. Cl.
CPC ............ *A61K 39/215* (2013.01); *A61P 31/14* (2018.01); *C07K 14/005* (2013.01); *C12N 7/00* (2013.01); *C12N 15/86* (2013.01); *A61K 2039/5254* (2013.01); *A61K 2039/543* (2013.01); *A61K 2039/552* (2013.01); *C12N 2760/18434* (2013.01); *C12N 2760/18441* (2013.01); *C12N 2760/18451* (2013.01); *C12N 2770/20022* (2013.01); *C12N 2770/20034* (2013.01)

(58) Field of Classification Search
None
See application file for complete search history.

(56) References Cited

U.S. PATENT DOCUMENTS

| 2005/0089985 | A1 | 4/2005 | Parks et al. | |
|---|---|---|---|---|
| 2015/0328307 | A1* | 11/2015 | Lawrence | C12N 7/00 424/186.1 |
| 2020/0093918 | A1* | 3/2020 | Nikolin | C12N 15/86 |

FOREIGN PATENT DOCUMENTS

| CN | 107619819 A | 1/2018 |
|---|---|---|
| WO | 2017/165366 A1 | 9/2017 |

OTHER PUBLICATIONS

Zhang et al. (Virology. 2013; 446: 25-36).*
Arriba et al. (Veterinary Immunology and Immunopathology. 2002; 84: 1-16).*
Sequence alignment of SEQ ID 1 with Geneseq db BCK95766 by Balasch et al in WO2016007576 Jan. 2016.*
Sequence alignment of SEQ ID 2 with Geneseq db BCF33567 by Hernandez et al in US2015283229 Oct. 2015.*
Sequence alignment of SEQ ID 16 with Geneseq db BCF33567 by Hernandez et al in US2015283229 Oct. 2015.*
Sequence alignment of SEQ ID 17 with Geneseq db BCF33567 by Hernandez et al in US2015283229 Oct. 2015.*
Sequence alignment of SEQ 2 with 14716481 PEDV spike May 2015.*
Sequence alignment of SEQ 16 with 14716481 PEDV spike May 2015.*
Hammond Jef M. et al., "Porcine adenovirus as a delivery system for swine vaccines and immunotherapeutics", The Veterinary Journal, Jan. 1, 2005, vol. 169, No. 1, pp. 17-27, XP004728936.
International Search Report for PCT/EP2019/075015, dated Dec. 10, 2019.
Joshi et al., "Passive immunity to porcine epidemic diarrhea virus following immunization of pregnant gilts with a recombinant ORF virus vector expressing the spike protein", Archives of Virology, 2018, vol. 163(9), pp. 2327-2335.

* cited by examiner

*Primary Examiner* — Shanon A. Foley
(74) *Attorney, Agent, or Firm* — Suzanne Seavello Shope; John Ezcurra

(57) ABSTRACT

The present invention relates to the field of (vector) vaccines, and especially to a canine distemper virus (CDV) vector comprising a heterologous nucleotide sequence which encodes a porcine epidemic diarrhea virus (PEDV) antigen. Said PEDV antigen is preferably a PEDV spike (S) protein. The viral vector of the present invention is useful for producing an immunogenic composition or vaccine for intranasally immunizing sows, and thereby protecting piglets, suckled by said sows, against the clinical signs associated with a PEDV infection.

20 Claims, No Drawings
Specification includes a Sequence Listing.

INTRANASAL VECTOR VACCINE AGAINST PORCINE EPIDEMIC DIARRHEA

BACKGROUND OF THE INVENTION

A. Field of the Invention

The present invention relates to the field of (vector) vaccines. The viral vectors of the present invention are useful for producing an immunogenic composition or vaccine for inducing an immune response against porcine epidemic diarrhea virus (PEDV) in a pig.

B. Background and Description of the Related Art

The porcine epidemic diarrhea virus is an enveloped, positive-sense single-stranded RNA virus that causes acute diarrhea, vomiting, and dehydration in pigs. In pigs three weeks of age and younger, clinical signs (including acute watery, diarrhea, vomiting, and dehydration) can be seen as soon as 24 hours after PEDV infection leading up to 100% mortality. Further, the gross and histological changes in the gut of animals infected with PEDV can cause gross pathological lesions in the small intestine.

Although only one serotype of PEDV has been reported, phylogenetic studies of the S gene show that PEDV can be genetically separated into 2 groups: genogroup 1 (G1; classical) and genogroup 2 (G2; field epidemic or pandemic). Each of the genogroups can be further divided into subgroups (1a and 1b; 2a and 2b). G1a includes the prototype PEDV strain CV777, vaccine strains, and other cell culture-adapted strains, whereas G1b comprises new variants that were first identified in China and later in the United States, South Korea and Europe. G2 comprises global field isolates, which are further clustered into 2a and 2b subgroups (G2a and G2b) responsible for previous local epidemic outbreaks in Asia and recent pandemic outbreaks in North America and Asia, respectively.

PEDV is a member of the subfamily Coronavirinae of genus *Alphacoronavirus*. PEDV is an enveloped virus possessing approximately a 28 kb, positive-sense, single stranded RNA genome, with a 5' cap and a 3' polyadenylated tail (Pensaert and De Bouck P. 1978). The genome comprises a 5' untranslated region (UTR), a 3' UTR, and at least seven open reading frames (ORFs) that encode four structural proteins (spike (S), envelope (E), membrane (M), and nucleocapsid (N)) and three non-structural proteins (replicases 1a and 1b and ORF3); these are arranged on the genome in the order 5'-replicase(1a/1b)-S-ORF3-E-M-N-3' (Oldham J. 1972; and Bridgen et al. 1993).

The PEDV S protein is a type I glycoprotein, wherein the S protein (of G2b PEDV) is composed of 1,383 amino acids (aa). The S protein can be divided into S1 (e.g., 1-789 aa) and S2 (e.g., 790-1,383 aa) domains based on its homology with S protein of other coronaviruses. The S protein in coronaviruses is a surface antigen, where it plays a role in regulating interactions with host cell receptor glycoproteins to mediate viral entry, and stimulating induction of neutralizing antibodies in the natural host. Thus, the S glycoprotein is a primary target for the development of effective vaccines against PEDV.

PEDV was first identified in Europe but has become increasingly problematic in many Asian countries, including Korea, China, Japan, the Philippines, and Thailand. Since 2013, PEDV emerged in the U.S. and the economic impact of PEDV infection has already been substantial. Accordingly, there is a continuing need to develop vaccines capable of protecting pigs against disease associated with PEDV.

WO2017165366 (A1) describes that an orf virus (ORFV) vector expressing the PEDV S protein induces serum IgG, IgA and neutralizing antibody responses in pigs, when administered intramuscularly (paragraph [0172] of WO2017165366 (A1)). Also, it was shown that the intramuscular administration of this vector to pregnant gilts resulted in passive immunization of piglets born to said gilts (Joshi et al. Arch Virol. 163(9):2327-2335 (2018).

However, as the repeated intramuscular injection using conventional needle and syringe may induce stress to the animals, a vector vaccine against porcine epidemic diarrhea (PED) is desired which may be administered, e.g. as a nasal spray, via the intranasal route.

SUMMARY OF THE INVENTION

The solution to the above technical problem(s) is achieved by the description and the embodiments characterized in the claims.

Thus, the invention in its different aspects is implemented according to the claims.

The invention is based on the surprising finding that the insertion of a heterologous nucleotide sequence encoding a porcine epidemic diarrhea virus (PEDV) spike (S) protein, between the phosphoprotein (P) gene and the matrix protein (M) gene of a canine distemper virus (CDV) virus genome, results in a CDV vector useful for intranasally immunizing sows, and thereby protecting piglets, suckled by said sows, against clinical signs associated with a PEDV infection.

In a first aspect, the invention thus provides a canine distemper virus (CDV) vector comprising a heterologous nucleotide sequence of interest, wherein said heterologous nucleotide sequence of interest encodes a porcine epidemic diarrhea virus (PEDV) antigen.

In a specific aspect, the present invention uses the Lederle vaccine strain of CDV (deposited at the ATCC under the accession number VR-128) as a backbone (genotype represented by GenBank Accession DQ903854.1, AY288311 or AY286480) or an at least 70%, 80%, 85%, 90%, 91%, 92%, 93%, 94%, 95%, 96%, 97%, 98%, 99% identical sequence thereof, such as from virus derived by additional passages thereof (e.g. Canine Distemper Virus, Lederle Avirulent, Catalog No. NR-3845, Biodefense and Emerging Infections Research Resources Repository, P.O. Box 4137, Manassas, Va. 20108-4137, USA).

The vector according to the invention is in particular useful for the vaccination of mammals, in particular of swine.

Furthermore, the present invention contemplates vectors for inducing an immune response against porcine epidemic diarrhea virus in pigs. Thus, in the context of the present invention also CDV vectors are provided comprising an expression cassette with a heterologous RNA sequence, which encodes a Spike protein of porcine epidemic diarrhea virus.

The present invention further concerns mammalian host cells comprising such vectors and methods of generating vector vaccines using such host cells, as well as immunogenic compositions and vaccines comprising the CDV vector of the present invention.

DETAILED DESCRIPTION OF THE INVENTION

The present invention solves the problems inherent in the prior art and provides a distinct advance in the state of the art.

In the context of the present invention, a CDV vector encoding Spike protein of porcine epidemic diarrhea virus (PEDV) was intranasally administered to pregnant sows, which then resulted, through antibody positive colostrum intake, in passive immunization of piglets seen by a reduced incidence or severity of the clinical signs, letality and virus shedding after a challenge with PEDV.

The invention thus provides a canine distemper virus vector, also termed "CDV vector of the present invention" herein, wherein said vector comprises a heterologous nucleotide sequence of interest, and wherein said heterologous nucleotide sequence of interest encodes a porcine epidemic diarrhea virus (PEDV) antigen.

The heterologous nucleotide sequence of interest, as mentioned herein, is in particular a heterologous RNA sequence of interest.

Preferably, said PEDV antigen is selected from the group consisting of PEDV spike (S) protein and PEDV nucleoprotein (N protein), wherein a PEDV spike protein is particularly preferred.

Preferably, said PEDV antigen is thus a PEDV S protein, and wherein said PEDV S protein preferably comprises or consists of an amino acid sequence being at least 70%, 80%, 85%, 90%, 91%, 92%, 93%, 94%, 95%, 96%, 97%, 98%, or 99% identical with the sequence of SEQ ID NO: 1 or SEQ ID NO:2.

In one preferred aspect, said PEDV S protein thus comprises or consists of an amino acid sequence being at least 70%, 80%, 85%, 90%, 91%, 92%, 93%, 94%, 95%, 96%, 97%, 98%, or 99% identical with the sequence of SEQ ID NO: 1.

In another preferred aspect, said PEDV S protein thus comprises or consists of an amino acid sequence being at least 70%, 80%, 85%, 90%, 91%, 92%, 93%, 94%, 95%, 96%, 97%, 98%, or 99% identical with the sequence of SEQ ID NO:2.

As another preferred option, said PEDV antigen is a PEDV S protein, and wherein said PEDV S protein preferably comprises or consists of an amino acid sequence being at least 70%, 80%, 85%, 90%, 91%, 92%, 93%, 94%, 95%, 96%, 97%, 98%, or 99% identical with the sequence of SEQ ID NO:16 or SEQ ID NO:17.

In one preferred aspect, said PEDV S protein thus comprises or consists of an amino acid sequence being at least 70%, 80%, 85%, 90%, 91%, 92%, 93%, 94%, 95%, 96%, 97%, 98%, or 99% identical with the sequence of SEQ ID NO:16.

In another preferred aspect, said PEDV S protein thus comprises or consists of an amino acid sequence being at least 70%, 80%, 85%, 90%, 91%, 92%, 93%, 94%, 95%, 96%, 97%, 98%, or 99% identical with the sequence of SEQ ID NO:17.

According to another preferred aspect, the heterologous nucleotide sequence of interest encodes a PEDV S protein, wherein said heterologous nucleotide sequence of interest consists of or comprises an RNA sequence being at least 70%, 80%, 85%, 90%, 91%, 92%, 93%, 94%, 95%, 96%, 97%, 98%, or 99% identical with the sequence of any one of SEQ ID NOs:3 to 5.

Thus, in one preferred aspect, said heterologous nucleotide sequence of interest consists of or comprises an RNA sequence being at least 70%, 80%, 85%, 90%, 91%, 92%, 93%, 94%, 95%, 96%, 97%, 98%, or 99% identical with the sequence of SEQ ID NO:3.

In another preferred aspect, said heterologous nucleotide sequence of interest thus consists of or comprises an RNA sequence being at least 70%, 80%, 85%, 90%, 91%, 92%, 93%, 94%, 95%, 96%, 97%, 98%, or 99% identical with the sequence of SEQ ID NO:4.

In a further preferred aspect, said heterologous nucleotide sequence of interest thus consists of or comprises an RNA sequence being at least 70%, 80%, 85%, 90%, 91%, 92%, 93%, 94%, 95%, 96%, 97%, 98%, or 99% identical with the sequence of SEQ ID NO:5.

In particular it is preferred that the length of the RNA sequence of interest adheres to the "rule of six", meaning that the number of nucleotides of the RNA sequence of interest represents a multiple of six. Thus, as the case may be, it is preferred to elongate a given nucleotide sequence encoding the PEDV antigen by an additional triplet, in particular coding for a stop codon, such that the number of the nucleotides of the resulting nucleotide sequence of interest is divisible by six.

According to a particular preferred aspect of the present invention the heterologous RNA sequence of interest is preferably located between a P gene and an M gene of a CDV, and/or preferably the heterologous RNA sequence of interest is operably linked to a gene start (GS) sequence located in 3' direction of said heterologous RNA sequence, wherein said GS sequence is most preferably included in an exogenous 3' non-coding region of an H gene of a CDV, and/or to the genome promoter of a CDV.

Thus, in one preferred aspect said heterologous RNA sequence of interest is located between a P gene and an M gene of a CDV and is operably linked to a gene start (GS) sequence located in 3' direction of said heterologous RNA sequence, and wherein said GS sequence is included in an exogenous 3' non-coding region of an H gene of a CDV, and/or the genome promoter of a CDV.

In another preferred aspect, said heterologous RNA sequence of interest is operably linked to a gene start (GS) sequence located in 3' direction of said heterologous RNA sequence and/or to the genome promoter of a CDV.

Said GS sequence is preferably included in an exogenous 3' non-coding region of an H gene of a CDV.

Particularly, the heterologous RNA sequence of interest in the CDV vector is operably linked to an exogenous 3' non-coding region of an H gene of a CDV, in particular to the GS sequence included therein, wherein said exogenous 3' non-coding region of an H gene of a CDV flanks the 3' end of said heterologous RNA sequence of interest encoding a PEDV S protein, and the genome promoter of a CDV.

Preferably, the CDV vector of the present invention comprises an RNA sequence being at least 70%, 80%, 85%, 90%, 91%, 92%, 93%, 94%, 95%, 96%, 97%, 98%, or 99% identical with the sequence of SEQ ID NO:6 or SEQ ID NO:7. Thus, the CDV vector of the present invention preferably comprises a heterologous nucleotide sequence of interest, wherein said heterologous nucleotide sequence of interest is an RNA sequence being at least 70%, 80%, 85%, 90%, 91%, 92%, 93%, 94%, 95%, 96%, 97%, 98%, or 99% identical with the sequence of SEQ ID NO:6 or SEQ ID NO:7.

Thus, according to one preferred aspect, the CDV vector of the present invention comprises an RNA sequence being at least 70%, 80%, 85%, 90%, 91%, 92%, 93%, 94%, 95%, 96%, 97%, 98%, or 99% identical with the sequence of SEQ ID NO:6. Hence, according to one preferred aspect, the CDV vector of the present invention comprises a heterologous nucleotide sequence of interest, wherein said heterologous nucleotide sequence of interest is an RNA sequence being at least 70%, 80%, 85%, 90%, 91%, 92%, 93%, 94%, 95%, 96%, 97%, 98%, or 99% identical with the sequence of SEQ ID NO:6.

According to another preferred aspect, the CDV vector of the present invention thus comprises an RNA sequence being at least 70%, 80%, 85%, 90%, 91%, 92%, 93%, 94%, 95%, 96%, 97%, 98%, or 99% identical with the sequence of SEQ ID NO:7. Hence, according to another preferred aspect, the CDV vector of the present invention comprises a heterologous nucleotide sequence of interest, wherein said heterologous nucleotide sequence of interest is an RNA sequence being at least 70%, 80%, 85%, 90%, 91%, 92%, 93%, 94%, 95%, 96%, 97%, 98%, or 99% identical with the sequence of SEQ ID NO:7.

In particular, the CDV vector of the present invention comprises an RNA sequence being at least 70%, 80%, 85%, 90%, 91%, 92%, 93%, 94%, 95%, 96%, 97%, 98%, or 99% identical with the sequence of SEQ ID NO:8. Thus, the CDV vector of the present invention in particular comprises a heterologous nucleotide sequence of interest, wherein said heterologous nucleotide sequence of interest is an RNA sequence being at least 70%, 80%, 85%, 90%, 91%, 92%, 93%, 94%, 95%, 96%, 97%, 98%, or 99% identical with the sequence of SEQ ID NO:8.

The CDV vector of the present invention preferably further comprises an RNA sequence being at least 70%, 80%, 85%, 90%, 91%, 92%, 93%, 94%, 95%, 96%, 97%, 98%, or 99% identical with the sequence of SEQ ID NO:9, and wherein this RNA sequence flanks the 5'end of the RNA sequence being at least 70%, 80%, 85%, 90%, 91%, 92%, 93%, 94%, 95%, 96%, 97%, 98%, or 99% identical with the sequence of SEQ ID NO:8.

The CDV vector of the present invention preferably further comprises an RNA sequence being at least 70%, 80%, 85%, 90%, 91%, 92%, 93%, 94%, 95%, 96%, 97%, 98%, or 99% identical with the sequence of SEQ ID NO:10, and wherein this RNA sequence flanks the 3'end of the RNA sequence being at least 70%, 80%, 85%, 90%, 91%, 92%, 93%, 94%, 95%, 96%, 97%, 98%, or 99% identical with the sequence of SEQ ID NO:8.

Most preferably, the CDV vector of the present invention comprises or consists of
- a first RNA sequence being at least 70%, 80%, 85%, 90%, 91%, 92%, 93%, 94%, 95%, 96%, 97%, 98%, or 99% identical with the sequence of SEQ ID NO:8, and
- a second RNA sequence being at least 70%, 80%, 85%, 90%, 91%, 92%, 93%, 94%, 95%, 96%, 97%, 98%, or 99% identical with the sequence of SEQ ID NO:9, and wherein said second RNA sequence flanks the 5'end of said first RNA sequence, and
- a third RNA sequence being at least 70%, 80%, 85%, 90%, 91%, 92%, 93%, 94%, 95%, 96%, 97%, 98%, or 99% identical with the sequence of SEQ ID NO:10, and wherein said third RNA sequence flanks the 3' end of said first RNA sequence.

The invention further provides a nucleic acid molecule, which encodes the CDV vector of the present invention, wherein said nucleic acid molecule is preferably a DNA molecule, and wherein said DNA molecule is also termed the "DNA molecule of the present invention" hereinafter.

In particular, said nucleic acid molecule is an isolated nucleic acid molecule.

Preferably, said nucleic acid molecule comprises a DNA sequence encoding a PEDV spike (S) protein, and wherein said sequence is preferably a DNA sequence being at least 70%, 80%, 85%, 90%, 91%, 92%, 93%, 94%, 95%, 96%, 97%, 98%, or 99% identical with the sequence of SEQ ID NO:11 or SEQ ID NO:12.

In one preferred aspect, said nucleic acid molecule thus comprises a DNA sequence being at least 70%, 80%, 85%, 90%, 91%, 92%, 93%, 94%, 95%, 96%, 97%, 98%, or 99% identical with the sequence of SEQ ID NO:11.

In another preferred aspect, said nucleic acid molecule thus comprises a DNA sequence being at least 70%, 80%, 85%, 90%, 91%, 92%, 93%, 94%, 95%, 96%, 97%, 98%, or 99% identical with the sequence of SEQ ID NO:12.

Further, the present invention provides a DNA molecule, in particular the DNA molecule of the present invention, wherein said molecule comprises a DNA sequence being at least 70%, 80%, 85%, 90%, 91%, 92%, 93%, 94%, 95%, 96%, 97%, 98%, or 99% identical with the sequence of SEQ ID NO: 13.

In particular, said molecule comprises a DNA sequence being at least 70%, 80%, 85%, 90%, 91%, 92%, 93%, 94%, 95%, 96%, 97%, 98%, or 99% identical with the sequence of SEQ ID NO: 14.

The invention further provides a mammalian host cell containing
- the CDV vector of the present invention, or
- the DNA molecule of the present invention, and wherein said mammalian host cell is preferably an isolated mammalian host cell.

The present invention also provides
- the CDV vector of the present invention, or
- the DNA molecule of the present invention for use as a medicament, preferably as a vaccine.

Additionally, in the context of the invention, a DNA construct is provided comprising the DNA molecule of the present invention, wherein said DNA construct is in particular a DNA vector such as a plasmid. DNA vectors or plasmids into which the DNA molecule of the present invention can be inserted will be recognized by those of ordinary skill in the art. The DNA construct, as described herein, is preferably an isolated DNA construct. As used herein, the term "comprising the DNA molecule" is in particular understood to be equivalent to the term "comprising the sequence of the DNA molecule".

Further, the present invention provides an RNA transcript of the DNA construct described herein, wherein said RNA transcript is preferably an isolated RNA transcript.

The present invention also provides a cell transfected with the DNA construct described herein, wherein said cell is preferably an isolated cell.

Further, the present invention provides a cell transfected with the RNA transcript mentioned herein, wherein said cell is preferably an isolated cell.

Preferably, the cell is from an eukaryotic cell line.

In a specific aspect, in particular of the method according to the present invention, the cell is a Vero cell, ST cell or BHK-21 cell, Ma104 cell, MDBK cell, RK13 cell, MDCK cell or PK15 cell.

All mentioned cell lines are well known to the person skilled in the art and are public available. Vero cells are exemplarily deposited at the American Tissue Culture Collection under accession number ATCC CCL-81. ST cells are exemplarily deposited at the American Tissue Culture Collection under accession number CRL-1746. BHK-21 cells are exemplarily deposited at the American Tissue Culture Collection under accession number ATCC CCL-10. MDCK cells are exemplarily deposited at the American Tissue Culture Collection under accession number ATCC CCL-34 or ATCC CRL-2285.

Most preferably, the cell or mammalian host cell, respectively, is a Vero cell.

Furthermore, in the context of the present invention, a method for the preparation of an infectious CDV containing a heterologous gene, in particular for preparing the CDV vector of the present invention is provided, wherein said method comprises the steps of:

a. providing a host cell expressing a heterologous RNA polymerase;
b. transfecting the host cell with the DNA construct described herein, and wherein the DNA molecule of the present invention included in the DNA construct is transcribed by the heterologous RNA polymerase, and
c. isolating the viruses produced by the cells.

Preferably, the CDV vector of the present invention is grown in Vero cells.

Thus, the host cell, as mentioned herein, is preferably a Vero cell.

Since CDV has a negative stranded RNA genome, the presence of an RNA polymerase, preferably of T7 RNA polymerase or the RNA polymerase encoded by the CDV, in the transfected cells is required. Most preferred is the use of the T7 RNA polymerase. The presence of the RNA polymerase in the transfected cells can be provided, for instance, by co-transfection of a plasmid coding for and expressing the RNA polymerase or by penetrating the cells with RNA polymerase protein. According to the invention, in this regard, the use of transgenic cells producing RNA polymerase is particularly preferred, such as the transfection of the DNA construct into BHK-21 cells expressing T7 polymerase or into BSR-T7/5 cells. Alternatively, the cells can also be transfected with the mRNA that codes for the RNA polymerase and which is translated into the RNA polymerase when transfected into the host cells.

According to another aspect, the invention further provides the use of the CDV vector of the invention or of the cell described herein for the manufacture of an immunogenic composition or a vaccine.

In still another aspect, the present invention also provides an immunogenic composition, which is also termed "the immunogenic composition of the present invention" herein, wherein said immunogenic composition comprises
a. the CDV vector of the present invention, wherein said vector is optionally an infectious and/or attenuated virus or wherein said vector is optionally an attenuated and/or modified live virus, and
b. a recombinant protein expressed by said vector and/or a quarternary structure comprising a plurality of a recombinant protein expressed by said vector, and
c. optionally a pharmaceutical- or veterinary-acceptable carrier or excipient, wherein preferably said carrier is suitable for intranasal application.

It is in particular understood that the phrase "expressed by said vector" or "expressed by the vector", respectively, as used herein, is in particular equivalent to "expressed in a cell infected with the vector" or "expressed in a cell infected with said vector", respectively.

A "quaternary structure comprising a plurality of a recombinant protein", for purposes of the present invention, refers to a three-dimensional arrangement of a plurality of said recombinant protein, such as a trimeric structure composed of three PEDV S proteins associated along a coiled coil sequence included in the amino acid sequence of said protein(s).

Preferably, said recombinant protein expressed by the vector is
a PEDV S protein, or
a PEDV N protein.

In particular, said recombinant protein expressed by said vector is a PEDV S protein, in particular comprising or consisting of an amino acid sequence being at least 70%, 80%, 85%, 90%, 91%, 92%, 93%, 94%, 95%, 96%, 97%, 98%, or 99% identical with the sequence of SEQ ID NO:1 or SEQ ID NO:2.

As another preferred option, said recombinant protein expressed by said vector is a PEDV S protein, in particular comprising or consisting of an amino acid sequence being at least 70%, 80%, 85%, 90%, 91%, 92%, 93%, 94%, 95%, 96%, 97%, 98%, or 99% identical with the sequence of SEQ ID NO:16 or SEQ ID NO:17.

According to another preferred aspect, the immunogenic composition of the present invention comprises or consists of
a. the CDV vector of the present invention, and
b. a polypeptide comprising or consisting of an amino acid sequence being at least 70%, 80%, 85%, 90%, 91%, 92%, 93%, 94%, 95%, 96%, 97%, 98%, or 99% identical with the sequence of SEQ ID NO:1 or SEQ ID NO:2, wherein said polypeptide is preferably a recombinant protein expressed by said vector,
c. and optionally a pharmaceutical- or veterinary-acceptable carrier or excipient, wherein said carrier is preferably suitable for intranasal application.

Preferably, said CDV vector comprises a heterologous nucleotide sequence of interest encoding said polypeptide being at least 70%, 80%, 85%, 90%, 91%, 92%, 93%, 94%, 95%, 96%, 97%, 98%, or 99% identical with the sequence of SEQ ID NO:1 or SEQ ID NO:2.

According to another preferred option, the immunogenic composition of the present invention comprises or consists of
a. the CDV vector of the present invention, and
b. a polypeptide comprising or consisting of an amino acid sequence being at least 70%, 80%, 85%, 90%, 91%, 92%, 93%, 94%, 95%, 96%, 97%, 98%, or 99% identical with the sequence of SEQ ID NO:16 or SEQ ID NO:17, wherein said polypeptide is preferably a recombinant protein expressed by said vector,
c. and optionally a pharmaceutical- or veterinary-acceptable carrier or excipient, wherein said carrier is preferably suitable for intranasal application.

Preferably, said CDV vector comprises a heterologous nucleotide sequence of interest encoding said polypeptide being at least 70%, 80%, 85%, 90%, 91%, 92%, 93%, 94%, 95%, 96%, 97%, 98%, or 99% identical with the sequence of SEQ ID NO:16 or SEQ ID NO:17.

The invention also provides a vaccine or pharmaceutical composition, which is hereinafter also termed "the vaccine or the pharmaceutical composition of the present invention, wherein said vaccine or pharmaceutical composition comprises
a. the CDV vector of the present invention, and
b. a recombinant protein expressed by said vector and/or a quarternary structure comprising a plurality of a recombinant protein expressed by said vector, and
c. a pharmaceutical- or veterinary-acceptable carrier or excipient, wherein said carrier is preferably suitable for oral, intradermal, intramuscular or intranasal application, and
d. optionally said vaccine further comprises an adjuvant, and wherein said recombinant protein expressed by the vector is preferably a PEDV S protein or a PEDV N protein.

Preferably, said recombinant protein expressed by said vector, which is included in the vaccine or pharmaceutical composition of the present invention, is a PEDV S protein, and wherein said PEDV S protein in particular comprises or consists of an amino acid sequence being at least 70%, 80%, 85%, 90%, 91%, 92%, 93%, 94%, 95%, 96%, 97%, 98%, or 99% identical with the sequence of SEQ ID NO:1 or SEQ ID NO:2.

As another preferred option, said recombinant protein expressed by said vector, which is included in the vaccine or pharmaceutical composition of the present invention, is a PEDV S protein, and wherein said PEDV S protein in particular comprises or consists of an amino acid sequence being at least 70%, 80%, 85%, 90%, 91%, 92%, 93%, 94%, 95%, 96%, 97%, 98%, or 99% identical with the sequence of SEQ ID NO:16 or SEQ ID NO:17.

The present invention further provides a method for the preparation of an immunogenic composition or a vaccine for reducing the incidence or the severity of one or more clinical signs associated with or caused by an infection, comprising the following steps:
a. infecting a mammalian host cell, in particular a Vero cell, with the vector of the present invention,
b. cultivating the infected cells under suitable conditions,
c. collecting infected cell cultures,
d. optionally purifying the collected infected cell cultures of step c),
e. optionally mixing said collected infected cell culture with a pharmaceutically acceptable carrier,
and wherein the immunogenic composition or vaccine is preferably reducing the severity of one or more clinical signs associated with or caused by an infection with a Porcine epidemic diarrhea virus (PEDV). Further, the present invention provides a method of immunizing a subject comprising administering to such subject an immunogenic composition of the present invention.

Advantageously, the immunogenic composition of the present invention has been proven to be safe and efficacious.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular PEDV infection in a herd or in the reduction in the severity of clinical signs caused by or associated with the particular PEDV infection.

Further, the immunization of a subject in need with the immunogenic compositions as provided herewith, results in preventing infection of a subject by PEDV infection. Even more preferably, immunization results in an effective, long-lasting, immunological response against PEDV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects in a herd are effectively immunized.

Preferably, a herd of subjects is envisaged in this context which normally, i.e. without immunization, would develop clinical signs normally caused by or associated with a PEDV infection. Whether the subjects of a herd are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given herd are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular PEDV.

Further, the present invention provides a method of treating and/or preventing clinical signs caused by PEDV infection in a subject of need, the method comprising administering to the subject a therapeutically effective amount of an immunogenic composition of the present invention.

Advantageously, the immunogenic composition of the present invention has been proven to reduce the clinical signs caused by PEDV infection.

The term "treating and/or preventing" in particular refers to the lessening of the incidence of the particular PEDV infection in a herd or the reduction in the severity of clinical signs caused by or associated with the particular PEDV infection. Thus, the term "treating and/or preventing" also refers to the reduction of the number of subjects in a herd that become infected with the particular PEDV (=lessening of the incidence of the particular PEDV infection) or to the reduction of the severity of clinical signs normally associated with or caused by a PEDV infection or the reduction of virus shedding after infection with the particular PEDV or preventing or reducing diarrhea after infection with the particular PEDV in a group of subjects which subjects have received an effective amount of the immunogenic composition as provided herein in comparison to a group of subjects which subjects have not received such immunogenic composition.

The "treating and/or preventing" generally involves the administration of an effective amount of the immunogenic composition of the present invention to a subject or herd of subjects in need of or that could benefit from such a treatment/prophylaxis. The term "treating" refers to the administration of the effective amount of the immunogenic composition once the subject or at least some subjects of the herd is/are already infected with such PEDV and wherein such subjects already show some clinical signs caused by or associated with such PEDV infection. The term "preventing" refers to the administration of a subject prior to any infection of such subject with PEDV or at least where such subject or none of the subjects in a group of subjects do not show any clinical signs caused by or associated with the infection by such PEDV. The terms "prophylaxis" and "preventing" are used interchangeable in this application Preferably, clinical signs are reduced in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular PEDV.

The term "clinical signs" as used herein in particular refers to signs of infection of a subject from PEDV. Examples for such clinical signs include but are not limited to virus load, diarrhea, shedding, increased body temperature, mortality, gross pathological lesions in the intestine, depression, weight loss, reduced growth rates and reduced appetite. However, the clinical signs also include but are not limited to clinical signs that are directly observable from a live animal. Examples for clinical signs that are directly observable from a live animal include weight loss, reduced growth rates, reduced appetite, dehydration, watery diarrhea, vomiting, lameness, lethargy, wasting and unthriftiness and the like.

Preferably, the clinical signs are reduced in incidence or severity in a treated subject compared to subjects that are either not treated or treated with an immunogenic composition that was available prior to the present invention but subsequently infected by the particular PEDV refer to a reduction in weight loss, a lower virus load, a reduction of diarrhea, a reduced shedding, a reduced rectal temperature, reduced mortality, reduced gross pathological lesions in the intestine, or combinations thereof.

Further, the present invention provides a method of reducing the diarrhea in a subject in comparison to a subject of a non-immunized control group of the same species, the method comprising administering to the subject a therapeutically effective amount of an immunogenic composition of the present invention.

Further, the present invention provides a method of reducing the mortality in a subject in comparison to a subject of a non-immunized control group of the same species, the method comprising administering to the subject a therapeutically effective amount of an immunogenic composition of the present invention.

The term "reducing the mortality" means that the mortality is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected by the particular PEDV.

Thus, it has to be understood that a subject can be vaccinated with the immunogenic composition according to the present invention for reducing or preventing clinical signs such as diarrhea or mortality in said subject. Preferably, said subject is a piglet, pig or sow.

Further, the present invention provides a method for inducing the production of antibodies specific for PEDV in a subject, wherein said method comprises administering the immunogenic composition of the present invention to said subject. Preferably, said subject is a piglet, pig or sow.

Further, the present invention provides a method for inducing the production of antibodies specific for PEDV in a sow, wherein said method comprises administering the immunogenic composition of the present invention to said sow.

The term "antibodies specific for PEDV" refers to detectable anti-PEDV antibodies. Further, the anti-PEDV antibodies in the sow have been developed in response to the vaccination with the PEDV vaccine according to the present invention. The term "antibodies specific for PEDV" shall further mean, but is not limited to, a sow that has a detectable anti-PEDV antibody titer, preferably of at least 1:10, more preferably of more than 1:20, even more preferably of more than 1:40, even more preferably of more than 1:80, even more preferably of 1:160, even more preferably of more than 1:320, and most preferably of more than 1:640. Preferably, that anti-PEDV antibody titer is detectable and quantifiable in a specific anti-PEDV immune assay.

Advantageously, the immunogenic composition of the present invention has been shown to induce the production of antibodies specific for PEDV in a sow.

It is well known by the person skilled in the art how to detect the production of antibodies specific for PEDV such as by an ELISA Assay (ELISA's are commercially available).

Further, the present invention provides a method of reducing the diarrhea in a piglet in comparison to a piglet of a non-immunized control group, the method comprising administering to the sow of the piglet a therapeutically effective amount of an immunogenic composition of the present invention, wherein the piglet is to be suckled by said sow. The term "sow of the piglet", as used herein, is in particular understood to be equivalent to "mother sow of the piglet" or "nurse sow of the piglet", respectively.

Further, the present invention provides a method of reducing the mortality in a piglet in comparison to a piglet of a non-immunized control group, the method comprising administering to the sow of the piglet a therapeutically effective amount of an immunogenic composition of the present invention, wherein the piglet is to be suckled by said sow.

Further, the present invention provides a method of reducing the mortality in a piglet in comparison to a piglet of a non-immunized control group, the method comprising administering to the sow of the piglet a therapeutically effective amount of an immunogenic composition of the present invention, wherein the piglet is to be suckled by said sow.

Further, the present invention provides a method of reducing or preventing the clinical signs or disease caused by an infection with a PEDV in a piglet, wherein the piglet is to be suckled by a sow to which the immunogenic composition of the present invention has been administered.

Preferably, the clinical sign that is reduced is mortality. Thus, the present invention also provides a method of reducing the mortality caused by an infection with a PEDV in a piglet, wherein the piglet is to be suckled by a sow to which the immunogenic composition of the present invention has been administered.

Further, the present invention provides a method of reducing or preventing the clinical signs or disease caused by an infection with a PEDV in a piglet, wherein said method comprises
administering the immunogenic composition of the present invention to a sow, and
allowing said piglet to be suckled by said sow.

Advantageously, the immunogenic composition of the present invention has been shown to reduce clinical signs in pigs when administered to sows during pregnancy.

In case piglets are vaccinated with the immunogenic composition of the present invention it has to be understood that time is needed for actual antibody production in said piglet. Therefore, in another aspect of the method present invention the sow being pregnant is vaccinated with the immunogenic composition of the present invention. Said vaccination results in the production of antibodies specific for PEDV in said sow. The maternally derived antibodies from said sow are then passively transferred to the newborn piglets via colostrum and/or milk.

In another specific aspect of the method according to the present invention said sow to which the immunogenic composition is administered is a sow being pregnant, in particular with said piglet. However, it is to be understood that the piglet can be suckled by any sow giving colostrum or milk, wherein said sow is in particular a sow to which said immunogenic has been administered.

In another specific aspect of the method according to the present invention said method comprises the steps of
administering the immunogenic composition of the present invention to a sow being pregnant with said piglet,
allowing said sow to give birth to said piglet, and
allowing said piglet to be suckled by said sow.

In another specific aspect of the method according to the present invention said method results in an improvement in a clinical sign or efficacy parameter selected from the group consisting of: a reduction in weight loss, a lower virus load, a reduction of diarrhea, a reduced shedding, a reduced rectal temperature, reduced mortality, reduced gross pathological lesions in the intestine, or combinations thereof, in comparison to a subject of a non-immunized control group of the same species.

In another specific aspect of the method according to the present invention said subject is a piglet, pig or sow.

Preferably, the immunogenic composition is administered to the subject within the first two month of age, more preferably, within the first month of age.

In another specific aspect of the method according to the present invention the immunogenic composition is administered to the subject within the first month of age.

Thus, it has to be understood that the immunogenic composition can be administered to the subject exemplary within the first three weeks of age or within the first two weeks of age.

In another specific aspect of the method according to the present invention said immunogenic composition is administered to sows during pregnancy and lactation.

Advantageously, the immunogenic composition of the present invention has been proven to be safe when administered to sows during pregnancy.

Thus, there is provided a method of vaccinating pigs against PEDV by administering the PEDV vaccine according to the present invention to a pregnant sow at least two times before farrowing, preferably three times before farrowing, more preferably two times before farrowing ("repeated doses"). Preferably, the pregnant sow is vaccinated with the PEDV vaccine according to the present invention twice with a single dose of said vaccine before farrowing. However, when the vaccine is administered to the sow two times, the first administration should occur between 12 and 4 weeks before farrowing, more preferably between 9 and 5 weeks before farrowing. The second administration should occur between 8 and 1 week before farrowing, more preferably between 6 and 1 week before farrowing.

In another specific aspect of the method according to the present invention the immunogenic composition is administered at two or more doses.

Advantageously, the immunogenic composition of the present invention has been shown to induce the production of antibodies specific for PEDV after two doses, preferably administered intranasally.

In another specific aspect of the method according to the present invention said immunogenic composition is administered to sows two times, the first administration between 9 and 5 weeks before farrowing and the second administration between 6 and 1 week before farrowing.

The immunogenic composition is, preferably, administered topically or systemically. Suitable routes of administration conventionally used are oral or parenteral administration, such as intranasal, intravenous, intramuscular, intraperitoneal, subcutaneous, as well as inhalation. However, depending on the nature and mode of action of a compound, the immunogenic composition may be administered by other routes as well. However, most preferred the immunogenic composition is administered intranasal or oral.

In another specific aspect of the method according to the present invention said immunogenic composition is administered intranasal, mucosal, oral, intradermal or intramuscular.

Advantageously, the immunogenic composition of the present invention has been proven to be effective when administered intranasal.

In another specific aspect of the method according to the present invention said immunogenic composition is administered intranasal or oral.

Preferably, the immunogenic composition comprises between $1\times10^2$ to $1\times10^9$ $TCID_{50}$/ml, more preferably between $1\times10^3$ to $1\times10^7$ $TCID_{50}$/ml and most preferably between $1\times10^4$ to $1\times10^6$ $TCID_{50}$/ml.

In another specific aspect of the method according to the present invention the immunogenic composition comprises between $1\times10^3$ to $1\times10^7$ $TCID_{50}$/ml.

The term "$TCID_{50}$/ml" refers to the measure of infectious virus titer. Specifically the tissue culture infectious dose fifty per milliliter (TCID50/ml) gives the dilution of a virus preparation at which 50% of a number of cell cultures inoculated in parallel with that dilution are infected.

In another specific aspect of the method according to the present invention the method results in a reduction of the shedding from day 2 after challenge or infection.

In another specific aspect of the method according to the present invention the method results in a reduction of the shedding from day 3 after challenge or infection.

In another specific aspect of the method according to the present invention the method results in a reduction of the shedding from day 4 after challenge or infection.

In another specific aspect of the method according to the present invention the method results in a reduction of the shedding from day 5 after challenge or infection.

In another specific aspect of the method according to the present invention the method results in a reduction of the shedding from day 7 after challenge or infection.

In another specific aspect of the method according to the present invention the method results in a reduction of the shedding from day 10 after challenge or infection.

In another specific aspect of the method according to the present invention the method results in a reduction of the shedding from day 5, 7 or 10 after challenge or infection.

Advantageously, the immunogenic composition of the present invention has been proven to reduce the shedding after infection or challenge.

The term "reduction of the shedding" means that the shedding is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected by the particular PEDV. It is in the general knowledge of a person skilled in the art how to measure the viral shedding.

The term "shedding" refers to secretions of PEDV in fecal discharges or feces. Thus, shedding may be determined by examining the virus titer in fecal discharges, feces or rectal swaps. The term "shedding" further encompasses the transfer of virus to susceptible animals (i.e. sentinels). It is in the general knowledge of a person skilled in the art how to measure the viral shedding such as by PCR, qPCR or ELISA.

In another specific aspect of the method according to the present invention the method increases the protection against a homologous challenge.

Advantageously, the immunogenic composition of the present invention has been proven to be protective after challenge.

The invention provides the use of the CDV vector of the present invention or of the immunogenic composition of the present invention for the manufacture of a medicament.

The invention also provides the use of the CDV vector of the present invention or of the immunogenic composition of the present invention for treating and/or preventing clinical signs caused by PEDV infection in a subject or for reducing diarrhea in a subject.

The present invention also relates to
the immunogenic composition of the present invention or
the vaccine or pharmaceutical composition of the present invention
for use in a method of reducing or preventing the clinical signs or disease caused by an infection with PEDV or for use in a method of treating or preventing an infection with PEDV in an animal, wherein preferably said animal is a pig.

In particular, the present invention also relates to the immunogenic composition or the vaccine of the present invention or the pharmaceutical composition of the present invention for use in a method for inducing an immune response against PEDV in a pig, in particular in a preferably pregnant sow.

In one aspect, the immunogenic composition or the vaccine of the present invention or the pharmaceutical composition of the present invention is for use in a method of reducing or preventing the clinical signs or disease caused by an infection with a PEDV in a piglet, wherein the piglet is to be suckled by a sow to which the immunogenic composition has been adminstered, and wherein said sow is preferably a sow to which the immunogenic composition has been administered while/when said sow has been pregnant, in particular with said piglet.

According to a particular preferred aspect of the present invention, in such use the immunogenic composition or the vaccine of the present invention or the pharmaceutical composition of the present invention is to be administered mucosally, preferably intranasally, such as to said sow.

The present invention further provides a method for inducing the production of antibodies specific for PEDV in a sow, wherein said method comprises administering the immunogenic composition of the present invention or the vaccine or pharmaceutical composition of the present invention, in particular comprising a CDV vector of the present invention encoding a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:1 or SEQ ID NO:2, to said sow. Also, the present invention further provides a method for inducing the production of antibodies specific for PEDV in a sow, wherein said method comprises administering the immunogenic composition of the present invention or the vaccine or pharmaceutical composition of the present invention, in particular comprising a CDV vector of the present invention encoding a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:16 or SEQ ID NO:17, to said sow.

Further, the present invention in particular provides a method of reducing or preventing the clinical signs or disease caused by an infection with a PEDV in a piglet, wherein said method comprises
administering the immunogenic composition of the present invention or the vaccine or pharmaceutical composition of the present invention, in particular comprising a CDV vector of the present invention encoding a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:1 or SEQ ID NO:2, to a sow, and
allowing said piglet to be suckled by said sow.

Furthermore, the present invention particularly provides a method of reducing or preventing the clinical signs or disease caused by an infection with a PEDV in a piglet, wherein said method comprises
administering the immunogenic composition of the present invention or the vaccine or pharmaceutical composition of the present invention, in particular comprising a CDV vector of the present invention encoding a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:16 or SEQ ID NO:17, to a sow, and
allowing said piglet to be suckled by said sow or, respectively, allowing said piglet to suckle said sow.

Preferably, said sow is a sow being pregnant, in particular with said piglet.

More preferably, such method of reducing or preventing the clinical signs or disease caused by an infection with a PEDV in a piglet, comprises the steps of
administering the immunogenic composition of the present invention or the vaccine or pharmaceutical composition of the present invention, in particular comprising a CDV vector of the present invention encoding a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:1 or SEQ ID NO:2, to a sow being pregnant with said piglet,
allowing said sow to give birth to said piglet, and
allowing said piglet to be suckled by said sow.

As another preferred option, such method of reducing or preventing the clinical signs or disease caused by an infection with a PEDV in a piglet, comprises the steps of
administering the immunogenic composition of the present invention or the vaccine or pharmaceutical composition of the present invention, in particular comprising a CDV vector of the present invention encoding a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:16 or SEQ ID NO:17, to a sow being pregnant with said piglet,
allowing said sow to give birth to said piglet, and
allowing said piglet to be suckled by said sow or, respectively, allowing said piglet to suckle said sow.

Preferably, the immunogenic composition of the present invention or the vaccine or pharmaceutical composition of the present invention is administered to the animal mucosally, such as by intranasal administration.

Most preferably in such method of reducing or preventing the clinical signs or disease caused by an infection with a PEDV in a piglet said immunogenic composition or said vaccine or pharmaceutical composition is administered mucosally, preferably intranasally, to said sow.

According to still another preferred aspect, the present invention also provides a kit for inducing an immune response against at least one pathogen, in particular against PEDV, in a pig or for vaccinating a pig, against a disease associated with PEDV and/or reducing the incidence or the severity of one or more clinical signs associated with or caused by PEDV in a pig, comprising:
a) a syringe or a dispenser capable of administering a vaccine to said pig; and
b) the immunogenic composition of the present invention or the vaccine or pharmaceutical composition of the present invention, and
c) optionally an instruction leaflet.

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of virology, molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

CDV Definitions

The term "3' non-coding region" of a specific gene (e.g. H gene) of a CDV, as used herein, in particular relates to an RNA sequence of an expressable specific gene (e.g. H gene) of a preferably infectious CDV, said RNA sequence flanking the 3' end of the coding sequence (i.e. the 3'end of the RNA triplet complementary to the start codon) and comprising the gene start sequence of said gene. Thus, more particular, the "3' non-coding region sequence", as mentioned herein, is an RNA sequence identical to the entire 3' non-coding sequence of an expressable specific gene (e.g. H gene) of a preferably infectious CDV. Still more particular, the "3' non-coding region", as mentioned herein, is an RNA sequence identical to the non-coding sequence of a specific gene (e.g. H, gene) of a CDV, wherein said non-coding sequence is flanked by (a) the coding sequence and (b) the intergenic sequence connecting said gene with the next gene in 3 direction.

As used herein, the term "intergenic region" in particular refers to the RNA sequence connecting the 5' end of a gene of a CDV with the 3' start of the adjacent gene in 5' direction of a CDV.

The term "gene start sequence", as used herein, is in particular equivalent to the term "gene start signal".

As used herein, it is understood that the term "genome promoter of a CDV" is equivalent to the term "genome leader sequence of a CDV".

PEDV Spike Protein Definitions

The term "PEDV" is well known to the person skilled in the art. PEDV stands for porcine epidemic diarrhea virus and is a member of the subfamily Coronavirinae of genus *Alphacoronavirus*.

The term "spike" refers to a specific protein of the PEDV that is well known by the person skilled in the art. The spike protein is the major inducer of antibodies and protective immune response. Further, the spike protein plays a major role in the cell entry program of PEDV by binding cellular receptors of the host cell and also by mediating virus-cell membrane fusion with the host cell.

The term "protein", "amino acid" and "polypeptide" are used interchangeable. The term "protein" refers to a sequence of amino acids (aa) composed of the natural occurring amino acids as well as derivatives thereof. The naturally occurring amino acids or genetically encoded amino acid residues, respectively, are well known in the art and are described in standard text books of biochemistry. Within the amino acid sequence the amino acids are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition. Further, the term also relates to protein fragments. Moreover, it includes chemically modified proteins. Such modifications may be artificial modifications or naturally occurring modifications such as phosphorylation, glycosylation, myristoylation and the like.

Molecular Biology Definitions

The phrase "sequence flanking the 5' end of" as described herein is in particular equivalent to the phrase "sequence covalently linked with the 5' end of" or, respectively, with the phrase "sequence, wherein the 3' terminal nucleotide thereof is covalently linked with the 5' terminal nucleotide of", and wherein it is particularly understood that said two terminal nucleotides are linked covalently between the phosphate group attached to the 5' carbon of the pentose and the 3' carbon atom of the adjacent pentose.

The phrase "sequence flanking the 3' end of" as described herein is in particular equivalent to the phrase "sequence covalently linked with the 3' end of" or, respectively, to the phrase "sequence, wherein the 5' terminal nucleotide thereof is covalently linked with the 3' terminal nucleotide of", and wherein it is particularly understood that said two terminal nucleotides are linked covalently between the 3' carbon atom of the pentose and the phosphate group attached to the 5' carbon of the adjacent pentose.

The term "vector" as it is known in the art refers to a polynucleotide construct, typically a plasmid or a bacterial artificial chromosome, used to transmit genetic material to a host cell. Vectors can be, for example, bacteria, viruses, phages, bacterial artificial chromosomes, cosmids, or plasmids. A vector as used herein can be composed of or contain either DNA or RNA. In some embodiments, a vector is composed of DNA. In some embodiments a vector is an infectious virus. Such a viral vector contains a viral genome which was manipulated in a way that it carries a foreign gene which has no function in the replication of the viral vector neither in cell culture nor in a host animal. According to specific aspects of the present disclosure a vector may be used for various aspects such as mere transmission of genetic material, for the transfection of host cells or organisms, for use as vaccines, e.g. DNA vaccines or for gene expression purposes. Gene expression is a term describing the biosynthesis of a protein in a cell as directed by a specific polynucleotide sequence called gene. In a specific aspect a vector may be an "expression vector", which is a vector that is capable of directing the expression of a protein encoded by one or more genes carried by the vector when it is present in the appropriate environment.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update, "PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 406; EPAO 370 573; U.S. Pat. No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

The term "viral vector" describes a genetically modified virus which was manipulated by recombinant DNA technique in a way so that its entry into a host cell results in a specific biological activity, e.g. the expression of a transgene carried by the vector. In a specific aspect the transgene is an antigen. A viral vector may or may not be replication competent in the target cell, tissue, or organism. It is in particular understood, that the term "viral vector", as used herein, is equivalent to the term "virus vector".

Generation of a viral vector can be accomplished using any suitable genetic engineering techniques well known in the art, including, without limitation, the standard techniques of restriction endonuclease digestion, ligation, transformation, plasmid purification, DNA sequencing, transfection in cell cultures, for example as described in Sambrook et al. (Molecular Cloning: A Laboratory Manual. Cold Spring Harbor Laboratory Press, N.Y. (1989)) or K. Maramorosch and H. Koprowski (Methods in Virology Volume VIII, Academic Press Inc. London, UK (2014)).

A viral vector can incorporate sequences from the genome of any known organism. The sequences can be incorporated in their native form or can be modified in any way to obtain a desired activity. For example, the sequences can comprise insertions, deletions or substitutions.

A viral vector can include coding regions for two or more proteins of interest. For example, the viral vector can include the coding region for a first protein of interest and the coding region for a second protein of interest. The first protein of interest and the second protein of interest can be the same or different. In some embodiments, the viral vector can include the coding region(s) for a third or a fourth protein of interest. The third and the fourth protein of interest can be the same or different. The total length of the two or more proteins of interest encoded by one viral vector can vary. For example, the total length of the two or more proteins can be at least about 200 amino acids. At least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

The terms "viral vector" and "viral construct" can be used interchangeably.

The term "construct", as used herein, refers to a recombinant nucleic acid such as a plasmid, a BAC, or a recombinant virus that has been artificially generated.

The term "plasmid" refers to cytoplasmic DNA that replicates independently of the bacterial chromosome within a bacterial host cell. In a specific aspect of the present invention the term "plasmid" and/or "transfer plasmid" refers to an element of recombinant DNA technology useful for construction of e.g. an expression cassette for insertion into a viral vector. In another specific aspect the term "plasmid" may be used to specify a plasmid useful for DNA vaccination purposes.

As used herein, the terms "nucleic acid" and "polynucleotide" are interchangeable and refer to any nucleic acid. The term "nucleic acid sequence" is understood to be equivalent to the term "nucleotide sequence". The term "nucleotide sequence" is understood to be equivalent to the term "polynucleotide sequence".

The term "nucleic acid", "nucleic acid sequence", "nucleotide sequence", "polynucleotide", "polynucleotide sequence", "RNA sequence" or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The terms "nucleic acid" and "polynucleotide" also specifically include nucleic acids composed of bases other than the five biologically occurring bases (adenine, guanine, thymine, cytosine and uracil).

As used herein, the term "promoter" or "promoter sequence" means a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and animals such as mammals (including horses, pigs, cattle and humans), birds or insects. A promoter can be inducible, repressible, and/or constitutive. Inducible promoters initiate increased levels of transcription from DNA under their control in response to some change in culture conditions, such as a change in temperature (Ptashne, 2014). Examples of promoters well known to the person skilled in the art are for example SV40 large T, HCMV and MCMV immediate early gene 1, human elongation factor alpha promoter, baculovirus polyhedrin promoter.

The term "complementary nucleotide sequences" describes one strand of the two paired strands of polynucleotides such as DNA or RNA. The nucleotide sequence of the complementary strand mirrors the nucleotide sequence of its paired strand so that for each adenosin it contains a thymin (or uracil for RNA), for each guanine a cytosin, and vice versa. The complementary nucleotide sequence of e.g. 5'-GCATAC-3' is 3'-CGTATG-5' or for RNA 3'-CGUAUG-5'.

The terms "gene", "gene of interest", as used herein have the same meaning and refer to a polynucleotide sequence of any length that encodes a product of interest. The gene may further comprise regulatory sequences preceding (5' non-coding or untranslated sequences) and following (3' non-coding or untranslated sequences) the coding sequence. The selected sequence can be full length or truncated, a fusion or tagged gene, and can be a cDNA, a genomic DNA, or a DNA fragment. It is generally understood that genomic DNA encoding for a polypeptide or RNA may include non-coding regions (i.e. introns) that are spliced from mature messenger RNA (mRNA) and are therefore not present in cDNA encoding for the same polypeptide or RNA. It can be the native sequence, i.e. naturally occurring form(s), or can be mutated, or comprising sequences derived from different sources or otherwise modified as desired. These modifications include codon optimizations to optimize codon usage in the selected host cell or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide.

The term "nucleotide sequence of interest" as used herein is a more general term than gene of interest as it does not necessarily comprise a gene but may comprise elements or parts of a gene or other genetic information, e.g. ori (origin of replication). A nucleotide sequence of interest may be any DNA or RNA sequence independently of whether it comprises a coding sequence or not.

The term "transcription" describes the biosynthesis of mRNA in a cell.

The term "expression" as used herein refers to transcription and/or translation of a nucleic acid sequence within a host cell. According to specific aspects of the present invention the term "expression" refers to transcription and/or translation of a heterologous and/or exogenous nucleic acid sequence within a host cell. The level of expression of a desired product in a host cell may be determined on the basis of either the amount of corresponding RNA or mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by RTqPCR (reverse transcription followed by quantitative PCR). Proteins expressed from a selected sequence can be quantitated by various methods, e.g. by ELISA, by Western blotting, by radioimmunoassays, by immunoprecipitation, by assaying for the biological activity of the protein, or by immunostaining of the protein followed by FACS analysis.

The term "expression cassette" or "transcription unit" or "expression unit" defines a region within a vector, construct or polynucleotide sequence that contains one or more genes to be transcribed, wherein the nucleotide sequences encoding the transcribed gene(s) as well as the polynucleotide sequences containing the regulatory elements contained within an expression cassette are operably linked to each other. They are transcribed from a promoter and transcription is terminated by at least one polyadenylation signal. In one specific aspect, they are transcribed from one single promoter. As a result, the different genes are at least transcriptionally linked. More than one protein or product can be transcribed and expressed from each transcription unit (multicistronic transcription unit). Each transcription unit will comprise the regulatory elements necessary for the transcription and translation of any of the selected sequences that are contained within the unit. And each transcription unit may contain the same or different regulatory elements. For example, each transcription unit may contain the same terminator, IRES element or introns may be used for the functional linking of the genes within a transcription unit. A vector or polynucleotide sequence may contain more than one transcription unit.

The term "viral titre" is a measure of infectious units per volume of a virus preparation. Viral titre is an endpoint in a biological procedure and is defined as the dilution at which a certain proportion of tests carried out in parallel show an effect (Reed and Muench, 1938). Specifically the tissue culture infectious dose fifty per milliliter (TCID50/ml) gives the dilution of a virus preparation at which 50% of a number of cell cultures inoculated in parallel with that dilution are infected.

"Transcription-regulatory elements" normally comprise a promoter upstream of the gene sequence to be expressed, transcription initiation and termination sites and a polyadenylation signal.

The term "transcription initiation site" refers to a nucleic acid in the construct corresponding to the first nucleic acid incorporated into the primary transcript, i.e. the mRNA precursor. The transcription initiation site may overlap with the promoter sequences.

The "termination signal" or "terminator" or "polyadenylation signal" or "polyA" or transcription termination site" or "transcription termination element" is a signal sequence which causes cleavage at a specific site at the 3' end of the eukaryotic mRNA and post-transcriptional incorporation of a sequence of about 100-200 adenine nucleotides (polyA tail) at the cleaved 3' end, and thus causes RNA polymerase to terminate transcription. The polyadenylation signal comprises the sequence AATAAA about 10-30 nucleotides upstream of the cleavage site and a sequence located downstream. Various polyadenylation elements are known such as tk polyA, SV40 late and early polyA, BGH polyA (described for example in U.S. Pat. No. 5,122,458) or hamster growth hormone polyA (WO2010010107).

"Translation regulatory elements" comprise a translation initiation site (AUG), a stop codon and a polyA signal for each individual polypeptide to be expressed. An internal ribosome entry site (IRES) may be included in some constructs. In order to optimize expression it may be advisable to remove, add or alter 5'- and/or 3'-untranslated regions of the nucleic acid sequence to be expressed to eliminate any potentially extra inappropriate alternative translation initiation codons or other sequences that may interfere with or reduce expression, either at the level of transcription or translation. Consensus ribosome binding sites (Kozak sequence) can be inserted immediately upstream of the start codon to enhance translation and thus expression. Increased A/U contents around this ribosome binding site further a more efficient ribosome binding.

By definition, every polynucleotide sequence or every gene inserted in a host cell and the respective protein or RNA encoded thereby is referred to as "exogenous", "exogenous sequence", "exogenous gene", "exogenous coding sequence", with respect to the host cell, when it comes from a different (virus) species. As used herein in respect to a sequence or gene of interest such as an antigen the term "exogenous" means that said sequence or gene of interest, specifically said antigen is expressed out of its natural species context. Accordingly, the PEDV S protein is one example (see Examples) of an exogenous antigen in respect to the CDV vector. As used herein, the term "exogenous RNA" or "exogenous nucleic acid sequence" in particular refers to a nucleic acid sequence that was introduced into the genome of a CDV virus from an external source, such as from a recombinant sequence. Examples of such external source comprise PEDV derived sequences. More particular, the introduction of the exogenous nucleic acid sequence results in a genome or a gene, respectively, having a non-naturally occurring portion. As used herein, the term "exogenous RNA" thus in particular refers to a nucleotide sequence, which is not naturally found in the CDV genome. Such non-naturally occurring portion or not naturally found sequence, respectively, can also be the result of the insertion of one naturally occurring nucleotide sequence into another naturally occurring nucleotide sequence.

By definition, every polynucleotide sequence or every gene inserted in a host cell and the respective protein or RNA encoded thereby is referred to as "heterologous", "heterologous sequence", "heterologous gene", "heterologous coding sequence", "transgene" or "heterologous protein" with respect to the host cell. This applies even if the sequence to be introduced or the gene to be introduced is identical to an endogenous sequence or an endogenous gene of the host cell. For example, a 5' non-coding region of an N gene of a CDV introduced into a CDV vector at a different site or in modified form than in the CDV wild type virus is by definition a heterologous sequence. As used herein in respect to a sequence or gene of interest such as an antigen, the term "heterologous" means that said sequence or gene of interest, specifically said antigen, is expressed out of its natural subspecies context.

The term "non-naturally occurring" means any sequence or gene of interest such as an antigen, which is not occurring in this context naturally, such as a hybrid sequence or a sequence or gene of interest such as an antigen from a different species, or sequence or gene of interest such as an antigen, which is not a product of nature due to artificial mutation, insertion, deletion or the like.

The term "recombinant" is used exchangeably with the terms "non-naturally occurring", "heterologous" and "exogenous" throughout the specification of this present invention. Thus, a "recombinant" protein is a protein expressed from a either a heterologous or an exogenous polynucleotide sequence. The term recombinant as used with respect to a virus, means a virus produced by artificial manipulation of the viral genome. A virus comprising a heterologous or an exogenous sequence such as an exogenous antigen encoding sequence is a recombinant virus. The term recombinant virus and the term non-naturally occurring virus are used interchangeably.

Thus, the term "heterologous vector" means a vector that comprises a heterologous or an exogenous polynucleotide sequence. The term "recombinant vector" means a vector that comprises a heterologous or a recombinant polynucleotide sequence.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

It is in particular understood in the context of the present invention that the term "being [ . . . ] identical with the sequence" is equivalent to the term "having [ . . . ] sequence identity with the sequence".

As used herein, it is in particular understood that the term "being at least X % identical with the sequence of SEQ ID NO:Y" is equivalent to the term "being at least X % identical with the sequence of SEQ ID NO:Y over the length of SEQ ID NO:Y" or to the term "being at least X % identical with the sequence of SEQ ID NO:Y over the entire length of SEQ ID NO:Y", respectively. In this context, "X" is any number from 70 to 100, in particular any integer selected from 70 to 100, such that "X % sequence identity" represents any of the percent sequence identities mentioned herein. Respectively, "Y" in this context is any integer selected from 1 to 17, such that "SEQ ID NO:Y" represents any of the SEQ ID NOs mentioned herein.

It is furthermore understood that the term "being at least 99% identical", as described herein, also (in one extreme of the range) comprises and relates to the term "being 100% identical" or "being identical with the sequence", respectively.

"Sequence identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, 91%, 92%, 93%, 94%, even more preferably 95%, 96%, 97%, 98%, 99%, 99.9% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, 91%, 92%, 93%, 94%, even more preferably 95%, 96%, 97%, 98%, 99%, 99.9% identity relative to the reference nucleotide sequence, up to 15%, preferably 10%, 9%, 8%, 7%, 6%, even more preferably 5%, 4%, 3%, 2%, 1%, 0.1% of the nucleotides in the reference sequence may be deleted or substituted with another nucleotide, or a number of nucleotides up to 15%, preferably 10%, 9%, 8%, 7%, 6%, even more preferably 5%, 4%, 3%, 2%, 1%, 0.1% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, 91%, 92%, 93%, 94%, even more preferably 95%, 96%, 97%, 98%, 99% sequence identity to a reference amino acid sequence, it is intended that the given amino acid sequence of the polypeptide is identical to the reference sequence except that the given polypeptide sequence may include up to 15, preferably up to 10, 9, 8, 7, 6, even more preferably up to 5, 4, 3, 2, 1 amino acid alterations per each 100 amino acids of the reference amino acid sequence. In other words, to obtain a given polypeptide sequence having at least 85%, preferably 90%, 91%, 92%, 93%, 94%, even more preferably 95%, 96%, 97%, 98%, 99% sequence identity with a reference amino acid sequence, up to 15%, preferably up to 10%, 9%, 8%, 7%, even more preferably up to 5%, 4%, 3%, 2%, 1% of the amino acid residues in the reference sequence may be deleted or substituted with another amino acid, or a number of amino acids up to 15%, preferably up to 10%, 9%, 8%, 7%, even more preferably up to 5%, 4%, 3%, 2%, 1% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the identity between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at www.accelrys.com), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at http://www.ncbi.nlm.nih.gov/.

Vaccine Definitions

An "immunogenic or immunological composition" refers to a composition of matter that comprises at least one antigen, or immunogenic portion thereof, that elicits an immunological response in the host of a cellular or antibody-mediated immune response to the composition.

The term "antigen" used herein is well understood in the art and includes substances which are immunogenic, i.e., immunogens, as well as substances which induce immunological unresponsiveness, or anergy, i.e., a lack of reactions by the body's defense mechanisms to foreign substances. As used herein, the term "antigen" is intended to mean full length proteins as well as peptide fragments thereof containing or comprising epitope.

An "immunogenic composition" as used herein can refer to a polypeptide or a protein, such as for example a viral surface protein that elicits an immunological response as described herein. The term "immunogenic fragment" or "immunogenic portion" refers to a fragment or truncated and/or substituted form of a protein or polypeptide that includes one or more epitopes and thus elicits the immunological response described herein. In general, such truncated and/or substituted forms, or fragments will comprise at least six contiguous amino acids from a full-length protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. As used within specific aspects of the present invention "vaccine" refers to a live vaccine or live virus, also called recombinant vaccine. In another specific aspect of the present invention "vaccine" refers to an inactivated or killed virus including virus like particles (VLPs). Thus, a vaccine may be a subunit vaccine or a killed (KV) or inactivated vaccine.

The term "Multiplicity of Infection (M.O.I.)" describes how many infectious units, e.g. TCID50, of a virus preparation are used per cell to infect cultured cells. For example, a M.O.I. of 0.01 means that for every 100 cells in a culture vessel one infectious unit is inoculated.

The term "DNA vaccination" or "polynucleotide vaccination" means direct inoculation of genetic material using suitable pharmaceutical compositions.

Various physical and chemical methods of inactivation are known in the art. The term "inactivated" refers to a previously virulent or non-virulent virus or bacterium that has been irradiated (ultraviolet (UV), X-ray, electron beam or gamma radiation), heated, or chemically treated to inactivate or kill such virus or bacterium while retaining its immunogenicity. Suitable inactivating agents include beta-propiolactone, binary or beta- or acetyl-ethyleneimine, gluteraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the inactivation process. One embodiment uses about 0.1 to 1% of a 37% solution of formaldehyde to inactivate the virus or bacterium. It is critical to adjust the amount of formalin to ensure that the material is inactivated but not so much that side effects from a high dosage occur.

More particularly, the term "inactivated" in the context of a virus means that the virus is incapable of replication in vivo or in vitro and, respectively, the term "inactivated" in the context of a bacterium means that the bacterium is incapable of reproduction in vivo or in vitro. For example, the term "inactivated" may refer to a virus that has been propagated in vitro, and has then been inactivated using chemical or physical means so that it is no longer capable of replicating. In another example, the term "inactivated" may refer to a bacterium that has been propagated, and then inactivated using chemical or physical means resulting in a suspension of the bacterium, fragments or components of the bacterium, such as resulting in a bacterin which may be used as a component of a vaccine.

As used herein, the terms "inactivated", "killed" or "KV" are used interchangeably.

The term "live vaccine" refers to a vaccine comprising either a living organism or a replication competent virus or viral vector.

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA) and the mixture is subsequently lyophilized or dehydrated by other methods. Prior to vaccination, the mixture is then rehydrated in aqueous (e.g., saline, phosphate buffered saline (PBS) or non-aqueous solutions (e.g., oil emulsion, aluminum-based adjuvant).

As used herein, "pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), JohnWiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIM adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Attenuation" means reducing the virulence of a pathogen. In the present invention "attenuation" is synonymous with "avirulent". In the present invention, an attenuated virus is one in which the virulence has been reduced so that it does not cause clinical signs of infection but is capable of inducing an immune response in the target animal, such as in canine, but may also mean that the clinical signs are reduced in incidence or severity in animals, such as canine, infected with the attenuated virus, especially the CDV vector as claimed, in comparison with a "control group" of animals infected with non-attenuated virus or pathogen and not receiving the attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent pathogen such as for example an attenuated viral vector as claimed, especially the CDV vector as claimed, is suitable for the generation of a modified live vaccine (MLV) or modified live immunogenic composition.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

An "immune response" or "immunological response" means, but is not limited to, the development of a cellular and/or antibody-mediated immune response to the (immunogenic) composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

"Protection against disease", "protective immunity", "functional immunity", "reduction of clinical symptoms", "induction/production of neutralizing antibodies and/or serum conversion", and similar phrases, means a partial or complete response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

The term "neutralizing antibody" relates to an antibody that is capable of keeping an infectious agent, usually a virus, e.g., PEDV or CDV, from infecting a cell by neutralizing or inhibiting its biological effect. Neutralization can happen when antibodies bind to specific viral antigens, blocking the pathogen from entering their host cells. In one example it prevents the virus from binding to its receptor(s) and getting its genetic material inside the cell.

The term "antibody" or "immunoglobulin," as used interchangeably herein, includes whole antibodies and any antigen binding fragment (antigen-binding portion) or single chain cognates thereof. An "antibody" comprises at least one heavy (H) chain and one light (L) chain. In naturally occurring IgGs, for example, these heavy and light chains are inter-connected by disulfide bonds and there are two paired heavy and light chains, these two also inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR) or Joining (J) regions (JH or JL in heavy and light chains respectively). Each $V_H$ and $V_L$ is composed of three CDRs, three FRs and a J domain, arranged from amino-terminus to carboxy-terminus in the following order: FR1, CDR1, FR2, CDR2, FR3, CDR3, J. The variable regions of the heavy and light chains bind with an antigen. The constant regions of the antibodies may mediate the binding of the immunoglobulin to host tissues or factors, including various cells of the immune system (e.g., effector cells) or humoral factors such as the first component (Clq) of the classical complement system.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of a disease, such as of porcine epidemic diarrhea or malaria. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge with the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

The term "reduction of viremia" induced by a virus means, but is not limited to, the reduction of virus entering the bloodstream of an animal, wherein the viremia level, i.e. the number of virus DNA or RNA copies per mL of blood serum or the number of plaque forming colonies per deciliter of blood serum, is reduced in the blood serum of animals receiving the composition of the present invention by at least 50% in comparison to animals not receiving the composition and may become infected. More preferably, the viremia level is reduced in animals receiving the composition of the present invention by at least 90%, preferably by at least 99.9%, more preferably by at least 99.99%, and even more preferably by at least 99.999%.

As used herein, the term "viremia" is particularly understood as a condition in which virus particles reproduce and/or circulate in the bloodstream of an animal, in particular of a mammal, a bird, or of an insect.

"Safety" refers to the absence of adverse consequences in a vaccinated animal following vaccination, including but not limited to: potential reversion of a virus-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—, an immune response in said animal.

"Mortality", in the context of the present invention, refers to death caused by an infection, and includes the situation where the infection is so severe that an animal is euthanized to prevent suffering and provide a humane ending to its life.

Formulations

The subject to which the composition is administered is preferably an animal, including but not limited to cattle, horses, sheep, pigs, poultry (e.g. chickens), goats, cats, dogs, hamsters, mice and rats, most preferably the mammal is a swine.

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Methods of Treatment

Preferred routes of administration include but are not limited to intranasal, oral, intradermal, and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intraperitoneally, and depending on the desired duration and effectiveness of the treatment, the compositions according to the invention may be administered once or several times, also intermittently, for instance on a daily basis for several days, weeks or months and in different dosages such as about $10^3$ to $10^8$ TCID50 (see viral titre above). In a specific aspect of the present invention the dosage is about $10^3$ to $10^8$ TCID50, especially for live virus/live vaccine.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration, preferably for administration to a mammal, especially a pig. Associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

The following example is included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

PEDV-S Expression by Recombinant CDV Vectors

In an in vitro experiment, a full plasmid (pBR322) encoding fully CDV genome derived from Lederle vaccine strain (Lederle; ATCC VR-128) was digested using SacII endonuclease followed by cloning PEDV spike (S) protein encoding cassette between the P gene and the M gene (resulting in a sequence comprising SEQ ID NO:14). Upon cloning and rescue of recombinant CDV-PEDV-S, it was possible to show expression of Porcine Epidemic Diarrhea Virus spike protein of a 2b genotype in CDV associated fluorescent focuses. Respective results are also achieved for a corresponding CDV vector (i.e. only differing in the sequence encoding the Porcine Epidemic Diarrhea Virus spike protein of a 2a genotype SEQ ID NO:15). Results obtained for both vectors by immunofluorescence indicate strong expression of spike protein of PEDV in all CDV infected syncytia (data not shown).

Example 2

Vaccine Efficacy Study

Porcine epidemic diarrhea (PED) is a highly contagious swine disease that can have tremendous economic impact. While all age classes of pigs are susceptible to infection, severe clinical signs and mortality are mainly seen in suckling piglets. The causative agent is PED virus (PEDV), an enveloped, single positive-stranded RNA-virus of the genus *Alphacoronavirus* within the Coronaviridae virus family. In Europe, PEDV first occurred in the late 1970ies in England. Afterwards it spread through whole Europe causing sporadic outbreaks. In the late 1990ies, PEDV had disappeared from the European pig farms as evidenced by very low seroprevalence and non-existent disease reporting. Outbreaks and endemic infections were still reported from Asia where the disease has high impact on the productivity of industrialized pig farms. Starting from 2005, PED cases were again reported from Europe, i.e. Italy. After the introduction of an apparently highly virulent PEDV into the United States in 2013, cases were also reported from Central Europe, including Germany and neighboring countries. The latter cases were caused by related but distinct PEDV strains (so-called S-INDEL strains). In Germany, cases were reported starting from May 2014 with high morbidity and variable lethality in suckling pigs.

This study, in which a CDV backbone derived from Lederle vaccine strain (c.f. Example 1) with an insert of the sequence of SEQ ID NO:4 (encoding a PEDV Spike protein) between the P gene and the M gene (the vector thus comprising the sequence of SEQ ID NO:8) was tested as vector vaccine (named hereinafter "CDV_PEDV-Spike vaccine" or "CDV PEDV-Spike vector vaccine", respectively), included six sows and their offspring.

All animals were checked for PEDV by RT-qPCR targeting the S-gene, and PEDV-specific antibodies. Only negative animals were enrolled in the study.

Three treatment groups (see below) received randomly assigned animals:

Group 1 (negative control): Two sows (designated #1 and #2), unvaccinated

Group 2 (positive control): Two sows (designated #3 and #4), unvaccinated

Group 3 (CDV_PEDV-Spike): Two sows (designated #5 and #6), vaccinated with CDV_PEDV-Spike vector vaccine.

The vaccination of the two sows of group 3 was done according to the following scheme, wherein the stock titer of the CDV_PEDV-Spike vaccine, defined by endpoint titration, was $7.94 \times 10^4$ TCID50/ml:

9 weeks prior to expected farrowing date: each of the two sows received 4 ml of the vaccine intranasally (2 ml in each nostril);

6 weeks prior to expected farrowing date: each of the two sows received 4 ml of the vaccine intranasally (2 ml in each nostril);

3 weeks prior to expected farrowing date: each of the two sows received 4 ml of the respective vaccine intranasally (2 ml in each nostril) and additionally 2 ml intramuscularly.

Piglets born to sows of group 1 (13 piglets of sow #1 and 12 piglets of sow #2) were orally mock-inoculated. Piglets born to sows of group 2 (12 piglets of sow #3 and 14 piglets of sow #4), and group 3 (5 piglets of sow #5 and 15 piglets of sow #6) were orally challenged with a PEDV field strain (named "PEDV EU" hereinafter) at an age of 4 days of life.

For inoculation of piglets of groups 2 and 3, cell culture adapted PEDV EU was used. The titer was $2.15 \times 10^5$ TCID50/ml. Piglets of groups 2 and 3 were orally inoculated. In this case, each piglet received 1 ml of a 1:10 diluted viral stock (titer $2.15 \times 10^4$ TCID50) using 2 ml syringes.

Piglets of group 1 were orally mock-inoculated using 1 ml cell culture medium in 2 ml syringes.

During the whole trial, rectal swabs (COPAN plain swabs without medium) were taken at the day of inoculation and on day 1 to 10 post inoculation (pi) as well as day 14, 17 and 20/21 pi of all animals for RT-qPCR analyses. Additional rectal swabs were taken from 4 piglets of each sow prior to inoculation and two days post challenge for bacteriological examination. Moreover, clinical signs indicative for PED were recorded daily using the established standardized cumulative score system (see below). Blood samples were taken at the day of inoculation and day 14 and 20/21 pi (end of trial) or the day of euthanasia or death of the respective animal.

Clinical Monitoring

The established cumulative clinical score was used for daily monitoring for clinical signs indicative for PED (see table below).

TABLE 1

Cumulative clinical score for clinical signs indicative for PED

| Score | General behaviour | Feed intake/suckling | Gastrointestinal symptoms |
|---|---|---|---|
| 0 | Agile, attentive, no abnormalities | Greedy suckling, good filled stomach, intake of piglet feed | Physiological feces |
| 1 | Slight depression | Slow suckling, hardly interested in piglet feed | Pasty feces, vomiting |
| 2 | Depression, isolaton from group, vocalisation (moaning) | Reluctant feed intake, hardly interested in suckling/piglet feed, sunken flanks | Watery feces, reddened anal region, vomiting |
| 3 | Lateral position, signs of severe dehydration, low body temperature | Total anorexia, decreasing of milk production of sow | Watery feces with blood or fibrin added, highly reddened anal region, vomiting |

Sample Preparation and Nucleic Acid Extraction

Rectal swabs were submerged in 1 ml Dulbecco's Modified Eagle Medium and incubated for 1 hour at room temperature. Viral RNA was extracted using either the QIAmp ViralRNA Mini Kit (Qiagen) or the NucleoMagVet-Kit in combination with the KingFisher extraction platform. The RNA was stored at −20° degree until further use.

Blood samples were centrifuged at 2031×g for 20 min at room temperature to obtain serum. The resulting serum was aliquoted and stored at −20° C.

Virus Detection

To detect PEDV shedding, RT-qPCR-systems targeting the S-gene of PEDV were used as previously described (Stadler et al., BMC Vet Res. 11:142 (2015)). Samples taken at days 0 to 7 dpi and at 10 and 20/21 dpi were tested for PEDV-genome. The amount of genome copies/µl was calculated using an in-house standard.

Antibody Detection

A commercial indirect ELISA (INgezim PEDV, INGENASA, Madrid, Spain) was performed with all sera according to the producer's manual.

Bacteriology

Fecal swabs of four piglets per litter were taken at 0 and 2 dpi for differential bacteriology.

Statistics

Shapiro-Wilk test was used for normality testing and a Mann-Whitney rank sum test was conducted as implemented in the software package. Statistical significance was tested using SigmaPlot software.

Results

Antibody Detection in Serum:

All piglets of the CDV group showed positive results in the ELISA (detecting antibodies against PEDV Spike protein) prior to challenge inoculation due to antibody positive colostrum intake, while all animals of the positive and negative control group showed clearly negative results.

At 14 dpi all but three piglets in the positive control group seroconverted, while all animals in the vaccine group showed still high amounts of PEDV specific IgG in serum samples.

At the end of the study all piglets of the CDV group and of the positive control group showed strongly positive results in the ELISA. None of the animals in the negative control seroconverted during the whole trial.

In a further study it was also seen that respective antibody results were likewise achieved when the mother sows were only vaccinated twice via the intranasal route.

Bacteriology:

Fecal swabs taken at 0 and 2 dpi did not show any pathogenic bacteria. The bacterial flora did not undergo significant changes upon infection.

Clinical Signs:

Piglets of the positive control group (group 2) clearly showed clinical signs indicative for PEDV over 7 days starting with vomiting 24 hpi followed by diarrhea. 8 of 26 of the piglets had to be euthanized due to severe dehydration and clinical score values over 6 (humane endpoint). First clinical signs indicative for PEDV were detectable at 36 hpi.

In total, the clinical signs of the CDV vector vaccinated and PEDV challenged piglets (group 3) were better regarding the general behavior and only 2 of 20 (10%) of the pigs of group 3 had to be euthanized due to severe dehydration and clinical score values over 6 (as compared to 31% of the piglets of group 2).

Animals in the negative control stayed healthy during the whole trial.

Shedding of Virus

A clear difference in virus shedding could be detected between the challenged groups. At 1 dpi all challenged piglets were positive for virus genome in rectal swabs, but animals in the CDV-PEDV vaccinated group showed significantly lower PEDV genome copy numbers (mean CT value 32.79), then in challenge group (mean CT value 26.65).

Also, while for the next five days pi, the genome load in rectal swabs of the CDV group was quite similar to the positive control, beginning at 7 dpi the detectable amount of virus genome declined below the cutoff level in piglets protected by the vaccinated sows, while all animals in the positive control group still shed PEDV.

No PEDV genome could be detected in swabs of the negative control group.

In conclusion, the outcome of the study was that piglets born to sows vaccinated with the CDV PEDV-Spike recombinant vaccine showed a reduction of clinical signs, as compared to the positive control, and in particular, a great improvement was seen with regard to the mortality/letality of the piglets. Furthermore, virus shedding after the PEDV challenge was significantly reduced.

Besides, an animal study corresponding to the above described vaccine efficacy study is performed, wherein a CDV backbone derived from Lederle vaccine strain (c.f. Example 1) with an insert encoding the PEDV Spike protein of SEQ ID NO:17 between the P gene and the M gene is administered twice (5 weeks prior to farrowing and 2 weeks prior to farrowing), and wherein a highly virulent genotype 2a PEDV field strain is used for the challenge. Piglets born to sows vaccinated with this recombinant vaccine show reduced mortality or a reduction of clinical signs, as compared to the challenge control.

Example 3

This animal study, in which a CDV backbone derived from Lederle vaccine strain (c.f. Examples 1 and 2) with an insert encoding the PEDV Spike protein of SEQ ID NO:15 between the P gene and the M gene was tested as vector vaccine (named hereinafter "CDV_PEDV-G2a vaccine" or "CDV PEDV-G2a Spike vector vaccine", respectively), included twenty (20) sows and their offspring.

Only animals which were considered negative for PEDV by qRT-PCR and ELISA were enrolled in the study.

Three treatment groups (see below) received randomly assigned animals:
Group 1 (Strict negative control): Four sows (designated 1-4), unvaccinated;
Group 2 (Challenge control): Eight sows (designated 5-12), unvaccinated;
Group 3 (CDV_PEDV-G2a-Spike): Eight sows (designated 13-20), vaccinated with CDV PEDV-G2a-Spike vector vaccine.

The vaccination of the 8 sows of group 3 was done at 5 weeks pre-farrow (DO) and 2 weeks pre-farrow (D21) of the study, wherein the stock titer of the CDV_PEDV-G2a Spike vaccine, defined by endpoint titration, was $2.57 \times 10^5$ TCID50/ml. At each vaccination, the sows received 4 mL of the vaccine intranasally (2 mL in each nostril).

Piglets born to sows of group 1 (41 piglets in total) were not challenged (strict controls). Piglets born to sows of group 2 (81 piglets in total), and group 3 (83 piglets in total) were orally challenged with a highly virulent PEDV field strain belonging to G2a genotype with the dose $2.0 \times 10^3$ $TCID_{50}/2$ mL dose (1 mL intranasal+1 mL oral) at an age of 3-7 days of life.

During the whole trial, rectal swabs were taken at the day prior to inoculation and on day 1, 3, 7 and 14 pi (post challenge virus inoculation).

Sample Preparation and Nucleic Acid Extraction

Rectal swabs were submerged in 2 ml Minimum Essential Medium (MEM) upon collection and stored at −70° C. prior to processing. Sample were processed by vortexing for 10 seconds followed by centrifugation for 10 minutes at 1,500×g at 4° C. Following processing, 100 µl/sample was used for viral RNA extraction using the BS96 Vet 100 BioSprint extraction platform with the BioSprint One-For-All Vet Kit (Qiagen) The RNA was stored at −20° degree until further use.

Blood samples were centrifuged at 1960×g for 10 min at room temperature to obtain serum. The resulting serum was aliquoted and stored at −70° C.

Virus Detection

To detect PEDV shedding, an internally derived RT-qPCR-system targeting the S-gene of PEDV was used: The quantitative one-step RT-PCR kit (iTaq Universal One-Step RT-PCR kit; BioRad, cat no. 1725140) was used for the assay. Real-time RT-PCR was carried out in a 25 µl reaction containing 2 µl of extracted total nucleic acid, 0.75 µl of probe (4 µM), 0.5 µl of each primer (10 µM), 12.5 µl of 2×RT-PCR mix, 0.5 µl iScript reverse transcriptase and 8.25 µl of DEPC-treated water. See Table 2 below for primer, probe and ultramer sequences. The reaction took place using a CFX96 real-time PCR detection system (BioRad) under the following conditions: initial reverse transcription at 50° C. for 30 min, followed by initial denaturation at 95° C. for 5 min, 40 cycles of denaturation at 95° C. for 15 s and annealing and extension at 57° C. for 30 s. To generate quantitative data, a PEDV ultramer was included in each run (Integrated DNA Technologies). The lyophilized ultramer (4 nmol) was resuspended in DEPC-treated, nuclease-free sterile water to generate a stock concentration of 1.0E+10 genomic copies per µl (gc/µl). From the stock ultramer, 10 fold serial dilutions from 1.0E+08 to 1.0E+01 were made in the DEPC-treated water. The concentration was confirmed by qubit dsDNA HS Assay prior to use. The optical data were analyzed using CFX Manager software. For each determination, the threshold lines were automatically calculated using the regression setting for cycle threshold (Ct) determination mode. Baseline subtraction was done automatically using the baseline subtracted mode. Curves with baseline end values of less than 10 were manually corrected.

TABLE 2

Probe (Pr), primer (F/R), and ultramer sequences used for the internally derived RT-qPCR-system.

| Probe/primer name | Sequence |
|---|---|
| 0086-001-1 Pr | 56-FAM/ACAGAGCCTGTGTTGGTGTATAGTAACAT/3BHQ_1 (SEQ ID NO: 18) |
| 0089-065-1 F | TATAGTGGGTGTTATTTCTAGTT (SEQ ID NO: 19) |
| 0086-001-2 R | GCCAATACTGCCAGATTTACA (SEQ ID NO: 20) |
| PEDV-ultramer | 5'/TGATGATATAGTGGGTGTTATTTCTAGTTTGTCTAGCTCCACTTTTAACAGTACTAGGGAGTTGCCTGGTTTCTTCTACCATTCTAATGATGGCTCTAATTGTACAGAGCCTGTGTTGGTGTATAGTAACATAGGTGTTTGTAAATCTGGCAGTATTGGCTATGTCCCAT/3' (SEQ ID NO: 21) |

Antibody Detection

An in house developed CCIF assay was used to test serum and milk samples from this study: A wild-type PEDV isolate (Genogroup 2a) was diluted 1:100 into PEDV growth media (MEM+2.5% HEPES+0.3% Tryptose phosphate broth+ 0.02% yeast+10 µg/mL trypsin). The diluted virus (100 µL/well) was inoculated onto two-day old 96-well plates planted with VERO cells. Prior to infection, cell growth media was removed from the plates and they were washed twice with 100₄, of PEDV growth media. Plates were incubated for 24 hours at 37±2° C.+CO2 (4-6%). Following incubation, the supernatant was discarded and plates were washed twice with 200 µL/well 1×PBS. For fixation, 200 µL/well of Ethanol was added. Plates were incubated at room temperature for 30 minutes, air-dried, then stored at −20° C. until use. Prior to use in the assay, plates were rehydrated with 200 µl/well 1×PBS (Gibco) for 10 min at room temperature and blocked with 100 µl/well buffer (1×PBS+1% normal goat serum+0.1% triton X) for 15 minutes at 37° C. Serial two-fold dilutions of serum samples were prepared in a dilution buffer (1×PBS+5% BSA+1% normal goat serum+0.1% titron-X 100) containing a 1:1000 dilution of PEDV Mab antibody (Median diagnostics). Diluted samples (50 µl/well) were added to the prepared plates and incubated at 37° C. for 1 hour. Following incubation, plates were washed three times with 200 µl/well 1×PBS. A total of 50 µl/well of diluted secondary antibodies [Alexa594 goat anti-mouse IgG (Fisher, 1:500 dilution); FITC labeled, goat anti-pig IgG (BioRad, 1:500 dilution); Hoechst 33342 (Fisher, 1:1000 dilution)] was then added to each plate and incubated at 37° C. for 1 hour. Following incubation, plates were washed three times with 200 µl/well 1×PBS. Fluorescence was observed where PEDV-infected cells bound by Mab3F12 showed specific red fluorescence. Co-localization of green fluorescence indicated binding of pig IgG. The highest dilution where specific green fluorescence was detected was equivalent to the IgG titer.

Results

Mortalities

In group 1 (strict control) 40 pigs survived, in group 2 (challenge control) 16 pigs survived, and in group 3 (CDV-PEDV-G2a spike vaccinated) 34 pigs survived, resulting in an average mortality of 2% (group 1), 80% (group 2), and 59% (group 3), respectively.

Antibody Response

Specific PEDV antibody response after challenge revealed that the mean levels of CCIF IgG antibody titers in the sow sera and milk were higher in the CDV-PEDV-G2a spike vaccinated group than in group 2 (challenge control). This indicates that the vaccinated sows were strongly responding by boosting the IgG levels in milk and sera after contracting the virus from infected piglets post challenge. In comparison to this, the antibody titers of the sows of the challenge control, merely resulting from PEDV infection through contact with the challenged piglets (and their feces), were significantly lower.

Shedding of Virus

On day 3 post challenge virus inoculation, relatively similar mean RNA loads were detected in the vaccinated and non-vaccinated group, reaching 9.2 and 9.8 group mean log 10 PEDV genomic copies for the CDV-PEDV-G2a spike vaccinated group and the challenge control group, respectively. On D48 (7 dpi) and D55 (14 dpi), the mean log 10 PEDV genomic copy number in the CDV-PEDV-G2a spike vaccinated group were 3.2 and 2.0 logs 10, respectively, while in the challenge control group were 5.5 and 3.9 logs 10, respectively, indicating the reduction of 2.3 and 1.9 logs on days 7 and 14 pi, respectively. Although no longer term monitoring of shedding has been performed, the tendency of dynamics of shedding observed on days 7 and 14 post challenge virus inoculation clearly indicates a shortened shedding time in the vaccinated animals in accordance with the results as described above under Example 4.

No PEDV genome could be detected in swabs of the strict negative control group.

In conclusion, the outcome of the study was that piglets born by or, respectively, suckled by sows vaccinated with the CDV PEDV-G2a spike recombinant vaccine showed a significant reduction of mortality, as compared to the piglets of the control group, when challenged with a highly virulent PEDV strain. Also, these piglets receiving PEDV protective IgG antibodies from milk, via transfer of maternal antibodies in the initial days post partum, revealed a significant reduction of virus shedding post challenge, which is an important epidemiological parameter, on days 7 and 14 post infection.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

The Following Clauses are Also Disclosed Herein:

1. A canine distemper virus (CDV) vector comprising a heterologous nucleotide sequence of interest, wherein said heterologous nucleotide sequence of interest encodes a porcine epidemic diarrhea virus (PEDV) antigen.
2. The CDV vector of clause 1, wherein the PEDV antigen is selected from the group consisting of PEDV spike (S) protein and PEDV nucleoprotein (N protein).
3. The CDV vector of clause 1 or 2, wherein the PEDV antigen is a PEDV S protein, and wherein said PEDV S protein preferably comprises or consists of an amino acid sequence being at least 70%, 80%, 85%, 90%, 91%, 92%, 93%, 94%, 95%, 96%, 97%, 98%, or 99% identical with the sequence of SEQ ID NO: 1 or SEQ ID NO:2.
4, The CDV vector of any one of clauses 1 to 3, wherein the PEDV antigen is a PEDV S protein, and wherein said PEDV S protein preferably comprises or consists of an amino acid sequence being at least 70%, 80%, 85%, 90%, 91%, 92%, 93%, 94%, 95%, 96%, 97%, 98%, or 99% identical with the sequence of SEQ ID NO:16 or SEQ ID NO:17.
5. The CDV vector of any one of clauses 1 to 4, wherein said heterologous nucleotide sequence of interest encodes a PEDV S protein, and wherein said heterologous nucleotide sequence of interest consists of or comprises an RNA sequence being at least 70%, 80%, 85%, 90%, 91%, 92%, 93%, 94%, 95%, 96%, 97%, 98%, or 99% identical with the sequence of any one of SEQ ID NOs:3 to 5.
6. The CDV vector of any one of clauses 1 to 5, wherein said heterologous nucleotide sequence of interest is an RNA sequence of interest.
7. The CDV vector of any one of clauses 1 to 6, wherein said heterologous nucleotide sequence of interest is
   located between a P gene and an M gene of a CDV; and/or
   said heterologous nucleotide sequence of interest is a heterologous RNA sequence of interest, and wherein said heterologous RNA sequence is operably linked to a gene start (GS) sequence located in 3' direction of said heterologous RNA sequence and/or to the genome promoter of a CDV.
8. The CDV vector of clause 7, wherein said GS sequence is included in an exogenous 3' non-coding region of a gene of a CDV, and wherein said exogenous 3' non-coding region of a gene of a CDV preferably flanks the 3'end of the heterologous RNA sequence of interest.
9. The CDV vector of any one of clauses 1 to 8, comprising an RNA sequence being at least 70%, 80%, 85%, 90%, 91%, 92%, 93%, 94%, 95%, 96%, 97%, 98%, or 99% identical with the sequence of SEQ ID NO:6 or SEQ ID NO:7.
10. The CDV vector of any one of clauses 1 to 9, comprising an RNA sequence being at least 70%, 80%, 85%, 90%, 91%, 92%, 93%, 94%, 95%, 96%, 97%, 98%, or 99% identical with the sequence of SEQ ID NO:8.
11. The CDV vector of any one of clauses 1 to 10, further comprising an RNA sequence consisting of or comprising an RNA sequence being at least 70%, 80%, 85%, 90%, 91%, 92%, 93%, 94%, 95%, 96%, 97%, 98%, or 99% identical with the sequence of SEQ ID NO:9, and wherein said RNA sequence flanks the 5'end of the RNA sequence being at least 70%, 80%, 85%, 90%, 91%, 92%, 93%, 94%, 95%, 96%, 97%, 98%, or 99% identical with the sequence of SEQ ID NO:8.
12. The CDV vector of any one of clauses 1 to 11, further comprising an RNA sequence consisting of or comprising an RNA sequence being at least 70%, 80%, 85%, 90%, 91%, 92%, 93%, 94%, 95%, 96%, 97%, 98%, or 99% identical with the sequence of SEQ ID NO:10, and wherein said RNA sequence flanks the 3'end of the RNA sequence being at least 70%, 80%, 85%, 90%, 91%, 92%, 93%, 94%, 95%, 96%, 97%, 98%, or 99% identical with the sequence of SEQ ID NO:8.
13. A nucleic acid molecule which encodes the CDV vector of any one of the preceding clauses, and wherein said nucleic acid molecule is preferably a DNA molecule.
14. The DNA molecule of clause 13, wherein said molecule comprises a DNA sequence encoding a PEDV spike (S) protein, and wherein said sequence is preferably a DNA sequence being at least 70%, 80%, 85%, 90%, 91%, 92%, 93%, 94%, 95%, 96%, 97%, 98%, or 99% identical with the sequence of SEQ ID NO:11 or SEQ ID NO:12.
15. A DNA molecule, in particular the DNA molecule of clause 13 or 14, wherein said molecule comprises a DNA sequence being at least 70%, 80%, 85%, 90%, 91%, 92%, 93%, 94%, 95%, 96%, 97%, 98%, or 99% identical with the sequence of SEQ ID NO:13.
16. A DNA molecule, in particular the DNA molecule of any one of clauses 13 to 15, wherein said molecule comprises a DNA sequence being at least 70%, 80%, 85%, 90%, 91%, 92%, 93%, 94%, 95%, 96%, 97%, 98%, or 99% identical with the sequence of SEQ ID NO: 14.
17. A mammalian host cell containing the CDV vector or nucleic acid molecule or DNA molecule according to any one of the preceding clauses.
18. The CDV vector or nucleic acid molecule according to any one of the preceding clauses for use as a medicament, preferably as a vaccine.
19. A DNA construct comprising a DNA molecule according to any one of clauses 13 to 18.
20. An RNA transcript of the DNA construct of clause 19.
21. A cell transfected with the DNA construct of clause 19.
22. A cell transfected with the RNA transcript of clause 20.
23. A method for the preparation of an infectious CDV containing a heterologous gene, in particular for preparing the CDV vector of any one of clauses 1 to 12, wherein said method comprises the steps of:
a. providing a host cell expressing a heterologous RNA polymerase;
b. transfecting the host cell with the DNA construct of clause 19, and wherein the DNA molecule is transcribed by the heterologous RNA polymerase, and
c. isolating the viruses produced by the cells.
24. Use of the vector of any one of clauses 1 to 12 or of the cell according to any one of clauses 17, 21 and 22 for the manufacture of an immunogenic composition or a vaccine.
25. An immunogenic composition comprising
the CDV vector according to any one of clauses 1 to 12, wherein said vector is optionally an infectious and/or attenuated virus or said vector is optionally an attenuated and/or modified live virus, and optionally
a recombinant protein expressed by said vector and/or a quarternary structure comprising a plurality of a recombinant protein expressed by said vector, and optionally
a pharmaceutical- or veterinary-acceptable carrier or excipient, wherein said carrier is preferably suitable for oral, intradermal, intramuscular or intranasal application.
26. The immunogenic composition of clause 25, wherein said recombinant protein expressed by the vector is
a PEDV S protein, or
a PEDV N protein.
27. The immunogenic composition of clause 25 or 26, comprising or consisting of
the CDV vector of any one of clauses 1 to 12, and
a recombinant protein expressed by said vector, wherein said recombinant protein expressed by said vector is a PEDV S protein or a PEDV N protein, and optionally
a pharmaceutical- or veterinary-acceptable carrier or excipient, wherein said carrier is preferably suitable for oral, intradermal, intramuscular or intranasal application.
28. The immunogenic composition of any one of clauses 25 to 27, wherein said recombinant protein expressed by said vector is a PEDV S protein.
29. The immunogenic composition of any one of clauses 25 to 28, wherein said recombinant protein expressed by said vector is a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:1 or SEQ ID NO:2.
30. The immunogenic composition of any one of clauses 25 to 29, wherein said recombinant protein expressed by said vector is a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:16 or SEQ ID NO:17.
31. A vaccine or pharmaceutical composition comprising
a. the vector according to any one of clauses 1 to 12, and
b. a recombinant protein expressed by said vector and/or a quarternary structure comprising a plurality of a recombinant protein expressed by said vector, and
c. a pharmaceutical- or veterinary-acceptable carrier or excipient, preferably said carrier is suitable for intranasal application, and
d. optionally said vaccine further comprises an adjuvant.
32. The vaccine or pharmaceutical composition of clause 31, wherein said recombinant protein expressed by said vector is a PEDV S protein or a PEDV N protein.

33. The vaccine or pharmaceutical composition of clause 31 or 32, wherein said recombinant protein expressed by said vector is a PEDV S protein, and wherein said PEDV S protein preferably comprises or consists of an amino acid sequence being at least 70%, 80%, 85%, 90%, 91%, 92%, 93%, 94%, 95%, 96%, 97%, 98%, or 99% identical with the sequence of SEQ ID NO: 1 or SEQ ID NO:2.

34. The vaccine or pharmaceutical composition of any one of clauses 31 to 33, wherein said recombinant protein expressed by said vector is a PEDV S protein, and wherein said PEDV S protein preferably comprises or consists of an amino acid sequence being at least 70%, 80%, 85%, 90%, 91%, 92%, 93%, 94%, 95%, 96%, 97%, 98%, or 99% identical with the sequence of SEQ ID NO:16 or SEQ ID NO:17.

35. The vaccine or pharmaceutical composition of any one of clauses 31 to 34, comprising or consisting of
    a. the CDV vector of any one of clauses 1 to 12, and
    b. a recombinant protein expressed by said vector, wherein said recombinant protein comprises or consists of an amino acid sequence being comprising or consisting of an amino acid sequence being at least 70%, 80%, 85%, 90%, 91%, 92%, 93%, 94%, 95%, 96%, 97%, 98%, or 99% identical with the sequence of SEQ ID NO:1 or SEQ ID NO:2, and
    c. a pharmaceutical- or veterinary-acceptable carrier or excipient, preferably said carrier is suitable for oral, intradermal, intramuscular or intranasal application,
    d. and optionally an adjuvant.

36. The vaccine or pharmaceutical composition of any one of clauses 31 to 35, comprising or consisting of
    a. the CDV vector of any one of clauses 1 to 12, and
    b. a recombinant protein expressed by said vector, wherein said recombinant protein comprises or consists of an amino acid sequence being comprising or consisting of an amino acid sequence being at least 70%, 80%, 85%, 90%, 91%, 92%, 93%, 94%, 95%, 96%, 97%, 98%, or 99% identical with the sequence of SEQ ID NO:16 or SEQ ID NO:17, and
    c. a pharmaceutical- or veterinary-acceptable carrier or excipient, preferably said carrier is suitable for oral, intradermal, intramuscular or intranasal application,
    d. and optionally an adjuvant.

37. A method for the preparation of an immunogenic composition or a vaccine for reducing the incidence or the severity of one or more clinical signs associated with or caused by an infection, comprising the following steps:
    a. infecting a mammalian host cell with the vector according to any one of clauses 1 to 12,
    b. cultivating the infected cells under suitable conditions,
    c. collecting infected cell cultures,
    d. optionally purifying the collected infected cell cultures of step c),
    e. optionally mixing said collected infected cell culture with a pharmaceutically acceptable carrier.

38. The method according to clause 37, wherein said immunogenic composition or said vaccine reduces the severity of one or more clinical signs associated with or caused by an infection with a porcine epidemic diarrhea virus (PEDV).

39. The immunogenic composition according to any one of clauses 25 to 30 or the vaccine or pharmaceutical composition according to any one of clauses 31 to 36 for use in a method of reducing or preventing the clinical signs or disease caused by an infection with PEDV in an animal or for use in a method of treating or preventing an infection with PEDV in an animal, and wherein said animal is preferably a pig.

40. The immunogenic composition according to any one of clauses 25 to 30 or the vaccine or pharmaceutical composition according to any one of clauses 31 to 36 for use in a method for inducing an immune response against PEDV in a pig, in particular in a preferably pregnant sow.

41. The immunogenic composition according to any one of clauses 25 to 30 or the vaccine or pharmaceutical composition according to any one of clauses 31 to 36 for use in a method of reducing or preventing the clinical signs or disease caused by an infection with a PEDV in a piglet, wherein the piglet is to be suckled by a sow to which the immunogenic composition has been adminstered.

42. The immunogenic composition according to clause 41, wherein said sow to which the immunogenic composition has been administered is a sow to which the immunogenic composition has been administered while said sow has been pregnant, in particular with said piglet.

43. The immunogenic composition according to any one of clauses 25 to 30 or the vaccine or pharmaceutical composition according to any one of clauses 31 to 36 for use according to any of clauses 39 to 42, wherein said immunogenic composition or said vaccine or pharmaceutical composition is to be administered mucosally, preferably intranasally.

44. The immunogenic composition according to any one of clauses 25 to 30 or the vaccine or pharmaceutical composition according to any one of clauses 31 to 36 for use according to any one of clauses 40 to 43, wherein said immunogenic composition or said vaccine or pharmaceutical composition is to be administered mucosally, preferably intranasally, to said sow.

45. A method of immunizing a subject comprising administering to the subject an immunogenic composition according to any one of clauses 25 to 30 or a vaccine or pharmaceutical composition according to any one of clauses 31 to 36.

46. A method of immunizing swine against a clinical disease caused by at least one pathogen in said animal, said method comprising the step of administering to the animal the immunogenic composition according to any one of clauses 25 to 30 or the vaccine or pharmaceutical composition according to any one of clauses 31 to 36, wherein said immunogenic composition or vaccine fails to cause clinical signs of infection but is capable of inducing an immune response that immunizes the animal against pathogenic forms of said at least one pathogen.

47. The method of clause 46, wherein said at least one pathogen is PEDV.

48. A method for inducing the production of antibodies specific for PEDV in a sow, wherein said method comprises administering the immunogenic composition according to any one of clauses 25 to 30 or the vaccine or pharmaceutical composition according to any one of clauses 31 to 36 to said sow.

49. A method of reducing or preventing the clinical signs or disease caused by an infection with a PEDV in a piglet, wherein said method comprises
    administering the immunogenic composition according to any one of clauses 25 to 30 or the vaccine or pharmaceutical composition according to any one of clauses 31 to 36 to a sow, and
    allowing said piglet to be suckled by said sow.

50. The method of clause 49, wherein said sow is a sow being pregnant, in particular with said pig.

51. The method of clause 49 or 50, comprising the steps of administering the immunogenic composition according to any one of clauses 25 to 30 or the vaccine or pharmaceutical composition according to any one of clauses 31 to 36 to a sow being pregnant with said piglet, allowing said sow to give birth to said piglet, and allowing said piglet to be suckled by said sow.
52. A method of reducing the mortality caused by an infection with a PEDV in a piglet, wherein the piglet is to be suckled by a sow to which the immunogenic composition of any one of clauses 25 to 30 has been administered.
53. The method of any one of clauses 45 to 52, wherein said immunogenic composition or said vaccine or pharmaceutical composition is administered mucosally, preferably intranasally, to said sow.
54. The method of any one of clauses 45 to 53, wherein said immunogenic composition or said vaccine or pharmaceutical composition is administered twice to said sow.
55. The method of any one of clauses 45 to 54, wherein said immunogenic composition or said vaccine or pharmaceutical composition is administered twice mucosally, preferably twice intranasally, to said sow.
56. A kit for inducing an immune response against PEDV in a pig or for vaccinating a pig against a disease associated with and/or reducing the incidence or the severity of one or more clinical signs associated with or caused by PEDV in a pig, comprising:
   a) a syringe or a dispenser capable of administering a vaccine to said pig, in particular via the intranasal route; and
   b) the immunogenic composition according to any one of clauses 25 to 30 or the vaccine according to any one of clauses 31 to 36, and
   c) optionally an instruction leaflet.

SEQUENCES OVERVIEW

The following sequences are detailed and disclosed hereby in the present invention, wherein the nucleotide sequences in the sequence listing are presented in the 5'-end to 3'-end direction from left to right, and wherein:
SEQ ID NO:1 corresponds to an amino acid sequence of a PEDV S protein (derived from a genotype 2b PEDV),
SEQ ID NO:2 corresponds to an amino acid sequence of a PEDV S protein (derived from a genotype 2a PEDV),
SEQ ID NO:3 (RNA) corresponds to a sequence encoding a PEDV S protein (derived from a G2b PEDV),
SEQ ID NO:4 (RNA) corresponds to the sequence of SEQ ID NO. 3 with a further sequence for a second stop codon (in order to fulfill the "rule of six"),
SEQ ID NO:5 (RNA) corresponds to a sequence encoding a PEDV S protein (derived from a genotype 2a PEDV),
SEQ ID NO:6 (RNA) corresponds to an expression cassette comprising the sequence of SEQ ID NO:4,
SEQ ID NO:7 (RNA) corresponds to an expression cassette comprising the sequence of SEQ ID NO:4,
SEQ ID NO:8 (RNA) comprises the sequence of SEQ ID NO:6 and/or SEQ ID NO:7,
SEQ ID NO:9 (RNA) corresponds to a sequence comprising the M, F, H and L gene of a CDV,
SEQ ID NO:10 (RNA) corresponds to a sequence comprising the N and P gene of a CDV,
SEQ ID NO:11 corresponds to a DNA reverse complement of SEQ ID NO:3,
SEQ ID NO:12 corresponds to a DNA reverse complement of SEQ ID NO:4,
SEQ ID NO:13 corresponds to a DNA reverse complement of SEQ ID NO:8,
SEQ ID NO:14 corresponds to a DNA sequence comprising the sequence of SEQ ID NO: 13,
SEQ ID NO:15 corresponds to an amino acid sequence of a PEDV S protein encoded by SEQ ID NO:5,
SEQ ID NO:16 corresponds to an amino acid sequence of a PEDV S protein (derived from a genotype 2a PEDV),
SEQ ID NO:17 corresponds to an amino acid sequence of a PEDV S protein (derived from a genotype 2a PEDV),
SEQ ID NOs:18-21: probe, primer, and ultramer sequences (Table 2).

What is claimed is:

1. A canine distemper virus (CDV) vector comprising a heterologous nucleotide sequence of interest, wherein said heterologous nucleotide sequence of interest encodes a porcine epidemic diarrhea virus (PEDV) antigen wherein the PEDV antigen is a PEDV S protein.

2. The CDV vector of claim 1, wherein said PEDV S protein comprises or consists of an amino acid sequence being at least 99.8% identical with the sequence of SEQ ID NO:1 or 99.9% identical with the sequence of SEQ ID NO:2.

3. The CDV vector of claim 1, wherein the PEDV antigen is a PEDV S protein, and wherein said PEDV S protein comprises or consists of an amino acid sequence being at least 99.5% identical with the sequence of SEQ ID NO:16 or 99.2% identical with the sequence of SEQ ID NO:17.

4. The CDV vector of claim 1, wherein said heterologous nucleotide sequence of interest encodes a PEDV S protein, and wherein said heterologous nucleotide sequence of interest is an RNA sequence being at least 70%, 80%, 85%, 90%, 91%, 92%, 93%, 94%, 95%, 96%, 97%, 98%, or 99% identical with the sequence of any one of SEQ ID NOs:3 to 5.

5. The CDV vector of claim 1, wherein
said heterologous nucleotide sequence of interest is located between a P gene and an M gene of the CDV; or
said heterologous nucleotide sequence of interest is a heterologous RNA sequence of interest, and wherein said heterologous RNA sequence is operably linked to a gene start (GS) sequence located in 3'direction of said heterologous RNA sequence or to the genome promoter of the CDV.

6. The CDV vector of claim 1, comprising an RNA sequence being at least 70%, 80%, 85%, 90%, 91%, 92%, 93%, 94%, 95%, 96%, 97%, 98%, or 99% identical with the sequence of SEQ ID NO:6 or SEQ ID NO:7 or SEQ ID NO:8.

7. The CDV vector of claim 1 further comprising
an RNA sequence consisting of or comprising an RNA sequence being at least 70%, 80%, 85%, 90%, 91%, 92%, 93%, 94%, 95%, 96%, 97%, 98%, or 99% identical with the sequence of SEQ ID NO:9, and wherein said RNA sequence flanks the 5'end of the RNA sequence being at least 70%, 80%, 85%, 90%, 91%, 92%, 93%, 94%, 95%, 96%, 97%, 98%, or 99% identical with the sequence of SEQ ID NO:8, or
an RNA sequence consisting of or comprising an RNA sequence being at least 70%, 80%, 85%, 90%, 91%, 92%, 93%, 94%, 95%, 96%, 97%, 98%, or 99% identical with the sequence of SEQ ID NO:10, and wherein said RNA sequence flanks the 3' end of the RNA sequence being at least 70%, 80%, 85%, 90%, 91%, 92%, 93%, 94%, 95%, 96%, 97%, 98%, or 99% identical with the sequence of SEQ ID NO:8.

8. A nucleic acid molecule which encodes the CDV vector of claim 1, and wherein said nucleic acid molecule is a DNA molecule.

9. The DNA molecule of claim 8, wherein said molecule comprises a DNA sequence encoding a PEDV spike (S) protein, and wherein said sequence is a DNA sequence being at least 70%, 80%, 85%, 90%, 91%, 92%, 93%, 94%, 95%, 96%, 97%, 98%, or 99% identical with the sequence of SEQ ID NO:11 or SEQ ID NO:12.

10. The DNA molecule of claim 8, wherein said molecule comprises a DNA sequence being at least 70%, 80%, 85%, 90%, 91%, 92%, 93%, 94%, 95%, 96%, 97%, 98%, or 99% identical with the sequence of SEQ ID NO: 13 or SEQ ID NO:14.

11. A mammalian host cell containing the CDV vector of claim 1.

12. A vaccine comprising the CDV vector of claim 1.

13. A DNA construct expressing the CDV vector of claim 1.

14. An immunogenic composition comprising
the CDV vector according to claim 1, wherein said CDV vector is an infectious or an attenuated or a modified live virus, and
wherein said immunogenic composition further comprises a pharmaceutical- or veterinary-acceptable carrier or excipient, wherein said carrier is suitable for oral, intradermal, intramuscular or intranasal application.

15. A kit for inducing an immune response against PEDV in a pig or for vaccinating a pig against a disease associated with or reducing the incidence or the severity of one or more clinical signs associated with or caused by PEDV in a pig, comprising:
a) a syringe or a dispenser capable of administering a vaccine to said pig; and
b) the immunogenic composition according to claim 14.

16. A method for inducing an immune response against PEDV in a pig or pregnant sow by administering the immunogenic composition of claim 14 to said pig or said pregnant sow.

17. An immunogenic composition comprising
the CDV vector according to claim 1, wherein said CDV vector encodes a PEDV S protein comprising or consisting of an amino acid sequence being at least 99.8% identical with the sequence of SEQ ID NO:1 or 99.9% identical with the sequence of SEQ ID NO:2 or 99.5% identical with the sequence of SEQ ID NO:16 or 99.2% identical with the sequence of SEQ ID NO:17, and
wherein said immunogenic composition further comprises a pharmaceutical- or veterinary-acceptable carrier or excipient, wherein said carrier is suitable for oral, intradermal, intramuscular or intranasal application.

18. A method for inducing an immune response against PEDV in a pig or pregnant sow by administering the CDV vector of claim 1 to said pig or said pregnant sow.

19. The method of claim 18 wherein the CDV vector is administered mucosally or intranasally to said pig or said pregnant sow.

20. A method for preparing an immunogenic composition or a vaccine for reducing the incidence or the severity of one or more clinical signs associated with or caused by a PEDV infection, comprising the following steps:
a) infecting a mammalian host cell with the CDV vector according to claim 1,
b) cultivating the infected cells under suitable conditions for producing infected cell cultures, and
c) collecting the infected cell cultures, and
d) optionally purifying the collected infected cell cultures of step c), and
e) optionally mixing the said collected infected cell cultures with a pharmaceutically acceptable carrier.

* * * * *

SEQUENCE LISTING

```
<160> NUMBER OF SEQ ID NOS: 21

<210> SEQ ID NO 1
<211> LENGTH: 1383
<212> TYPE: PRT
<213> ORGANISM: porcine epidemic diarrhea virus

<400> SEQUENCE: 1

Met Lys Ser Leu Asn Tyr Phe Trp Leu Phe Leu Pro Val Leu Ser Thr
1               5                   10                  15

Leu Ser Leu Pro Gln Asp Val Thr Arg Cys Gln Ser Thr Ile Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ser Met Asn Ser Ser Ser Trp Tyr Cys Gly
    50                  55                  60

Thr Gly Leu Glu Thr Ala Ser Gly Val His Gly Ile Phe Leu Ser Tyr
65                  70                  75                  80

Ile Asp Ala Gly Gln Gly Phe Glu Ile Gly Ile Ser Gln Glu Pro Phe
                85                  90                  95

Asp Pro Ser Gly Tyr Gln Leu Tyr Leu His Lys Ala Thr Asn Gly Asn
```

```
            100                 105                 110
His Asn Ala Ile Ala Arg Leu Arg Ile Cys Gln Phe Pro Asn Asn Lys
        115                 120                 125

Thr Leu Gly Pro Thr Val Asn Asp Val Thr Gly Arg Asn Cys Leu
130                 135                 140

Phe Asn Lys Ala Ile Pro Ala Tyr Met Gln Asp Gly Lys Asn Ile Val
145                 150                 155                 160

Val Gly Ile Thr Trp Asp Asn Asp Arg Val Thr Val Phe Ala Asp Lys
                165                 170                 175

Ile Tyr His Phe Tyr Leu Lys Asn Asp Trp Ser Arg Val Ala Thr Arg
            180                 185                 190

Cys Tyr Asn Lys Arg Ser Cys Ala Met Gln Tyr Val Tyr Thr Pro Thr
        195                 200                 205

Tyr Tyr Met Leu Asn Val Thr Ser Ala Gly Glu Asp Gly Ile Tyr Tyr
    210                 215                 220

Glu Pro Cys Thr Ala Asn Cys Ser Gly Tyr Ala Val Asn Val Phe Ala
225                 230                 235                 240

Thr Asp Ser Asn Gly His Ile Pro Glu Gly Phe Ser Phe Asn Asn Trp
                245                 250                 255

Phe Leu Leu Ser Asn Asp Ser Thr Leu Leu His Gly Lys Val Val Ser
            260                 265                 270

Asn Gln Pro Leu Leu Val Asn Cys Leu Leu Ala Ile Pro Lys Ile Tyr
        275                 280                 285

Gly Leu Gly Gln Phe Phe Ser Phe Asn Gln Thr Met Asp Gly Val Cys
    290                 295                 300

Asn Gly Ala Ala Ala Gln Arg Ala Pro Glu Ala Leu Arg Phe Asn Ile
305                 310                 315                 320

Asn Asp Thr Ser Val Ile Leu Ala Glu Gly Ser Ile Val Leu His Thr
                325                 330                 335

Ala Leu Gly Thr Asn Leu Ser Phe Val Cys Ser Asn Ser Ser Asp Pro
            340                 345                 350

His Leu Ala Thr Phe Thr Ile Pro Leu Gly Ala Thr Gln Val Pro Tyr
        355                 360                 365

Tyr Cys Phe Leu Lys Val Asp Thr Tyr Asn Ser Asn Val Tyr Lys Phe
    370                 375                 380

Leu Ala Val Leu Pro Pro Thr Val Arg Glu Ile Val Ile Thr Lys Tyr
385                 390                 395                 400

Gly Asp Val Tyr Val Asn Gly Phe Gly Tyr Leu His Leu Gly Leu Leu
                405                 410                 415

Asp Ala Val Thr Ile Asn Phe Thr Gly His Gly Thr Asp Asp Asp Val
            420                 425                 430

Ser Gly Phe Trp Thr Ile Ala Ser Thr Asn Phe Val Asp Ala Leu Ile
        435                 440                 445

Glu Val Gln Gly Thr Ala Ile Gln Arg Ile Leu Tyr Cys Asp Asp Pro
    450                 455                 460

Val Ser Gln Leu Lys Cys Ser Gln Val Ala Phe Asp Leu Asp Asp Gly
465                 470                 475                 480

Phe Tyr Pro Ile Ser Ser Arg Asn Leu Leu Ser His Glu Gln Pro Ile
                485                 490                 495

Ser Phe Val Thr Leu Pro Ser Phe Asn Asp His Ser Phe Val Asn Ile
            500                 505                 510

Thr Val Ser Ala Ser Phe Gly Gly His Ser Gly Ala Asn Leu Ile Ala
        515                 520                 525
```

-continued

Ser Asp Thr Thr Ile Asn Gly Phe Ser Ser Phe Cys Val Asp Thr Arg
        530                 535                 540

Gln Phe Thr Ile Ser Leu Phe Tyr Asn Val Thr Asn Ser Tyr Gly Tyr
545                 550                 555                 560

Val Ser Lys Ser Gln Asp Ser Asn Cys Pro Phe Thr Leu Gln Ser Val
                565                 570                 575

Asn Asp Tyr Leu Ser Phe Ser Lys Phe Cys Val Ser Thr Ser Leu Leu
            580                 585                 590

Ala Ser Ala Cys Thr Ile Asp Leu Phe Gly Tyr Pro Glu Phe Gly Ser
        595                 600                 605

Gly Val Lys Phe Thr Ser Leu Tyr Phe Gln Phe Thr Glu Gly Glu Leu
    610                 615                 620

Ile Thr Gly Thr Pro Lys Pro Leu Glu Gly Val Thr Asp Val Ser Phe
625                 630                 635                 640

Met Thr Leu Asp Val Cys Thr Lys Tyr Thr Ile Tyr Gly Phe Lys Gly
                645                 650                 655

Glu Gly Ile Ile Thr Leu Thr Asn Ser Ser Phe Leu Ala Gly Val Tyr
            660                 665                 670

Tyr Thr Ser Asp Ser Gly Gln Leu Leu Ala Phe Lys Asn Val Thr Ser
        675                 680                 685

Gly Ala Val Tyr Ser Val Thr Pro Cys Ser Phe Ser Glu Gln Ala Ala
    690                 695                 700

Tyr Val Asp Asp Asp Ile Val Gly Val Ile Ser Ser Leu Ser Ser Ser
705                 710                 715                 720

Thr Phe Asn Ser Thr Arg Glu Leu Pro Gly Phe Phe Tyr His Ser Asn
                725                 730                 735

Asp Gly Ser Asn Cys Thr Glu Pro Val Leu Val Tyr Ser Asn Ile Gly
            740                 745                 750

Val Cys Lys Ser Gly Ser Ile Gly Tyr Val Pro Ser Gln Ser Gly Gln
        755                 760                 765

Val Lys Ile Ala Pro Thr Val Thr Gly Asn Ile Ser Ile Pro Thr Asn
    770                 775                 780

Phe Ser Met Ser Ile Arg Thr Glu Tyr Leu Gln Leu Tyr Asn Thr Pro
785                 790                 795                 800

Val Ser Val Asp Cys Ala Thr Tyr Val Cys Asn Gly Asn Ser Arg Cys
                805                 810                 815

Lys Gln Leu Leu Thr Gln Tyr Thr Ala Ala Cys Lys Thr Ile Glu Ser
            820                 825                 830

Ala Leu Gln Leu Ser Ala Arg Leu Glu Ser Val Glu Val Asn Ser Met
        835                 840                 845

Leu Thr Ile Ser Glu Glu Ala Leu Gln Leu Ala Thr Ile Ser Ser Phe
850                 855                 860

Asn Gly Asp Gly Tyr Asn Phe Thr Asn Val Leu Gly Val Ser Val Tyr
865                 870                 875                 880

Asp Pro Ala Ser Gly Arg Val Val Gln Lys Arg Ser Phe Ile Glu Asp
                885                 890                 895

Leu Leu Phe Asn Lys Val Val Thr Asn Gly Leu Gly Thr Val Asp Glu
            900                 905                 910

Asp Tyr Lys Arg Cys Ser Asn Gly Arg Ser Val Ala Asp Leu Val Cys
        915                 920                 925

Ala Gln Tyr Tyr Ser Gly Val Met Val Leu Pro Gly Val Val Asp Ala
    930                 935                 940

-continued

```
Glu Lys Leu His Met Tyr Ser Ala Ser Leu Ile Gly Gly Met Val Leu
945                 950                 955                 960

Gly Gly Phe Thr Ser Ala Ala Ala Leu Pro Phe Ser Tyr Ala Val Gln
            965                 970                 975

Ala Arg Leu Asn Tyr Leu Ala Leu Gln Thr Asp Val Leu Gln Arg Asn
        980                 985                 990

Gln Gln Leu Leu Ala Glu Ser Phe Asn Ser Ala Ile Gly Asn Ile Thr
    995                 1000                1005

Ser Ala Phe Glu Ser Val Lys Glu Ala Ile Ser Gln Thr Ser Lys
    1010                1015                1020

Gly Leu Asn Thr Val Ala His Ala Leu Thr Lys Val Gln Glu Val
    1025                1030                1035

Val Asn Ser Gln Gly Ala Ala Leu Thr Gln Leu Thr Val Gln Leu
    1040                1045                1050

Gln His Asn Phe Gln Ala Ile Ser Ser Ser Ile Asp Asp Ile Tyr
    1055                1060                1065

Ser Arg Leu Asp Ile Leu Ser Ala Asp Val Gln Val Asp Arg Leu
    1070                1075                1080

Ile Thr Gly Arg Leu Ser Ala Leu Asn Ala Phe Val Ala Gln Thr
    1085                1090                1095

Leu Thr Lys Tyr Thr Glu Val Gln Ala Ser Arg Lys Leu Ala Gln
    1100                1105                1110

Gln Lys Val Asn Glu Cys Val Lys Ser Gln Ser Gln Arg Tyr Gly
    1115                1120                1125

Phe Cys Gly Gly Asp Gly Glu His Ile Phe Ser Leu Val Gln Ala
    1130                1135                1140

Ala Pro Gln Gly Leu Leu Phe Leu His Thr Val Leu Val Pro Gly
    1145                1150                1155

Asp Phe Ile Asp Val Ile Ala Ile Ala Gly Leu Cys Val Asn Asp
    1160                1165                1170

Glu Ile Ala Leu Thr Leu Arg Glu Pro Gly Leu Val Leu Phe Thr
    1175                1180                1185

His Glu Leu Gln Asn His Thr Ala Thr Glu Tyr Phe Val Ser Ser
    1190                1195                1200

Arg Arg Met Phe Glu Pro Arg Lys Pro Thr Val Ser Asp Phe Val
    1205                1210                1215

Gln Ile Glu Ser Cys Val Val Thr Tyr Val Asn Leu Thr Arg Asp
    1220                1225                1230

Gln Leu Pro Asp Val Ile Pro Asp Tyr Ile Asp Val Asn Lys Thr
    1235                1240                1245

Leu Asp Glu Ile Leu Ala Ser Leu Pro Asn Arg Thr Gly Pro Ser
    1250                1255                1260

Leu Pro Leu Asp Val Phe Asn Ala Thr Tyr Leu Asn Leu Thr Gly
    1265                1270                1275

Glu Ile Ala Asp Leu Glu Gln Arg Ser Glu Ser Leu Arg Asn Thr
    1280                1285                1290

Thr Glu Glu Leu Gln Ser Leu Ile Tyr Asn Ile Asn Asn Thr Leu
    1295                1300                1305

Val Asp Leu Glu Trp Leu Asn Arg Val Glu Thr Tyr Ile Lys Trp
    1310                1315                1320

Pro Trp Trp Val Trp Leu Ile Val Phe Ile Val Leu Ile Phe Val
    1325                1330                1335

Val Ser Leu Leu Val Phe Cys Cys Ile Ser Thr Gly Cys Cys Gly
```

```
              1340                1345                1350
Cys  Cys  Gly  Cys  Cys  Cys  Ala  Cys  Phe  Ser  Gly  Cys  Cys  Arg  Gly
         1355                1360                1365

Pro  Arg  Leu  Gln  Pro  Tyr  Glu  Val  Phe  Glu  Lys  Val  His  Val  Gln
    1370                1375                1380

<210> SEQ ID NO 2
<211> LENGTH: 1388
<212> TYPE: PRT
<213> ORGANISM: porcine epidemic diarrhea virus

<400> SEQUENCE: 2

Met  Lys  Ser  Leu  Thr  Tyr  Phe  Trp  Leu  Phe  Leu  Pro  Val  Leu  Ser  Thr
 1                5                    10                   15

Leu  Ser  Leu  Pro  Gln  Asp  Val  Thr  Arg  Cys  Ser  Ala  Asn  Thr  Asn  Phe
             20                    25                   30

Arg  Arg  Phe  Phe  Ser  Lys  Phe  Asn  Val  Gln  Ala  Pro  Ala  Val  Val  Val
             35                    40                   45

Leu  Gly  Gly  Tyr  Leu  Pro  Ile  Gly  Glu  Asn  Gln  Gly  Val  Asn  Ser  Thr
     50                    55                   60

Trp  Tyr  Cys  Ala  Gly  Gln  His  Pro  Thr  Ala  Ser  Gly  Val  His  Gly  Ile
65                    70                   75                        80

Phe  Val  Ser  His  Ile  Arg  Gly  Gly  His  Gly  Phe  Glu  Ile  Gly  Ile  Ser
                 85                    90                   95

Gln  Glu  Pro  Phe  Asp  Pro  Ser  Gly  Tyr  Gln  Leu  Tyr  Leu  His  Lys  Ala
             100                   105                  110

Thr  Asn  Gly  Asn  Thr  Asn  Ala  Thr  Ala  Arg  Leu  Arg  Ile  Cys  Gln  Phe
             115                   120                  125

Pro  Ser  Ile  Lys  Thr  Leu  Gly  Pro  Thr  Ala  Asn  Asn  Asp  Val  Thr  Thr
    130                   135                  140

Gly  Arg  Asn  Cys  Leu  Phe  Asn  Lys  Ala  Ile  Pro  Ala  His  Met  Ser  Glu
145                   150                   155                       160

His  Ser  Val  Val  Gly  Ile  Thr  Trp  Asp  Asn  Asp  Arg  Val  Thr  Val  Phe
                 165                   170                  175

Ser  Asp  Lys  Ile  Tyr  Tyr  Phe  Tyr  Phe  Lys  Asn  Asp  Trp  Ser  Arg  Val
             180                   185                  190

Ala  Thr  Lys  Cys  Tyr  Asn  Ser  Gly  Gly  Cys  Ala  Met  Gln  Tyr  Val  Tyr
             195                   200                  205

Glu  Pro  Thr  Tyr  Tyr  Met  Leu  Asn  Val  Thr  Ser  Ala  Gly  Glu  Asp  Gly
    210                   215                  220

Ile  Ser  Tyr  Gln  Pro  Cys  Thr  Ala  Asn  Cys  Ile  Gly  Tyr  Ala  Ala  Asn
225                   230                   235                       240

Val  Phe  Ala  Thr  Glu  Pro  Asn  Gly  His  Ile  Pro  Glu  Gly  Phe  Ser  Phe
                 245                   250                  255

Asn  Asn  Trp  Phe  Leu  Leu  Ser  Asn  Asp  Ser  Thr  Leu  Val  His  Gly  Lys
             260                   265                  270

Val  Val  Ser  Asn  Gln  Pro  Leu  Leu  Val  Asn  Cys  Leu  Leu  Ala  Ile  Pro
             275                   280                  285

Lys  Ile  Tyr  Gly  Leu  Gly  Gln  Phe  Phe  Ser  Phe  Asn  Gln  Thr  Ile  Asp
    290                   295                  300

Gly  Val  Cys  Asn  Gly  Ala  Ala  Val  Gln  Arg  Ala  Pro  Glu  Ala  Leu  Arg
305                   310                   315                       320

Phe  Asn  Ile  Asn  Asp  Thr  Ser  Val  Ile  Leu  Ala  Glu  Gly  Ser  Ile  Val
                 325                   330                  335
```

```
Leu His Thr Ala Leu Gly Thr Asn Phe Ser Phe Val Cys Ser Asn Ser
                340                 345                 350

Ser Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
            405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
            435                 440                 445

Ala Leu Ile Glu Val Gln Gly Thr Ala Ile Gln Arg Ile Leu Tyr Cys
        450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
            515                 520                 525

Leu Ile Ala Ser Asp Thr Thr Ile Asn Gly Phe Ser Ser Phe Cys Val
        530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
            660                 665                 670

Gly Val Tyr Tyr Thr Ser Asp Ser Gly Gln Leu Leu Ala Phe Lys Asn
        675                 680                 685

Val Thr Ser Gly Ala Val Tyr Ser Val Thr Pro Cys Ser Phe Ser Glu
    690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
```

```
            755                 760                 765
Ser Gly Gln Val Lys Ile Ala Pro Thr Val Thr Gly Asn Ile Ser Ile
770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
                820                 825                 830

Ile Glu Ser Ala Leu Gln Leu Ser Ala Arg Leu Glu Ser Val Glu Val
                835                 840                 845

Asn Ser Met Leu Thr Ile Ser Glu Glu Ala Leu Gln Leu Ala Thr Ile
850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Leu Leu Phe Asn Lys Val Val Thr Asn Gly Leu Gly Thr
                900                 905                 910

Val Asp Glu Asp Tyr Lys Arg Cys Ser Asn Gly Arg Ser Val Ala Asp
                915                 920                 925

Leu Val Cys Ala Gln Tyr Tyr Ser Gly Val Met Val Leu Pro Gly Val
930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
                980                 985                 990

Gln Arg Asn Gln Gln Leu Leu Ala Glu Ser Phe Asn Ser Ala Ile Gly
                995                 1000                1005

Asn Ile Thr Ser Ala Phe Glu Ser Val Lys Glu Ala Ile Ser Gln
        1010                1015                1020

Thr Ser Lys Gly Leu Asn Thr Val Ala His Ala Leu Thr Lys Val
        1025                1030                1035

Gln Glu Val Val Asn Ser Gln Gly Ala Ala Leu Thr Gln Leu Thr
        1040                1045                1050

Val Gln Leu Gln His Asn Phe Gln Ala Ile Ser Ser Ser Ile Asp
        1055                1060                1065

Asp Ile Tyr Ser Arg Leu Asp Ile Leu Ser Ala Asp Val Gln Val
        1070                1075                1080

Asp Arg Leu Ile Thr Gly Arg Leu Ser Ala Leu Asn Ala Phe Val
        1085                1090                1095

Ala Gln Thr Leu Thr Lys Tyr Thr Glu Val Gln Ala Ser Arg Lys
        1100                1105                1110

Leu Ala Gln Gln Lys Val Asn Glu Cys Val Lys Ser Gln Ser Gln
        1115                1120                1125

Arg Tyr Gly Phe Cys Gly Gly Asp Gly Glu His Ile Phe Ser Leu
        1130                1135                1140

Val Gln Ala Ala Pro Gln Gly Leu Leu Phe Leu His Thr Val Leu
        1145                1150                1155

Val Pro Ser Asp Phe Val Asp Val Ile Ala Ile Ala Gly Leu Cys
        1160                1165                1170
```

```
Val Asn  Asp Glu Ile Ala Leu  Thr Leu Arg Glu Pro  Gly Leu Val
    1175                 1180                 1185

Leu Phe  Thr His Glu Leu Gln  Asn His Thr Ala Thr  Glu Tyr Phe
    1190                 1195                 1200

Val Ser  Ser Arg Arg Met Phe  Glu Pro Arg Lys Pro  Thr Val Ser
    1205                 1210                 1215

Asp Phe  Val Gln Ile Glu Ser  Cys Val Val Thr Tyr  Val Asn Leu
    1220                 1225                 1230

Thr Arg  Asp Gln Leu Pro Asp  Val Ile Pro Asp Tyr  Ile Asp Val
    1235                 1240                 1245

Asn Lys  Thr Leu Asp Glu Ile  Leu Ala Ser Leu Pro  Asn Arg Thr
    1250                 1255                 1260

Gly Pro  Ser Leu Pro Leu Asp  Val Phe Asn Ala Thr  Tyr Leu Asn
    1265                 1270                 1275

Leu Thr  Gly Glu Ile Ala Asp  Leu Glu Gln Arg Ser  Glu Ser Leu
    1280                 1285                 1290

Arg Asn  Thr Thr Glu Glu Leu  Gln Ser Leu Ile Tyr  Asn Ile Asn
    1295                 1300                 1305

Asn Thr  Leu Val Asp Leu Glu  Trp Leu Asn Arg Val  Glu Thr Tyr
    1310                 1315                 1320

Ile Lys  Trp Pro Trp Trp Val  Trp Leu Ile Ile Phe  Ile Val Leu
    1325                 1330                 1335

Ile Phe  Val Val Ser Leu Leu  Val Phe Cys Cys Ile  Ser Thr Gly
    1340                 1345                 1350

Cys Cys  Gly Cys Cys Gly Cys  Cys Cys Ala Cys Phe  Ser Gly Cys
    1355                 1360                 1365

Cys Arg  Gly Pro Arg Leu Gln  Pro Tyr Glu Val Phe  Glu Lys Val
    1370                 1375                 1380

His Val  Gln Cys Gly
    1385
```

<210> SEQ ID NO 3
<211> LENGTH: 4152
<212> TYPE: RNA
<213> ORGANISM: Artificial Sequence
<220> FEATURE:
<223> OTHER INFORMATION: encodes a PEDV S protein

<400> SEQUENCE: 3

```
ucacugcacu cucacuuucu caaacaccuc agcgggcugg agccggggguc cucuacagca     60 gccgcugaag caggcgcagc agcagccgca gcagccgcag cagccggugg agaugcagca    120
gaacaccagc agggacacca cgaagaucag cacgaugaac acgaucagcc acacccacca    180
uggccacuug auguaggucu ccacucuguu cagccacucc agguccacca ggguguuguu    240
gauguuguag aucagggacu gcagcuccuc gguggguguuu cucagggacu cgcuucucug    300
cuccaggucg gcgaucucgc cggucagguu cagguaggug gcguugaaca cguccagggg    360
caggcugggg ccgguucugu uuggcaggga ggccaggauc ucguccaggg ucuuguucac    420
gucgauguag ucugggauca cgucuggcag cuggucucug gucagguuca cguaggucac    480
cacgcaggac ucgaucugca cgaagucgcu cacgguggc uuucuuggcu cgaacauccg    540
ucuggagcuc acgaaauacu cgguggcggu gugguucugc agcucguggg ugaacagcac    600
caggccgggc ucucucaggg ucagggcgau cucgucguuc acgcacaggc cggcgauggc    660
gaucacgucg augaagucgc cuggcaccag cacggugugc aggaacagca ggcccugugg    720
```

```
ggcggccugc accagggaga agaugugcuc gccgucgccg ccgcagaagc cguaucucug      780
gcucugggac uucacgcacu cguuccaccuu cugcuggcc agcuuucugg aggccugcac     840
cucgguguac uuggcagggu ucugggccac gaaggcguuc agggcggaca gucugccggu    900
gaucagucug uccaccugca cgucggcgga caggaugucc agccuggagu agaugucguc    960
gauggagcug agauggccu ggaaguugug cugcagcugc acggucagcu gggucagggc    1020
ggcgcccugg gaguucacca ccuccugcac cuuggcaggg cguggggcca cgguguucag    1080
gcccuuggag gucuggcuga uggccuccuu cacgcucucg aaggcggagg ugauguugcc    1140
gauggcgcug uugaagcucu cggccagcag cugcugguuu cucugcagca cgucggucug    1200
cagggccagg uaguucaguc uggccugcac ggcguagcug aagggcaggg cggcggcgga    1260
ggugaagccg cccagcacca ugccgccgau cagggaggcg cuguacaugu gcagcuucuc    1320
ggcguccacc acgccuggca gcaccaucac gccgcuguaa uacugggcgc acaccagguc    1380
ggccacggau cugccguugc ugcaucucuu guagaccucg uccacggugc caggccguu     1440 ggucaccacc uuguugaagg cggcguccuc gaugaagcuc cucuucugca ccacucugcc    1500
gcuggcuggg ucguacacgc ucacgcccag cacguugguu aaguuguagc cgucgccguu    1560
gaaggagcug aggugggcca gcugcagggc cuccucggag augguagca ugcuguucac    1620 cuccacggac uccagccugg cgcucagcug cagggcgcuc ucgauggucu ugcaggcggc    1680
ggguacuggg gucagcagcu gcuugcaucu ggaguugccg uugcacacgu aggugcgca     1740 guccacggac acggggugu uguacagcug cagguacucg guucugaugc ucauggagaa    1800
guuggugggg auggagaugu ugccggucac gguggggcg aucuucaccu ggccgcucug     1860 ggaguggcacg uagccgaugg agccgcucuu gcacacgccg auguuggagu acaccagcac    1920
uggcucggug caguuggagc cgucguugcu ggguagaaag aagccuggca gcucucuggu    1980
ggaguugaag gugcuggagg acaggcugga gaucacgccc acgaugucgu cguccacgua    2040
ggcggccugc ucgcugaagg agcaggggu cacgcuguac acggcgccgg aggucacguu     2100
cuugaaggcc agcagcuggc cgcugucgga gguguaguac acgccggcca ggaaggagcu    2160
guuggucagg gugaugaugc ccucgcccuu gaagccguag auggugacu uggugcacac     2220 guccagggue augaagcuca cgucggcac gcccuccagg ggcuuugggg uccggugau     2280 cagcucgccc ucgugaacu ggaaguacag gcugguugaac uucacgccgg agccgaacuc    2340
uggguagccg aacaggucga uggugcaggc gcuggccagc aggcugugg acacgcagaa    2400 cuugcugaag acagguaggu cguucacggg cugcagggu aaggggcagu ugagguccug    2460
gcucuugcuc acguagccgu agcuguuggu cacguuguag aacaggcuga uggugaacug    2520 ccugguguce acgcagaagc uggagaagcc guugauggug gugucggagg cgaucagguu    2580
ggcgccggag uggccgccga aggaggcgcu cacgugaug uucacgaagg aguggucguu     2640
gaaggauggc aggucacga agcugauugg cugcucgugg ucagcaggu uucuggagcu    2700 gauggggauag aagccgucgu ccaggucgaa ggccaccugg cugcacuuca gcuggacac    2760 uggugucucg caguacagga ugcgcuggau ggcggugccc ugcaccucga ucagggcguc    2820
cacgaaguug gugaggcga uggccagaa gccgcucacg ucgucgucgg ugccggugcc    2880
ggugaaguug auggucacgg cguccagcag gcccaggugc agguagccga agccguucac    2940
guacacgucg ccguacuugg ugaucacgau cucucacg gugguggca gcacggccag     3000 gaacuuguac acguugcugu uguaggguguc caccuucagg aagcaguagu auggcaccug    3060
```

| | |
|---|---|
| gguggcgccc aguggggaugg ugaagguggc caggugggggg ucggagcugu uggagcacac | 3120 |
| gaagcucagg uugguggccca gggcggugug cagcacgaug cugcccucgg ccaggaucac | 3180 |
| ggaggugucg uugauguuga aucucagggc cucuggggcc cucugggcgg cggcgccguu | 3240 |
| gcacacgccg uccauggucu gguugaagcu gaagaacugg cccaggccgu agaucuuugg | 3300 |
| gauggccagc aggcaguuca ccagcagugg cugguuggac accaccuugc cgugcagcag | 3360 |
| gguggagucg uugcucagca ggaaccaguu guugaaggag aagcccucgg ggaugguggcc | 3420 |
| guugcugucg guggcgaaca cguucacggc guagccgcug caguuggcgg ugcagggcuc | 3480 |
| guaguagaug ccguccucgc cggcgcuggu cacguucagc auguaguagg uuggggugua | 3540 |
| cacguacugc auggcgcagc uccgcuuguu guagcaccug guggccacuc uggaccaguc | 3600 |
| guucuucagg uagaaguggu agaucuuguc ggcgaacacg ucacucugu cguugucccca | 3660 |
| ggugaugccc accacgaugu ucuugccguc cugcauguag cugggauggg ccuuguugaa | 3720 |
| caggcaguuu cugccggugg ucacgucguu cacggugggg cccagggucu uguuguuggg | 3780 |
| gaacuggcag auucucagcc uggcgauggc guuguggguu ccguuggugg ccuugugcag | 3840 |
| guacagcugg uagccgcuug ggucgaaggg cuccuggcug augccgaucu cgaagcccug | 3900 |
| gccggcgucg auguagcuca ggaagaugcc gugcacgccg gaggcggucu ccaggccggu | 3960 |
| gccgcaguac caggagcugg aguucaugcu uggcagguag ccgcccagca ccaccacggc | 4020 |
| gggggccugc acguugaacu uggagaagaa ccgucugaag uugauugugg acuggcaucu | 4080 |
| ugugacaucc ugagggaggc ugagggugga gagcacgggg aggaagagcc agaaguaguu | 4140 |
| gagggauuuc au | 4152 |

<210> SEQ ID NO 4
<211> LENGTH: 4155
<212> TYPE: RNA
<213> ORGANISM: Artificial Sequence
<220> FEATURE:
<223> OTHER INFORMATION: encodes a PEDV S protein

<400> SEQUENCE: 4

| | |
|---|---|
| uuaucacugc acucucacuu ucucaaacac cucagcgggc uggagccggg guccucuaca | 60 |
| gcagccgcug aagcaggcgc agcagcagcc gcagcagccg cagcagccgg uggagaugca | 120 |
| gcagaacacc agcagggaca ccacgaagau cagcacgaug aacacagauca gccacaccca | 180 |
| ccauggccac uugauguagg ucuccacucu guucagccac uccaggucca ccagggugcu | 240 |
| guugauguug uagaucaggg acugcagcuc cucggugggu uucucaggg acucgcuucu | 300 |
| cugcuccagg ucggcgaucu cgccggucag guucagguag guggcguuga acacguccag | 360 |
| gggcaggcug gggccgguuc uguuuggcag ggaggccagg aucugucca gggucuuguu | 420 |
| cacgucgaug uagucuggga ucacgucugg cagcuggucu gggucagggu ucacguaggu | 480 |
| caccacgcag gacucgaucu gcacgaaguc gcucacgguug ggcuuucuug gcucgaacau | 540 |
| ccgucuggag cucacgaaau acucggggcc ggugugguuc ugcagcucgu ggugugaacag | 600 |
| caccaggccg ggcucucuca gggucagggc gaucugucg uucacgcaca ggccggcgau | 660 |
| ggcgaucacg ucgaugaagu cgccuggcac cagcacggug ugcaggaaca gcaggcccug | 720 |
| ugggggcggcc ugcaccaggg agaagaugug cucgccgucg ccgccgcaga agccguaucu | 780 |
| cuggcucugg gacucacgc acucguucac cuucugcugg gccagcuuuc uggaggccug | 840 |
| caccucggug uacuuggucca gggucuggcc cacgaaggcg uucaggggcgg acagucugcc | 900 |
| ggugaucagu cugucccaccu gcacgucggc ggacaggaug uccagccugg aguagaugue | 960 |

```
gucgauggag cuggagaugg ccuggaaguu gugcugcagc ugcacgguca gcuggucag    1020 ggcggcgccc ugggaguuca ccaccuccug caccuugguc agggcguggg ccacggucuu   1080
caggcccuug gaggucuggc ugauggccuc cuucacgcuc ucgaaggcgg aggugauguu   1140
gccgauggcg cuguugaagc ucucggcag cagcugcugg uuucucugca gcacgucggu   1200
cugcagggcc agguaguuca gucuggccug cacggcguag cugaagggca gggcggcggc   1260
ggaggugaag ccgcccagca ccaugccgcc gaucagggag gcgcuguaca ugugcagcuu   1320
cucggcgucc accacgccug gcagcaccau cacgccgcug uaauacuggg cgcacaccag   1380
gucggccacg gaucugccgu ugcugcaucu cuuguagucc ucguccacgg ugcccaggcc   1440
guugguacac accuuguuga aggcggcguc ucgaugaag cuccucuucu gcaccacucu    1500
gccgcuggcu gggucuaca cgcucacgcc agcacguugu gugaaguugu agccgucgcc   1560
guugaaggag cugaugguag ccagcugcag ggccuccucg gagaugguca gcaugcuguu   1620
caccuccacg gacuccagcc uggcgcucag cugcagggcg cucucgaugg ucuucaggc    1680 ggcgguguac uggucagca gcugcuugca ucuggaguug ccguugcaca cguaggugc    1740 gcaguccacg gacacggggg uguuguacag cugcagguac ucggucuga ugcucaugga    1800 gaaguuggug gggauggaga guugccggu cacggugggg gcgaucuuca ccuggccgcu    1860
cugggauggc acguagccga uggagccgcu cuugcacacg ccgauguugg aguacaccag   1920
cacuggcucg gugcaguugg agccgucguu gcuguggauag aagaagccug gcagcucucu   1980
gguggaguug aaggucugg aggacaggcu ggagaucacg cccacgaugu cgucguccac    2040
guaggcggcc ugcucgcuga aggagcaggg ggucacgcug uacacggcgc cggaggucac    2100
guucuugaag gcagcagcu ggccgcugu ggaggugua uacaccggg ccaggagga       2160 gcuguuggc agggugauga ugcccucgcc uugaagccg uagauggugu acuugugca     2220 caguccagg gucaugaagc ucacgucggu cacgccuccc aggggcuuug ggugccggu    2280 gaucagcucg cccucgguga acuggaagua caggcuggug aacuucacgc cggagccgaa   2340
cucuggguag ccgaacaggu cgauggugca ggcgcuggcc agcaggcugg uggacacgca    2400
gaacuugcug aaggacaggu agucguucac ggacugcagg gugaaggggc aguuggaguc    2460
cuggcucuug cucacguagc cguagcuguu ggcacguug uagaacaggc ugauggugaa    2520
cugccuggug uccacgcaga agcuggagaa gccguugaug gugucgg aggcgaucag      2580 guuggcgccg gaguggccgc cgaaggaggc gcucacggug auguucacga aggaguggc    2640 guugaaggau ggcaggguca cgaagcugau uggcugcucg uggcucagca gguucugga    2700 gcugauggg uagaagccgu cguccagguc gaaggccacc uggcugcacu ucagcuggga    2760
cacugggucu ucgcaguaca ggaugcgcug gauggcggug cccugcaccu cgaucagggc    2820
guccacgaag uugguggagg cgauggucca gaagccgcuc acgucgucgu cggugccgug    2880
gccggugaag uugaugguca cggcguccag caggcccagg ucaguaagc gaagccguu     2940 cacguacacg ucgccguacu uggugaucac gaucucucuc acgguggugu gcagcacggc    3000
caggaacuug uacacguuge cuuguaggu guccaccuuc aggaagcagu aguauggcac    3060 cugggugcg cccaggggga uggugaaggu ggcagguggg gggucggagc uguuggagca    3120
cacgaagcuc agguugguc ccagggcggu gugcagcacg augcugcccu cggccaggau    3180 cacggagug ucguuaugu ugaaucucag ggcucuggg gcccucggg cggcggcgcc      3240 guugcacacg ccguccaugg ucugguugaa gcugaagaac uggcccaggc cguagaucuu    3300
```

| | |
|---|---|
| ugggaugcc agcaggcagu ucaccagcag uggcugguug acaccaccu ugccgugcag | 3360 |
| cagggguggag ucguugcuca gcaggaacca guuguugaag gagaagcccu cggggaugug | 3420 |
| gccguugcug ucgguggcga acacguucac ggcguagccg cugcaguugg cggugcaggg | 3480 |
| cucguaguag augccguccu cgccggcgcu ggucacguuc agcauguagu agguuggggu | 3540 |
| guacacguac ugcauggcgc agcuccgcuu guuguagcac cugguggcca cucuggacca | 3600 |
| gucguucuuc agguagaagu gguagaucuu gucggcgaac acggucacuc ugucguuguc | 3660 |
| ccaggugaug cccaccacga uguucuugcc guccugcaug uaggcuggga uggccuuguu | 3720 |
| gaacaggcag uuucugccgg uggucacguc guucacggug gggcccaggg ucuuguuguu | 3780 |
| ggggaacugg cagauucuca gccuggcgau ggcguugugg uugccguugg uggccuugug | 3840 |
| caggucagc ugguagccgc uuggggucgaa gggcuccugg cugaugccga ucucgaagcc | 3900 |
| cuggccggcg ucgauguagc ucaggaagau gccgugcacg ccggaggcgg ucuccaggcc | 3960 |
| ggugccgcag uaccaggagc uggaguucau gcuggcagg uagccgccca gcaccaccac | 4020 |
| ggcggggcc ugcacguuga acuuggagaa gaaccgucug aaguugauug uggacuggca | 4080 |
| ucuugugaca uccugaggga ggcugagggu ggagagcacg gggaggaaga gccagaagua | 4140 |
| guugagggau uucau | 4155 |

<210> SEQ ID NO 5
<211> LENGTH: 4167
<212> TYPE: RNA
<213> ORGANISM: Artificial Sequence
<220> FEATURE:
<223> OTHER INFORMATION: encodes a PEDV S protein

<400> SEQUENCE: 5

| | |
|---|---|
| ucagccgcac ugaacucuga ccuucucgaa caccucugcc gguugaagcc ucgggccucu | 60 |
| acagcauccu gagaaacagg cacagcagca accgcagcau ccacaacaac cggugcuuau | 120 |
| gcagcaaaac accagcaggg auacgacgaa aaucaggacg augaagauga ucagccaaac | 180 |
| ccaccaaggc cauuuaaugu auguuucgac ucgguugagc cauucgagau ccaccagggu | 240 |
| auuguugaug uuguagauca ggcucuggag cuccucggug guguuccuca gacuuucuga | 300 |
| ccguuguuca agaucggcga ucucuccggu cagauucagg uagguagcgu uaaacacguc | 360 |
| gaguggcaag cugggcccug uucuauuggg cagacuggcc aguauuucgu ccagaguuc | 420 |
| guugacgucg auguaguucgg ggaugacauc gggcagcuga ucucuuguga gguugacaua | 480 |
| agucacgacg cagcucucga ucuguacgaa gucagacacg guuggcuuuc uggguucaaa | 540 |
| cauccggcgg cuggacacga aguacucagu ggcuguguga uucugcaguu caugggugaa | 600 |
| cagcaccagu ccuggcucuc ggaggguaag ggcuaucucg ucguucacgc acaaaccggc | 660 |
| gauggcgauc acguccacga agucugaagg cacaagcacc guggagaa acagcaguccc | 720 |
| cugggagca gccuguacca gagagaauau augcucaccg uccccaccgc agaagccgua | 780 |
| gcgcuggcuu uggcucuuca cgcacucguu uaccuucugu ugggccaguu ccgggacgc | 840 |
| uugcaccucc guguauuuug ucagggucug cgccacgaac cguucaggg cacugagucu | 900 |
| cccguuauc aaucgguccga ccugaacguc agccgacagu auguccaagc ggcuauagau | 960 |
| gucgucuaug gagcuagaga uggcuuggaa auugugcugc agcugaacgg ugaguugggu | 1020 |
| cagcgccgcg cccugugagu ucaccacuuc cuggacuuug gcagggcgu gagcgacggu | 1080 |
| guucagcccc uugcuggucu gggaaauggc cucuucacg cuuucgaaug cggaaguaau | 1140 |
| guuuccgaug gcggaauuga aagacucggc cagaagcugc ugguucucu ggagaacauc | 1200 |

```
cgucugcaga gcaagguaau ugagccgagc cuguacggca uagcuaaagg aagggcggc   1260 ugcacucgua aacccgccca auaccauccc gccaucagg cuggcgcuau acaugugcag    1320
cuucucggca uccaccaccc caggcaacac cauuacccca gaauaauacu gagcacacac   1380
caaguccgcg acggaccugc cguuggaaca gcguuuguag uccucaucca ccguacccag   1440
cccguuggug acaacuuuau ugaaggcagc guccucgaug aaggaccucu uuugcacgac   1500
ccugccggaa gcgggaucgu acacgcuaac gccaaggaca uucguaaagu guagccguc   1560 gccguuaaag gagcuaaugg uugccaguug gagugccucu ucggagaugg uaagcaugcu   1620
guuaaccuca acagacucaa ggcgggcgga aagcugcagg gcagauucga ucgucuuaca   1680
ggcggcggua uacugugcua ggagcuguuu acagcgggaa uugccguugc acacauaggu   1740
ggcgcaguca acgcuuacgg gaguguugua cagcugcagg uauucggucc gaaugcucau   1800
ggagaaguuu gucggaaugg agauguugcc ugcacacugua ggugcgaucu ucaccugacc   1860
gcuuugagag gggacauaac cgaugcugcc acucuuugcag accccaaugu uugaauagac   1920
gagaacgggu ucugugcaau uggaaccauc guuagagugg uagaagaacc cgggcaguuc   1980
ccguguggag uugaaggugc uugaugacaa gcuagagauc accccgacaa uaucgucauc   2040
uacauaggcc gccugcucug agaagcuaca aggggucacu gaguaaacgg cgccagaagu   2100
cacguucuug aaggccagga gcugcccaga gucggaggug uaauacacac cggccaggaa   2160
acuggaguua gucagaguga ugauccccuc gccuuugaag ccguagauag uguacuuugu   2220
gcacacaucc agugucauaa agcugacauc agucacgccu ucgaguggu ucggaguucc    2280 ggugaugagc ucaccuuugg uaaacugaaa guacaggag gugaacuuca cgccgcuacc    2340
aaacucgggg uagccaaaca ggucgauggu acaagcacua gccagcagug acgugcucac   2400
gcagaauuug gaaaagcuca gguagucauu aacgcucugg agcguaaagg gacaauugga   2460
auccugggau uugcugacau agccguaaga auuagcacg uuauagaaca gggaaauggu    2520
aaacugucua gugucgacac agaagcuuga gaagccauua augguggguau cacucgcgau   2580 gagguuagcg ccagaguguc caccgaaaga ggcugacacg ugauguuca cgaagcugug    2640 aucguugaaa cugggcagcg ugacgaagcu gaucggcugc ucaugacuga gaagguuccu    2700
acuggagaua ggguaaaagc cgucauccag aucgaaggcc accgagagc acuucaguug    2760 agacacuggg ucgucacagu acaaaauccu cuggauagca gucccugaa ccucaaucag    2820 ggcauccacg aaauugguag aagcaauggu ccaaaacccu gagacgucgu cgucgguucc   2880
augcccugug aaguuaaucg ucacugcauc gagcagccg aggugcaagu agccaaagcc    2940
auucacguac acgucuccau acuuaguaau gacgauuucc cgaacagucg guggcagcac   3000
ggcgaggaac uuguaucgg ugcuguugua gguauccacu ucagaaagc aguaguaugg    3060 caccugugua gcucccagag gaaucgcaaa aguggccaga ugugggguug agcuguugga    3120
gcagacaaaa cuaaaguuag ugcccagugc ugugugcagc acaaugcugc cuucugccaa   3180
gaucacgcuu gugucauuaa uguuaaagcg cagggccuca ggagcgcguu ggacagcugc   3240
gccauugcac acuccaucga uggucugguu aaaggaaaag aauugcccca guccauagau   3300 cuuaggauaua gccaggagac aauugaccaa cagguggcuga uuacugacca ccuuccaug   3360 caccagcgug cugucguuggn acaggaggaa ccaauuguug aaggaaaauc cuucuggggau   3420 guguccauug ggcucagugg cgaaaacauu ugcagcauac ccauggcaau uggcgguaca    3480
gggcugguag cugaugccau cuucucccgc ugaugugacg uucagcaugu aauagguugg    3540
```

| | |
|---|---:|
| cucguacaca uacugcauag cacaaccgcc agaguuguag cacuuugugg cuacgcggcu | 3600 |
| ccagucauuc uugaaguaga aguaauagau uuugucagag aacacaguga cccugucauu | 3660 |
| aucccacgua auuccgacca cacuaugcuc agacaugugu gcaggaauug ccuguugaa | 3720 |
| caagcaauuc cucccugugg ucacgucguu auucgcagua ggcccgagug ucuugauaga | 3780 |
| uggaaacugg cauaugcgca aucgcgcggu agcguuggug uugccauuug uggccuugug | 3840 |
| cagguaaagc ugauagccgc uagggucgaa cggcuccuga cugauuccaa ucucaaaccc | 3900 |
| guguccgccg cgaaugugge uaacaaagau cccgugcacc ccacuugccg ugggaugcug | 3960 |
| uccugcacaa uaccaugugc uauucacgcc ugguucucc ccgauaggga gguauccgcc | 4020 |
| cagcaccaca acggcggug ccuggacauu gaacuugcug aagaagcgcc gaaaguuggu | 4080 |
| auuggcggag caccgaguca cauccugugg caggcuaagc guugagagca caggcaggaa | 4140 |
| cagccaaaag uaugugagac uuuucau | 4167 |

<210> SEQ ID NO 6
<211> LENGTH: 4242
<212> TYPE: RNA
<213> ORGANISM: Artificial Sequence
<220> FEATURE:
<223> OTHER INFORMATION: comprises a sequence encoding a PEDV S protein

<400> SEQUENCE: 6

| | |
|---|---:|
| aaguuuuua uaaugaguuu agaaugauaa uuguugacug augcaggacu ggucuugaau | 60 |
| auuuaucacu gcacucucac uuucucaaac accucagcgg gcuggagccg gggucccucua | 120 |
| cagcagccgc ugaagcaggc gcagcagcag ccgcagcagc cgcagcagcc gguggagaug | 180 |
| cagcagaaca ccagcaggga caccacgaag aucagcacga ugaacacgau cagccacacc | 240 |
| caccauggcc acuugaugua ggucccacu cguucagcc acccagguc caccagggug | 300 |
| uuguugaugu uguagaucag ggacugcagc uccucggugg uguuucucag ggacucgcuu | 360 |
| cucugcucca ggucggcgau cucgccgguc agguucaggu agguggcguu gaacacgucc | 420 |
| aggggcaggc uggggccggu ucuguuggc agggaggcca ggaucucguc cagggucuug | 480 |
| uucacgucga uguagucugg gaucacgucu ggcagcuggu ucugguucag guucacguag | 540 |
| gucaccacgc aggacucgau cugcacgaag ucgcucacgg ugggcuuucu uggcucgaac | 600 |
| auccgucugg agcucacgaa auacucggug gcggugugg ucugcagcuc gugggugaac | 660 |
| agcaccaggc cgggcucucu cagggucagg gcgaucucgu cguucacgca caggccggcg | 720 |
| auggcgauca cgucgaugaa gucgccuggc accagcacgg ugcaggaa cagcaggccc | 780 |
| uguggggcgg ccugcaccag ggagaagaug ugcucgccgu cgccgccgca gaagccguau | 840 |
| cucuggcucu gggacuucac gcacucguuc accuucugcu gggccagcuu ucuggaggcc | 900 |
| ugcaccucgg uguacuuggu caggucuggg gccacgaagg cguucagggc ggacagucug | 960 |
| ccggugauca gucguccac cugcacgucg cggacagga uguccagccu ggaguagaug | 1020 |
| ucgucgaugg agcuggagau ggccuggaag uugugcugca gcugcacggu cagcuggguc | 1080 |
| agggcggcgc ccuggagauu caccaccucc ugcaccuugg ucagggcgug gccacggug | 1140 |
| uucaggcccu uggaggucug gcugauggcc uccuucacgc ucgaaggc ggaggugaug | 1200 |
| uugccgaugg cgcuguugaa gcucucggcc agcagcugcu gguucucug cagcacgucg | 1260 |
| gucucgcaggg ccagguaguu cagucggcc ugcacggcgu agcugaaggg cagggcggcg | 1320 |
| gcggagguga agccgcccag caccaugccg ccgaucaggg aggcgcugua caugugcagc | 1380 |
| uucucggcgu ccaccacgcc uggcagcacc aucacgccgc uguaauacug ggcgcacacc | 1440 |

```
aggucggcca cggaucugcc guugcugcau cucuuguagu ccucguccac ggugcccagg    1500
ccguugguca ccaccuuguu gaaggcggcg uccucgauga agcuccucuu cugcaccacu    1560
cugccgcugg cugggucgua cacgcucacg cccagcacgu uggugaaguu guagccgucg    1620
ccguugaagg agcugauggu ggccagcugc agggccuccu cggagauggu cagcaugcug    1680
uucaccucca cggacuccag ccuggcgcuc agcugcaggg cgcucucgau ggucuugcag    1740
gcggcgugua acugggucag cagcugcuug caucuggagu ugccguugca cacguaggug    1800 gcgcaguccaa cggacacggg ggguguugac agcugcaggu acucgguucu gaugcucaug    1860
gagaaguugg uggggaugga gauguugccg gucacggugg gggcgaucuu caccuggccg    1920
cucugggaug gcacguagcc gauggagccg cucuugcaca cgccgauguu ggaguacacc    1980
agcacuggcu cggugcaguu ggagccgucg uugcugugg agaagaagcc uggcagcucu    2040 cuggugagu ugaaggugcu ggaggacagg cuggagauca cgcccacgau gucgucgucc    2100
acguaggcgg ccugcucgcu gaaggagcag ggggucacgc uguacacggc gccggagguc    2160
acguucuuga aggccagcag cuggccgcug ucggaggugu aguacacgcc ggccaggaag    2220
gagcuguugu ucagggugau gaugcccucg cccuugaagc cguagauggu guacuuggug    2280 cacacguccaa gggucaugaa gcucacgucg gucacgcccu ccaggggcuu uggggugccg    2340
gugaucagcu cgcccucggu gaacuggaag uacaggcugg ugaacuucac gccggagccg    2400
aacucugggu agccgaacag gucgauggug caggcgcugg ccagcaggcu gguggacacg    2460
cagaacuugc ugaaggacag guagucguuc acggacugca ggugaagggg cagguuggag    2520
uccuggcucu ugcucacgua gccguagcug uuggucacgu guagaacag gcugauggug    2580 aacugccugg uguccacgca gaagcuggag aagccguuga uggugugguc ggaggcgauc    2640
agguuggcgc cggaguggcc gccgaaggag gcgcucacgg ugauguucac gaaggagugg    2700
ucguugaagg auggcagggu cacgaagcug auuggcugcu cguggcucag cagguuucug    2760
gagcugaugg gguagaagcc gucguccagg ucgaaggcca ccuggcugca cuucagcugg    2820
gacacugggu cgucgcagua caggaugcgc uggauggcgg ugcccugcac cucgaucagg    2880
gcguccacga aguuggugga ggcgauggucc cagaagccgc ucacgucguc gucggugccg    2940
uggccggaga aguugauggu cacggcgucc agcaggccca ggugcaggua gccgaagccg    3000
uucacguaca cgucgccgua cuuggugauc acgaucucuc ucacguguggg uggcagcacg    3060 gccaggaacu uguacacguu gcuguuuag gguccaccu ucaggaagca guaguauggc    3120 accuggguugg cgcccagugg gauggugaag guggccaggu gggggucgga gcuguuggag    3180
cacacgaagc ucagguuggu gcccagggcg guggugcagca cgaugcugcc cucggccagg    3240 aucacgagg ugucguugau guugaaucuc agggccucug gggcccucug gcggcggcg    3300 ccguugcaca cgccguccau ggucugguug aagcugaaga acuggcccag gccguagauc    3360
uuugggaugg ccagcaggca guucaccagc aguggcuggu ggacaccac cuugccgucg    3420 agcagggugg agucguugcu cagcaggaac caguuguuga aggagaagcc cucggggaug    3480
uggccguugc ugucgguggc gaacacguuc acggcguagc cgcugcaguu ggcggugcag    3540
ggcucguagu agaugccguc cucgccggcg cuggucacgu ucagcaugua guagguuggg    3600 gguguacacgu acugcauggc gcagcuccgc uuguuguagc accugguggc cacucuggac    3660
cagucguucu ucagguagaa guggauagauc uugucggcga acacggucac ucugucguug    3720 ucccaggguga ugcccaccac gauguucuug ccguccugca uguaggcugg gauggccuug    3780
```

-continued

| | |
|---|---|
| uugaacaggc aguuucugcc gguggucacg ucguucacgg uggggcccag ggucuuguug | 3840 |
| uuggggaacu ggcagauucu cagccuggcg auggcguugu gguugccguu gguggccuug | 3900 |
| ugcagguaca gcugguagcc gcuugggucg aagggcuccu ggcugaugcc gaucucgaag | 3960 |
| cccuggccgg cgucgaugua gcucaggaag augccgugca cgccgaggcc ggucuccagg | 4020 |
| ccggugccgc aguaccagga gcuggaguuc augcuuggca gguagccgcc cagcaccacc | 4080 |
| acggcggggg ccugcacguu gaacuuggag aagaaccguc ugaaguugau uggaguuau gacuu | 4140 |
| caucuuguga cauccugagg gaggcugagg guggagagca cggggaggaa gagccagaag | 4200 |
| uaguugaggg auuucauggu gcugcuggac uaccugaguc cu | 4242 |

<210> SEQ ID NO 7
<211> LENGTH: 4242
<212> TYPE: RNA
<213> ORGANISM: Artificial Sequence
<220> FEATURE:
<223> OTHER INFORMATION: comprises a sequence encoding a PEDV S protein

<400> SEQUENCE: 7

| | |
|---|---|
| uuuuuauaa ugaguuuaga augauaauug uugacugaug caggacuggu cuugaauauu | 60 |
| uaucacugca cucucacuuu cucaaacacc ucagcgggcu ggagccgggg uccucuacag | 120 |
| cagccgcuga agcaggcgca gcagcagccg cagcagccgc agcagccggu ggagaugcag | 180 |
| cagaacacca gcagggacac cacgaagauc agcacgauga acacgaucag ccacacccac | 240 |
| cauggccacu ugauguaggu cuccacucug uucagccacu ccagguccac cagggguguug | 300 |
| uugauguuga gaucaggga cugcagcucc ucgguggugu uucucaggga ucgcuucuc | 360 |
| ugcuccaggu cggcgaucuc gccggucagg ucagguagg uggcguugaa cacguccagg | 420 |
| ggcaggcugg ggccgguucu guuuggcagg gaggccagga ucucgccag ggucuuguuc | 480 |
| acgucgaugu agucugggau cacgucuggc agcuggucuc uggcagguu cacguagguc | 540 |
| accacgcagg acucgaucug cacgaagucg cucacggugg gcuuucuugg cucgaacauc | 600 |
| cgucuggagc ucacgaaaua cucgguggcg ugugguucu gcagcucgug ggugaacagc | 660 |
| accaggccgg gcucucucag ggucagggcg aucucgucgu ucacgcacag gccggcgaug | 720 |
| gcgaucacgu cgaugaaguc gccuggcacc agcacggugu gcaggaacag caggcccugu | 780 |
| ggggcggccu gcaccaggga gaagaugugc ucgccgucgc cgccgcagaa gccguaucuc | 840 |
| uggcucuggg acuucacgca cucguucacc uucugcuggg ccagcuuucu ggaggccugc | 900 |
| accucggugu acuggucagg gucugggcc acgaaggcgu cagggcgga cagucugccg | 960 |
| gugaucaguc uguccaccug cacgucggcg gacaggaugu ccagccugga guagaugucg | 1020 |
| ucgauggagc uggagauggc cuggaaguug ugcugcagcu gcacggucag cugggucagg | 1080 |
| gcggcgcccu gggaguucac caccuccugc accuugguca gggcgugggc cacggugun uc | 1140 |
| aggcccuugg aggucgggcu gauggccucc uucacgcucu cgaaggcgga ggugauguug | 1200 |
| ccgauggcgc uguugaagcu cucggccagc agcugcuggu uucucugcag cacgucgguc | 1260 |
| ugcagggcca gguaguucag ucuggccugc acggcguagc ugaagggcag ggcggcggcg | 1320 |
| gaggugaagc cgcccagcac caugccgccg aucaggagg cgcuguacau gugcagcuuc | 1380 |
| ucggcgucca ccacgccugg cagcaccauc acgccgcugu aauacgggc gcacaccagg | 1440 |
| ucggccacgg aucgccguu gcugcaucuc uuguagccu cgccacgguu gcccaggccg | 1500 |
| uuggucacca ccuuguugaa ggcggcgucc ucgaugaagc uccucuucug caccacucug | 1560 |
| ccgcuggcug ggucguacac gcucacgccc agcacguugg ugaaguugua gccgucgccg | 1620 |

```
uugaaggagc ugaugguggc cagcugcagg gccuccucgg agauggucag caugcuguuc  1680
accuccacgg acuccagccu ggcgcucagc ugcagggcgc ucucgauggu cuugcaggcg  1740
gcgguguacu gggucagcag cugcuugcau cuggaguugc cguugcacac guagguggcg  1800
caguccacgg acacgggggu guuguacagc ugcagguacu cgguucugau gcucauggag  1860
aaguuguggg ggauggagau guugccgguc acggugggggg cgaucuucac cuggccgcuc  1920
```

| | |
|---|---:|
| uggccggcgu cgauguagcu caggaagaug ccgugcacgc cggaggcggu cuccaggccg | 4020 |
| gugccgcagu accaggagcu ggaguucaug cuuggcaggu agccgcccag caccaccacg | 4080 |
| gcggggggccu gcacguugaa cuuggagaag aaccgucuga aguugauugu ggacuggcau | 4140 |
| cuugugacau ccugagggag gcugaggdug gagagcacgg ggaggaagag ccagaaguag | 4200 |
| uugagggauu ucauggugcu gcuggacuac cugaguccua ag | 4242 |

<210> SEQ ID NO 8
<211> LENGTH: 4245
<212> TYPE: RNA
<213> ORGANISM: Artificial Sequence
<220> FEATURE:
<223> OTHER INFORMATION: comprises a sequence encoding a PEDV S protein

<400> SEQUENCE: 8

| | |
|---|---:|
| aaguuuuuua uaaugaguuu agaaugauaa uuguugacug augcaggacu ggucuugaau | 60 |
| auuuaucacu gcacucucac uuucucaaac accucagcgg gcuggagccg ggguccucua | 120 |
| cagcagccgc ugaagcaggc gcagcagcag ccgcagcagc cgcagcagcc gguggagaug | 180 |
| cagcagaaca ccagcaggga caccacgaag aucagcacga ugaacacgau cagccacacc | 240 |
| caccauggcc acuugaugua ggucuccacu cuguucagcc acuccagguc caccaggggug | 300 |
| uuguugaugu guagaucag ggacugcagc uccucggugg uguuucag ggacucgcuu | 360 |
| cucugcucca ggucggcgau ucgccgguc agguucaggg agguggcguu gaacacgucc | 420 |
| aggggcaggc ugggggccggu ucuguuuggc agggaggcca ggaucucguc cagggucuug | 480 |
| uucacgucga uguagucugg gaucacgucu ggcagcuggu cucuggucag guucacguag | 540 |
| gucaccacgc aggacucgau cugcacgaag ucgcucacgg uggggcuuucu uggcucgaac | 600 |
| auccgucugg agcucacgaa auacucggug gcggugugg ucugcagcuc gugggugaac | 660 |
| agcaccaggc cgggcucucu cagggucagg gcgaucucgu cguucacgca caggccggcg | 720 |
| auggcgauca cgucgaugaa gucgccuggc caagcacgg ugucaggaa cagcaggccc | 780 |
| ugugggggcgg ccugcaccag ggagaagaug ugcucgccgu cgccgccgca gaagccguau | 840 |
| cucuggcucu gggacuucac gcacucguuc accuucugcu gggccagcuu ucuggaggcc | 900 |
| ugcaccucgg uguacuuggu cagggucugg gccacgaagg cguucagggc ggacagucug | 960 |
| ccggugauca gucuguccac cugcacgucg cggacagga uguccagccu ggaguagaug | 1020 |
| ucgucgaugg agcuggagau ggccuggaag uugugcugca gcugcacggu cagcuggguc | 1080 |
| agggcggcgc ccugggaguu caccacuccc ugcaccuugg ucaggcgug ggccacggug | 1140 |
| uucaggcccu uggaggucug gcugauggcc uccuucacgc ucucgaaggc ggaggugaug | 1200 |
| uugccgaugg cgcuguugaa gcucucggcc agcagcugcu gguuucucug cagcacgucg | 1260 |
| gucugcaggg ccagguaguu cagucuggcc ugcacggcgu agcugaaggg cagggcggcg | 1320 |
| gcggagguga agccgcccag caccaugccg ccgaucaggg aggcgcugua cauugcagc | 1380 |
| uucucggcgu ccaccacgcc uggcagcacc aucacgccgc uguaauacug ggcgcacacc | 1440 |
| aggucggcca cggaucugcc guugcugcau ucuguagu ccucguccac ggugcccagg | 1500 |
| ccguuggucc accuuguuu gaaggcgcg uccucgauga agcuccucuu cugcaccacu | 1560 |
| cugccgcugg cugggucgua cacgcucacg cccagcacgu uggugaaguu guagccgucg | 1620 |
| ccguugaagg agcugauggu ggccagcugc agggccuccu cggagauggu cagcauggcu | 1680 |
| uucaccucca cggacuccag ccuggcgcuc agcugcaggg cgcucgau ggucuugcag | 1740 |
| gcggcggugu acugggucag cagcugcuug caucuggagu ugccguugca cacguaggug | 1800 |

```
gcgcagucca cggacacggg ggugunguac agcugcaggu acucgguucu gaugcucaug   1860
gagaaguugg uggggaugga gauguugccg gucacggugg gggcgaucuu caccuggccg   1920
cucugggaug gcacguagcc gauggagccg cucuugcaca cgccgauguu ggaguacacc   1980
agcacuggcu cggugcaguu ggagccgucg uugcuguggu agaagaagcc uggcagcucu   2040
cugguggagu ugaaggugcu ggaggacagg cuggagauca cgcccacgau gucgucgucc   2100
acguaggcgg ccugcucgcu gaaggagcag ggggucacgc uguacacggc gccgaagguc   2160
acguucuuga aggccagcag cuggccgcug ucggaggugu aguacacgcc ggccaggaag   2220
gagcuguugg ucagggugau gaugcccucg cccuugaagc cguagauggu guacuugguc   2280
cacacgucca gggucaugaa gcucacgucg gucacgcccu ccagggggcuu ugggugccg   2340 gugaucagcu cgcccucggu gaacuggaag uacaggcugg ugaacuucac gccggagccg   2400
aacucugggu agccgaacag gucgauggug caggcgcugg ccagcaggcu gguggacacg   2460
cagaacuugc ugaaggacag guaucguuc acggacugca gggugaaggg gcaguuggag   2520
uccuggcucu ugcucacgua gccguagcug uuggucacgu uguagaacag gcugaugguug   2580 aacugccugg uguccacgca gaagcuggag aagccguuga uggugguguc ggaggcgauc   2640
agguuggcgc cggaguggcc gccgaaggag cgcucacgg ugauguucac gaaggagugg   2700
ucguugaagg auggcagggu cacgaagcug auuggcugcu cguggucag cagguuucug   2760 gagcugaugg gguagaagcc gucguccagg ucgaaggcca ccuggcugca cuucagcugg   2820
gacacugggu cgucgcagua caggaugcgc uggauggcgg ugcccugcac cucgaucagg   2880
gcguccacga aguggugga ggcgauggguc cagaagccgc ucacgucguc gucggugccg   2940
uggccgguga aguugauggu cacggcgucc agcaggccca ggugcaggua gccgaagccg   3000
uucacguaca cgucgccgua cuggugauc acgaucucuc ucacguggg ugcagcacg   3060 gccaggaacu uguacacguu gcuguuguag guguccaccu ucaggaagca guauauggc   3120 accugggugg cgcccagugg gauggugaag guggccaggu gggggucgga gcuguuggag   3180
cacacgaagc ucagguuggu gcccagggcg gugugcagca cgaugcugcc cucggccagg   3240 aucacgagg ugucguugau guugaaucuc agggccucug ggcccucug gcggcggcg   3300 ccguugcaca cgccguccau ggucugguug aagcugaaga acuggccag gccguagauc   3360 uuuggaugg ccagcaggca guucaccagc aguggcuggu ggacaccac cuugccuguc   3420 agcagguugg agucguugcu cagcaggaac caguuguuga aggagaagcc cucggggaug   3480
uggccguugc ugucgguggc gaacacguuc acggcguagc cgcugcaguu ggcggugcag   3540
ggcucguagu agauggccguc cucgccggcg cugggucacgu ucagcaugua guagguuggg   3600
guguacacgu acugcauggc gcagcccgc uguugguagc accuguggc cacucuggac   3660 cagucguucu ucagguagaa guguagauc uuugucggcga acacgguecac ucugucguug   3720 ucccagguga ugccaccacg gauguucuug cogucugca guaggcugg daugugccuug   3780 uugaacaggc aguuucugcc gguggucacg ucguucacgg ugggeccag ggucuuguug   3840 uuggggaacu ggcagauucu cagccuggcg augggeguugu gguugccguu gguggccuug   3900
ugcagguaca gcugguagcc gcuugggcg aagggcuccu ggcugaugcc gaucucgaag   3960
cccuggccgg cgucgaugua cucaggaag augccgugca cgccggaggc ggucuccagg   4020
ccggugccgc aguaccagga gcuggaguc augcuuggca gguagccgcc cagcaccacc   4080
acggcggggg ccugcacguu gaacuuggag aagaaccguc ugaaguugau uguggacugg   4140
```

| | |
|---|---|
| caucuuguga cauccugagg gaggcugagg guggagagca cggggaggaa gagccagaag | 4200 |
| uaguugaggg auuucauggu gcugcuggac uaccugaguc cuaag | 4245 |

<210> SEQ ID NO 9
<211> LENGTH: 12291
<212> TYPE: RNA
<213> ORGANISM: canine distemper virus

<400> SEQUENCE: 9

| | |
|---|---|
| accagacaaa gcuggguaug auaacuuauu aauaaccguu guuuuuuuc guauaaccaa | 60 |
| guuugauagc aaugaauagu aggggcuag gagccagacu aaccguuag ugauuucuaa | 120 |
| ucagugcacu auaaccuaac aauuugaacc acuccuuuau cucuuuuguc ucaagcugaa | 180 |
| agagccaauu cuuuuggggg auugucguua ggaugagaga ccugucagau ccggacagau | 240 |
| uauccauaaa uaaguuacga ugcaagucga aauuaugug guuggcuuuc agguuucgga | 300 |
| caauccuggu aauuucguau aagcucccg aguaaagcaa auauagcca caguacuucu | 360 |
| uugcaaugau agauacgagc ucccuuuccu gacuugcgau uaacacaggg uaugcaugga | 420 |
| acauuccaug ugaagauugg ugguuauccu ugaaccuugc gaguuccgg uaaaggaucg | 480 |
| ugauagaucc uuucagcccu uccucgccug acgaaauauc auggugaagc agguucuuac | 540 |
| auaccuuaag accauuaauu guaagcccac aauugauuaa uaccuucuca auacuuguua | 600 |
| aacccuggag gugaggauug aaggauucag caugaaaugg aggucgcugc aaagacugca | 660 |
| cacaugcugc cugcuuugau gaaggaugu gcccuaccaa cccaggugaa guucgaauac | 720 |
| cgacucgcaa aaucguugu uuaaucccu ccggauugac uagucccu gcucuaagac | 780 |
| caguaaaaac aagguaggcc ucuguugaca caaaauugcu guaucuuggg uaaacuauga | 840 |
| aacuucgaag aaaauguggg agugcauaua aaauaaaucc uugaacccag ucgccacuag | 900 |
| cuggcaugau cuuaauuacu aacacugacc cuaccuuccc uaauaucaaa gucauugaua | 960 |
| auauagcaga caauuccucc aacuuuucga uuaugucuuu guccgguagu gacucuauau | 1020 |
| ccgagugaau caacccaaga cugcuagcag agaucuggcu caguauguac uuguaacaau | 1080 |
| caacacuccc aacccaaguu acuucugguc ugccauugaa aagcacaguc gccaauuuau | 1140 |
| cgagccuaa uugauguucc accagacuga ccucagaagg guaaggugaa aucucucguu | 1200 |
| guccaguucu ggacucuacu gacacaccac uguuauaaua acaucuugac aaucuuaaua | 1260 |
| gcucuuuaua uacgucaac auugcaccug aaccucucc uaggauaau ccguguucuu | 1320 |
| cagacguaaa uucguucuua aucacagaag cuauuucaac ugccuuguaa caugcaguag | 1380 |
| aguugauccc aauucuucug aaugagugaa ccucauaguu ccggacuccu aaaccuguaa | 1440 |
| uggguaaguu augugucuu guugcacagcu gacucagaag uuuggccagg ucaucuuucg | 1500 |
| guggggucaaa uucugacuuu aauucugagg ccuuagaggu agaauuauuu cuuagaggac | 1560 |
| gccuuucuaa gcauccaaca gcaucaguga ugaauccggg auccacucuc agucuuaucu | 1620 |
| gcuugauuga gccucuucua agauauguca gggaacauga auugaucu auuaagauag | 1680 |
| guuugucauu ccaugucaga ccaacauggg auucuagggc uuuugacuuu aaguaccccg | 1740 |
| auaacagc acauuucugu guuggugucu acccacgaau cugggacaa ucacgagggu | 1800 |
| uacaauaaag gucagauaag augcauaggu gccuggcuug uauguguca aaucuuucag | 1860 |
| guaugacauc cucgcacuu ucgcauaaaa ugaaugagaa ucaucuaauu ucaucauuua | 1920 |
| acagaagguc uagguaaauc auguaacagu uauagaucag guugcauaca guuuauguua | 1980 |
| gguuuuggga gucaagagag gguccaugaa uagguucaau caucccacug ucccaaaacc | 2040 |

```
gucuauauac uuuaggaugg cucaaugcau ugguuaaaau uuugaagacu ccuuuacuca    2100
uucuacucag gaaagagaac aacaacucac ccauuuggua cuuuccagaa ggucggugau    2160
aaugaauuuc aaagcsccag uugauugcag cacauuggcc uagauauaca guaaauaauc    2220
uaggcucaac uagaagaaac ucagugauaa aacuauugau aucaucaucg ccaauuaacg    2280
cagagacuuc auuuaggugg uccuuuucaa acuuuguaau caucucaacc auagacauag    2340
caguagacuu agcuagcaca ugauaaagcu gcccuguugu ccaugugaca aacucuacaa    2400
ugugcuuucu gugacucugg uuauaaaguc ugacugcauc uuucucaaua uagggguuac    2460
ugucauaaau caaggauuuu guacagauau uucuugguau gacgacauuu cugagcccug    2520
ggacucuugg auggucgcuc auggguauua cgcaacaauc uguuucaaca guaaaugua     2580 auacgguauu agaucgccg gugguugaag acaaucuaaa uaagugcuca aggauccca     2640 ggcccaggag cauaccuugu ugauaaauaa aauuugaguc cacuucuuug ucaucuauaa    2700
uaaaagaaag auuaucauuc gagauaguug cauaacgugc cacucugaug agagaggucc    2760
cugaguauuu gacuugagua cucuugucuc uuagucggug agcuagauua guagaagugg    2820
aaauuggggu aaucauccgu aauuccucaa gugagaguguu cgcucucugu uuugccaagg    2880
uccaagccuc uugccaagau ucugucaucau caccauaggc ccaugaguac acaguugcua    2940
uucucacugc ugauuucaga gaccuacuag gagauuugac gaaugcuagu uucaugucug    3000
uucuuucuuc uguuguggac ccuauguaug gcacccucag ugcagauguu cccucuguaa    3060
uacuauccaa uuggcaauuc gcugguacaa aaaaccaacc auaguuauga gagccugaug    3120
cacaaagcaa acaggauuca ugucuucuga ucauauaacc cuucauugau ucaaggauau    3180
ccgggacuuc uagaccauaa auaggacgac ccuucgccag cuuggcccac augugguucc    3240
uuaaugcucu cgcuagcugg acggaacaug agucuugauc gaugagcgga ucaugcccu    3300 ucccugacaa cagucugaua ccugcccuaa auuguucaua aucauaaguu gacaaacggg    3360
uuauuauucu agggguuaga ccuccucuuu ucaugcuugc ucguaucaac cccuuugugg    3420 ugcuagcau uccggugauu gcccucucuug caccugugau cguguuaucu agaauuucau    3480
gugcagcccu ugggauaaua auuuuccauu ccauuaagaa agcugcuaaa gcuucauccu    3540
cauccugacu uucaucaugg aacaauccuc ucagcaucgg auuuggacug uugauaagga    3600
caugccuggc ugugauauu uuaaggaguc ggguuaugcu cuggacacag ggcagauugg    3660
cagaauaagg gucacuugcc caaucaaau aagaagaguc accggguau ugggucauga    3720 ccugauguag aaucuccacu ccaagaaggc cugaucggau cauucguuug aggucagcaa    3780
uagaagaugu cacgggauc ccgauauucc ugacaaagag ccuacucaua uugagguaau    3840
uaagaccgcc aaugggugcg gggagaauug ccaucuuggu caagagacag ugaucugua     3900 cgaggguuc uaucacaucc cguguacaug cugaauugau agugaauccu aaugaauua     3960 auacuguguu aaugauuuuu aaaauguuca gucgcuaggc uaauauacgg ucaaacccuu    4020
ucucaauggc uuucgcuaau guuguugaaa uguugcugca cgcggcucgg gucucaucca    4080 cuauugauuuc ugaccaaaau acacaccuag cuauacucuu cagggauugu gagauuaaca    4140
ucccgucaua auagaucccu uuugaguauca caaaaagug ggaagagauu auuguuucau    4200
uugcuuucaa augaugugccg acaucaugua accucugucu caaggcuaua aaguauucg     4260 cggucacucg acuggcuuca gauuucuuca aggcauagga ccaggugcuu gguacucuuu    4320
uagugacagc aauaguuugg uuaucaccuu ggacaaguga ugcaauucug acaccgcucu    4380
```

```
caugugccgc caaguacaaa uaagguaugg uguuaauagu ccacaacuuc ugacaauaac    4440
ccuccacccc ccccauuggg uauuugauga auauuugaga guuaggggcu guauucaagu    4500
ccacaugacg aucgagaucu ggagggcagu gggggucacu acguauaag aucgacuguu     4560 ccaaucuucu guguaaccau uggaaaaaug aggggagacc guagauuuca uuuaaucucu    4620
gagcaaaaau acugaugguc ucauaacgcc aaucagaca guacuuuug agauccguag      4680 uuauaaaugc acuuacaguu ucauagaucu cuaugucauu gucuucucuu cuacuggugc    4740
aaaaauuugg guuggguucu auauaucuac uacuugggga agagacggag ugaagugcuc    4800
cucgauaagg ugcagguuuc agggauuuac ucgguuagu gaggccacga uggaagucuu     4860
ucuugucuuu cggaaccccg acacagcca gagugugcaa ugcuuagug agaucguguu      4920 caucccuugc caucccauug uccuugaagu acuucccaau uccauuagau aucaaguucu    4980
cugcuaugac cugacaggcu cgcauuuugu aggucauuuu agcgauagc cucccuaccu     5040 cuuuaaucuc uuucucuuug agacuguaug auaggguugaa aucaggaucu ucuagauauu    5100
gaccugagau aacguacaua aucaguuuau aaggucaaau cugagaguccc ucuagaaaca    5160 cauuaacaag ucuccgagac ucaguggagc gagguggauu guaccugagg aauucuuuug    5220
gguacacuga gucccacucu uuucuuaggg cugccaaagc cuuaucuuuc agguacaugg    5280
ucaaaucacu gucuaggcua agaggcauaa agcauuuaaa ucgaauuccu gcaaaggauu    5340
uccaguuuuc uauacauuga cuauagguga uucccucccc ugaggcauga gcauuucuga    5400
ugaugggaga ugcaugaaca ggaagauccca ucggaggcca aguuccccca ugucuauccc    5460
gauaaccguu aaugauuauc ccacagaaua uagcaugucc cuucaucaua gucucauaag    5520
agacaacuuu ggguugauuc aguguguuucc guacguuuuc ugcugcuguu auugcuucua    5580 accuuggggug accgaaacuu cuaaagaagg aaaagauuuc ccuguuaua uguauauccu     5640 cugugaugaa aacgaagucu agagcuuggg uuaaaguuug gaacgucucu ucaguauaga    5700
agccauuguc cuguaaaauc uccugaauuu cagcaaagca gugacucaga aaagcacccc    5760
ugagagagaa ggugaugucu uuuaacugca aguaagccaa ugagagaggc uccaguagag    5820
ccaccaauug auagguugaa uuucccagau ccgggaaaaa uccgucaauu agaucccaga    5880
gauaccugau ccugacaugc aaaguugagu aacguugauc aauugccaua gcaguaucag    5940
ucauuagccu cccuucuauu acaucacagu acaucaagac cauuucaaau guuagguaau    6000
aaacauugug acuggugaga ucaauaauac auacaagguc ccuagacacu agcacauuaa    6060
augauucacc uuuuacaaag acaggaucu gccuccgcuu cgacaguug ugaguagagg      6120 auuuaaucac ugaucucauu ucuguuuaa uuguaaacca uagaaggaaa gguucgaacc     6180 acgugagcu uugcauaauu augccugcuu caucaauuuu ggcccaauna gucuugcca     6240 gugcgccccc uaaccaaua uuaagauuaa uaucguuuaa gcauuuuug accccgucug      6300 uuauuuugcu auagaugcua uuccucuuu ugaauauauu ucucagccuc agagaggga     6360 cucgauccug ugcaugaaau agaaguuugu ugcaauuugg guauaucaca ugguuguguu    6420
ugggauaaga uaacaagguc ugauuaauaa ugcucccgau uucgaugcag uuaaugauca    6480
ucugguuuga gaacccuucu gaaauucucu cuuugauauu acgcacuaau guuguaucaa    6540
ggaguugaua gcuaugucua auucgugcgu auucuaaaau agcuacuagc uuauuugguua   6600 caauugggcu aucgauugg accucagggu auagaaucug guucacugac acagaguccaa   6660 uggcuaaaag gauccuggau ccuuaguuuu uuuauaaugc uggagauggu uuaauucauu    6720
caucuguaag ggauuuuuca ccauacucau caugccuaag uccaauugag auguguauca    6780
```

```
uuauacuguc agggauuuga acgguuacau gagaaucuua uacggacuaa auucucaaca    6840
cugguuguag aguuggcgau guuagccucg uaucuguaaa auuggugaca ccacaaauua    6900
ucaucccaca caaaacauuc aauccuuagg aaaucagguc uaccuuggu aguuagucua     6960 aaugagugcg uauaagaaau cguccggauu gggucuaaaa cauaauaaac aaucgcauga    7020
ucauuucgug auauaucaua cguugcuaug acauaucuaa aacucugugu aggcaacacc    7080
acuacauugg acucgaugag gacaucucua ucuauaauuu gagauguuug aauagguaaa    7140
uaacaauuuc cacaugauuc ccugggcgca aauguuaaua cuuggggu cacagugaac      7200 uggucuccuc uacuugcuuu guuuaucaau ccaaggauug uuccguuuuu aggaggaaug    7260
guaagccauc cggaguucaa aagugggcuu ucauaauaau ccauaccauc uccauucagu    7320
auaaccggac cguaugugaa cgauauguua aguugaaggu caacacuugc aucuagaggu    7380
aaugucaacc gcccauaaga uggcaacugu ccuccuccga agggucccca ugacguuugg    7440
uugcacaugg gguagguuuu ucuuugacaa gcugacucca gccaaccuuu uguucuucu     7500 uguuucucag aggccagggc aggcaccauc cagguugcaa ugaaucuuu uauaaaacca     7560 cgguggauuu uuauauguau uuucccauu gaugggugag cgacagguau cacuuccuca     7620 auaugauccca uagguguugc cccaaauauc cccaguguca cuacuagaau accaucuugu   7680 gaacccccugc ugucauggua uaauaauaca gugcucucuu cuacacacaa ggaagccagu   7740
gucaacucac ccacugcuau ggacauaccc uuggcuuugg aauuuccgg gaggaccaua     7800 uaguggung uuuggaguaa uggcaugucaa uucagccacc uuuuaaugaa cccuauuuca    7860
aagacucgaa ucucuugagu gucgaacucc cguucuauau caucaggcac uagcaaguaa    7920
guuuugccau acacgccguc ugagguagcg gucagcauau ugauuaucuc ugagguucuu    7980
gagaucaaag acauggauaa cgagacugau agggggaaaa cuuugccuac ugaaguagua    8040
gcuccacugc aucuguaugg uggaauaug ucacuccugc ccccagagag ggcugauaaa     8100
aggaugggau uugcugccga ugcaauagau uuucugaucc caauugucuc acaguaauuu    8160
guaaaauuca ccuugaccuu acuaggcggg uuaaugcacc aguggagauc gcggaaaucg    8220
aauucucugu ucggauugaa gaaauuuguc uuuugaagga uaaauuguuu gaucucguuu    8280
agcuuuugug gcaaccguaa cccaaucuca uccccaauaa ucuugaagag cggugucaag    8340
acaucuauga cuugaugaug uacggccucu gauuucucca uaccucuuuu cagcaaucug    8400
cuaaauucca uauugcuagu ugauacuugg ugaaaucgaa cuccagugau agcaagcagg    8460
gccaggauuc caaccaauag gaugagaagg acaaacaaca aauaagguggg ucuccugccc   8520 ccaugcucuu cugucacugg ggacagcuug gaugaauugg cucuugcauu guccuuguag    8580 aaggcacccca ccuugucuug guaggagagc auugcuggac uaccgagcc cuaaguuuuc    8640 uuuaauuacg auaaucaugg ucagucuuuu ccaauguuua uugcaguuga gugacucuug    8700
aagaaaauug ggcggggguua auagauauca aaucuggcaa ucaagcgaga uauaugacca   8760
gaauacuuca gagugaucuc acauaggauu ucgaaguucc gguuagauca gguuuaaaug    8820
ccggaucgac cuuaguauuc cgcuugagug ucuguuggua gcgucuuuua caacaguaaa    8880
ucagcaacag caaagccagg gcuguaccac uuaauauagg aacgcugagg agacugccaa    8940
aauuaaagga agagcgccua acugucucaa ggaucugguu agaggagucu aucaguaccu    9000
uagcaucauc caguuucuua agggcguucc cuaaauuugu accuacaucu aaccucuaa     9060 gugauauagc agggccuaag gcaacuuugc uuucauauac cauaucaggg uauugccugc    9120
```

```
cuccaacuug gauaguuaca ccaucuauuu caaccaguqq qcaqquaucq qaqqcaauqa   9180 augucagcaa cuuaucagga cucugauuaa uaauugugcu ugugcuauaa cacuuacaua   9240
guauagacgc acaauuugcg acgauguuac cuuuugacag aauaaauuug uugcccauag   9300
ucccagauac caagguccgg gcacaagaug aagugucgcc ccuaauacau uguuguaaga   9360
gugggcucau ggqquacaqq qaquucuqqc uacaaauqqc uqacucuqaq acqaauacac   9420 aggaugacuc aucaaaauua gauauuaagu aaccauuagu ugcaauauac cucgggacag   9480
ugguguacca cucuuguqau ccuauquuqu aaqaaacuqc uuccaqucuq uqqacuauaa   9540 cccccuugac uucugauaaa guqqquauq aqauacuuaq qauqauqaau ucccqqqaa    9600 uaucaacaug aguauuuuuu guuuuuaucc cccgacucuc caagauugca aucauaucac   9660
cuccagagua ucccaacuuc ucaaguaucu uaugaauuuc uccuccaaga gcauaacuca   9720
gugcuugaau ugauaucucg gcugaaauag ggucacguaa acucgggcca aauauugaca   9780
auaacucagu auaauaccua agcaguuuua acccuaaucu cugcccaacu aauucacaug   9840
acauauguug cauagcaggg acgaguucgu uguuaacgua auccggacu cccgaacgg     9900 caaugacggu ucuuggguua qccucccuaa uuucuucaau aqcuuuquua qacuquucaa   9960 ggcugguucu aagagauugg auugcuugag cauugagguu ggauugaugu aaagcuauuc  10020
cugcagugau uugugcagcu guagccacuc cuaaagcugc accugcaagu accacuccug  10080
caaaacgccu uugucuccua gcugacccua ugacgcaa gggcuucaca ucuugguca    10140 uuagagucag agcuugguug auugguucga ggacugaauu caauaauuuc ucauacucac  10200
cuaauucugc uuugguacaa uuaucuauaa gugaaacauu aggcaucagu uuuaugacca  10260 aguacugqug acgqqccua qccauqaucu uauaauqqac acaucaquc ccaauaaucc    10320 caauaguuga caaauuauuc caaguauucu gagccuugga caaagaaag agacugqcua    10380 uuccgaggca ccacaggacu aaccaggagc acugagagcc ugaguugauu gcauugggu    10440 gccgccuuuc gaucugggau cucgcuccuu uggagacacu cucggcaug ugcuggauaa    10500 uagccucgug guuuccguga acgagaugu ucccaaucu guagcugguu ugcuugcgag    10560
accugguccu guucauggug uaggagacgu gucuguccaa uguucgagga ucauaguucg  10620
uggaucgcug agcugacguu augcuguguc gugcucggga gguccugguc ucgucgguc   10680 cggugcuggg uuguggggg cgguuuuguu gggguaugug ugggguuuug gagcuuuug    10740 ggauuuccuu gugcaugggg cuuggcuguu uguggggguu ccugccuggc cucgggcugg  10800
uggacuuggu uggccuguug gcuugcuacg uccuggaccc uaaguuuuga uuaauuauua  10860
augagcugug auagaaagau ggacagucau cacuccguga aacaagacua cuagugaugg  10920
cuugagauca ggcaagugcg ugggaguaua acuguuaaag ugagauuccu agaagcgaag  10980
cucaaacccc caggcaucca uucauuucuu ggucgauaa ugaucaaccc aaucuuaagc   11040
aagaacuguu uugauucagc uauuuucaua ugaggcguc acuqqaauuq uqqqcacqqa    11100 ugggcagucu agaaaccuau aggccacgcu caaaaugcag gagcaacauc uagacagucg  11160
auauuuauac cccuaauccu cgcuugcggg gaucaaggga ucuugggcaa ugcuacuaag  11220
gcguuugagu uuuaguucau gaacuaauga uuuagagaaa uuugaaaaga cccgaucau    11280 cgcugacgau aacaucauua uaaacucuga aaucuugugg gacugauggu ugcaagacug  11340
cuuggauccu uacuauuuug cacucuaauc uccauagaga ucgauucaaa ucuucauuga  11400
ucuccaugag cgggtuaacac aggauuuucu ugaaaccuag cugggcauuc aaggccuugc  11460
ucaucuuacc aguacaucgu augugaagac uuguuccucc uaucccuccu agagcaaaca  11520
```

| | | | | |
|---|---|---|---|---|
| cuaaucccau | cuuuucaauu | uucaguuuac | aauaaucagc | agaguaagcu | ugguuuucu | 11580 |
| uacgccugaa | auugccgaua | cggaccauga | auguuacuug | gugaucuuug | aacaugcuca | 11640 |
| aauuaccucg | gcuugaacag | acaucucccu | caacuugaau | ggugacuaaa | auguuaaaug | 11700 |
| cuaaagcauu | ccuggagcgg | aauucaaaca | ucccgcgggg | aauucuguaa | cuuccaucgu | 11760 |
| cugauagucg | agugaugcuc | auauauacca | cccugaaucu | uugugcuaug | ucuaauggua | 11820 |
| uuagauugac | ugcguuacag | acuugauuug | cacugaacac | acuccacuc | guaaggaccu | 11880 |
| uuuuccacgg | aguuaagaug | ugcaaugggg | uguuauuaua | aaauaccagu | uguuccuuga | 11940 |
| caccugcagu | ucgccuugcc | acaauaucca | acagggguggc | uucuuucaau | aacuccucag | 12000 |
| gucuggcugu | aguacgccca | acucccaaag | gcagcaaucc | aaauguucuu | ccaauugggg | 12060 |
| guccgaggcc | aucauugucu | ucuauuauac | ccaguagaaa | aauauacaug | aagcauucau | 12120 |
| cuuuccuauc | gccgaguccu | ggaucuauua | cucgacuug | ggguaugagc | cuaccaucgg | 12180 |
| gauaaguggu | aggcaaaaua | ggggccaaua | agcccuuggu | gucccaagaa | gacugaucga | 12240 |
| agucguacac | cucagucauu | uuuuaggaga | ggacuuaggc | ucuugugucc | u | 12291 |

<210> SEQ ID NO 10
<211> LENGTH: 3396
<212> TYPE: RNA
<213> ORGANISM: canine distemper virus

<400> SEQUENCE: 10

| | | | | | |
|---|---|---|---|---|---|
| uuuuuauaa | uugcuuuuaa | gcgauaguga | aagcaguuuu | gcgccgguua | guagauuagu | 60 |
| caacgcuaca | gauuaagcau | gaguaauacu | cuugaccauc | ugguagaacu | cguuuagguu | 120 |
| gucaucuccc | uugauauuuu | uaagcagagc | cagcauguua | uguuucgac | uuugaucaac | 180 |
| ucugcuugau | cugaucaaug | augcaaguac | agcuuuagaa | ggugcgguau | ccuuuggguu | 240 |
| guauccgauu | gccgagcuag | acucuuuguc | aauggguuuc | agcuggaggu | cucucaauag | 300 |
| uugaccuuuu | gagcccagag | uaauaccacu | guccuuccga | uuaccgcggg | augaugcggg | 360 |
| cugcuugaga | acuuccgcua | gugcucuccc | ugaaucccuc | ccuaugauag | ggcggagcuc | 420 |
| uggauuaaug | ucgacauuug | ccguagggguc | ucccguguccс | uuccaaaac | cagguauagc | 480 |
| uaucauaaug | cuugauagau | gccccucaau | cguggaaauc | gcauauuuu | guuugcugau | 540 |
| uuguuucuua | auugaaucag | ucucuccuuu | aagcaguaaa | aagguaucca | guuuagaaag | 600 |
| uauugcuuga | uuaucuucag | uuaguuuagu | aauggcagau | cgaauuucuu | guaucucaga | 660 |
| gaaaagcuca | ucaucguacu | cacugucaga | cucagccuca | uuugaggucc | ugggagggag | 720 |
| uugcguacca | gacucgaguu | ugcauuucug | ggucaucuuu | gcauucauug | cagguuggcg | 780 |
| gacauucccc | gcagacacac | uuggcucuga | ugauccccca | guugacuuga | gugcagauuu | 840 |
| gguugcacca | cuugucgauc | cagcaacuau | ccccauuccc | ugugagacug | accucucuuc | 900 |
| ugugcccuuu | uuaauggauc | cacacuccgg | aacccuuguc | uuaccuucgg | gauuaugugg | 960 |
| gaacugcaga | gucuucccau | cccuuuucug | aaucccuaca | uuucugcuug | ucuugagcag | 1020 |
| agcacuuaau | uccucuucca | ucagcaugcu | cacaucagcu | gcccugucug | guuuaaggcc | 1080 |
| gaaagaauau | ccccaguuag | augaagcauu | uccuucggaa | uaaucuucgc | cagaauccuc | 1140 |
| agugcuauca | ucagggcuuc | cuucuccgcu | cucgaauccu | cgauuaccga | cagugccugc | 1200 |
| agguaccacg | agacgucag | caucuucgau | ucccuuaacc | ucuucaccgc | ugugaucaua | 1260 |
| aacaugauaa | caucguauuc | cagguccugg | uuggaugucc | ucuuuaggga | gcugcucugc | 1320 |

```
uuccacaagc gcagaguugc uuucuccaca ucccggauua uuuuggagua cauggccgac    1380
auaguuugau ccuuuuguug gcucguguga uucaucgaga uucugagagu ccuccucuuc    1440
cugcaugccu gugguuccau ucucuuggcc ugggugcag guuggauc ugaugcugcu       1500 gaccucuuga aucccucaa ugucaggagg auucucucug agggcuuuga ggcauccag      1560 cccuuugcug acaugguagg ccuguccuc ugccauuuag ggauagaacg ggugguccgga   1620 ugaaugguug aucggguuug uggacccgg guccuaaguu uuuuauaaug aguuuagaau    1680
gauaauuguu gacugaugca ggacuggucu ugaauauuua auugaguagc ucucuaucau   1740
uauaaacagg agaacuaucu ucacugguccu agguugacu gagcaucuua guaagcaucc   1800
ucaucuuggc gauugcuucc aucgauuucc ggucaucauc auuccauca ucuuggguaa    1860 uuuggguguc guggcguggc ucacuccguu cagagcuguu gacgucuggg gugugcccug   1920
gaggccuuuc aucacugaag ugaaugggu aucugucucc ucccugguuu ucggaccucu    1980
uguugauggu cgggggugu ugauuagcga cuucggaucu uuccgagugc aggaagguaa   2040
uuugggauug cuugggacca guagcucgaa ucgucgguc cucuguuguc uuggaugcua    2100
uuucugacac cagcugagcu uccuccuugg ugaugccaag cucggcagca agugcagagc   2160
uuacuuugcc ggcagaucgu cuaaccauuu cuugcccgag ucugaaguag gcugggucaa   2220
aguaagaucg accgaaauuu aauccuccca uggaguuuc aaguucaaca ccaaccccca    2280
uagcauaacu ccagagcaau ggguaggacc cugcacuaaa uuuguuuuga acagaguuuu   2340
ccaagauaac caugucauggu gcuguuucac ccaucuguug auauagcauc augagggauu  2400
caauaguugu uaauucuccg gaaaacucau gcaacccaag agccggauac auaguuucaa   2460
ugccaaacuu gauaguuagg augaaacuag cuaacccagc uuccacagug uaguuaucua   2520
uaucacaaau cauuucagca auucaggcu uuguccuugg ggaucuuuug auguccaaaaa  2580 ugagugccac caugaaucgc ucaaagaua ggccucagc aauccuguuu cuaacaauau     2640
caagccagau uuuguucauu cuaaauucuc cgaccacacg ucuuugcugg guauacuuaa   2700
uccaccuucu caucuccgag ucggcugcag uaucaggagc agucaccgcu uuagcuagca   2760
ggauccaaau uugagccaaa auggaagcua guaauauauu gaauugcuca gcaucaucaa   2820 cuucuaugluc uacuauauc uuauucuccca accagccuaa uugcccuuga gcuuucgacc    2880
cuucgucuac aauuugaag aacucaucug ccucagaauc cagacuugcu ccucuggaug    2940
caaauguaag accgcaaaca gaguugaugc uugguauuac ucuacuaac uugaugcuua    3000 caucagggguc gucuaugauc ucuggauca acugucagg ggauuccacg aacaaggaga    3060
ggauacugau uaagaucca guuaauuuag ggccguugau ucuggauca ccaaccaacc     3120 uaacaaguc auccaauagu cgagaucuug uaacaaugcu ugaacacccc gggauuagga    3180
cuauaaugac augcuuuauu cccucuuauug cucccccgga gccagaggca agaggggguu   3240
ggucccgagu cccucuugaac aguggugaggc uuuuaagaag gcuagccaua uuggauagguc  3300 ugaacccuga ccuuguucuc uaagguagga ucauugaccc uaaguuuuua auaaaauauu    3360
caauaauuua acuauccaua gccaacuuug ucuggu                              3396
```

<210> SEQ ID NO 11
<211> LENGTH: 4152
<212> TYPE: DNA
<213> ORGANISM: porcine epidemic diarrhea virus

<400> SEQUENCE: 11

```
atgaaatccc tcaactactt ctggctcttc ctccccgtgc tctccaccct cagcctccct    60
```

```
caggatgtca caagatgcca gtccacaatc aacttcagac ggttcttctc caagttcaac      120
gtgcaggccc ccgccgtggt ggtgctgggc ggctacctgc caagcatgaa ctccagctcc      180
tggtactgcg gcaccggcct ggagaccgcc tccggcgtgc acggcatctt cctgagctac      240
atcgacgccg gccagggctt cgagatcggc atcagccagg agcccttcga cccaagcggc      300
taccagctgt acctgcacaa ggccaccaac ggcaaccaca cgccatcgc caggctgaga       360 atctgccagt tccccaacaa caagaccctg gcccccaccg tgaacgacgt gaccaccggc      420
agaaactgcc tgttcaacaa ggccatccca gcctacatgc aggacggcaa gaacatcgtg      480
gtgggcatca cctgggacaa cgacagagtg accgtgttcg ccgacaagat ctaccacttc      540
tacctgaaga cgactggtc cagagtggcc accaggtgct acaacaagcg gagctgcgcc      600
atgcagtacg tgtacacccc aacctactac atgctgaacg tgaccagcgc cggcgaggac      660
ggcatctact acgagccctg caccgccaac tgcagcggct acgccgtgaa cgtgttcgcc      720
accgacagca acgccacat ccccgagggc ttctcccttca caactggtt cctgctgagc       780 aacgactcca ccctgctgca cggcaaggtg gtgtccaacc agccactgct ggtgaactgc      840
ctgctggcca tcccaaagat ctacggcctg ggccagttct tcagcttcaa ccagaccatg      900
gacggcgtgt gcaacggcgc cgccgcccag agggcccag aggccctgag attcaacatc       960
aacgacacct ccgtgatcct ggccgagggc agcatcgtgc tgcacaccgc cctgggcacc     1020
aacctgagct tcgtgtgctc caacagctcc gaccccacc tggccaccct caccatccca      1080
ctgggcgcca cccaggtgcc atactactgc ttcctgaagg tggacaccta caacagcaac     1140
gtgtacaagt tcctggccgt gctgccaccc accgtgagag agatcgtgat caccaagtac     1200
ggcgacgtgt acgtgaacgg cttcggctac ctgcacctgg cctgctgga cgccgtgacc      1260 atcaacttca ccggccacgg caccgacgac gacgtgagcg cttctggac catcgcctcc      1320 accaacttcg tggacgccct gatcgaggtg cagggcaccg ccatccagcg catcctgtac     1380
tgcgacgacc cagtgtccca gctgaagtgc agccaggtgg ccttcgacct ggacgacggc     1440
ttctacccca tcagctccag aaacctgctg agccacgagc agccaatcag cttcgtgacc     1500
ctgccatcct tcaacgacca ctccttcgtg aacatcaccg tgagcgcctc cttcggcggc     1560
cactccggcg ccaacctgat cgcctccgac accaccatca acggcttctc cagcttctgc     1620
gtggacacca ggcagttcac catcagcctg ttctacaacg tgaccaacag ctacggctac     1680
gtgagcaaga gccaggactc caactgcccc ttcaccctgc agtccgtgaa cgactacctg     1740
tccttcagca agttctgcgt gtccaccagc ctgctggcca cgcctgcac catcgacctg     1800 ttcggctacc cagagttcgg ctccggcgtg aagttcacca gcctgtactt ccagttcacc     1860
gagggcgagc tgatcaccgg caccccaaag cccctggagg gcgtgaccga cgtgagcttc     1920
atgaccctgg acgtgtgcac caagtacacc atctacggct tcaagggcga gggcatcatc     1980
accctgacca cagctccctt cctggccggc gtgtactaca cctccgacag cggccagctg     2040
ctggccttca gaaacgtgac ctccggcgcc gtgtacagcg tgacccctg ctccttcagc     2100 gagcaggccg cctacgtgga cgacgacatc gtgggcgtga tctccagcct gtcctccagc     2160
accttcaact ccaccagaga gctgccaggc ttcttctacc acagcaacga cggctccaac     2220
tgcaccgagc cagtgctggt gtactccaac atcggcgtgt gcaagagcgg ctccatcggc     2280
tacgtgccat cccagagcgg ccaggtgaag atcgccccca ccgtgaccgg caacatctcc     2340
atccccacca acttctccat gagcatcaga accgagtacc tgcagctgta caacacccc     2400
```

| | |
|---|---|
| gtgtccgtgg actgcgccac ctacgtgtgc aacggcaact ccagatgcaa gcagctgctg | 2460 |
| acccagtaca ccgccgcctg caagaccatc gagagcgccc tgcagctgag cgccaggctg | 2520 |
| gagtccgtgg aggtgaacag catgctgacc atctccgagg aggccctgca gctggccacc | 2580 |
| atcagctcct tcaacggcga cggctacaac ttcaccaacg tgctgggcgt gagcgtgtac | 2640 |
| gacccagcca gcggcagagt ggtgcagaag aggagcttca tcgaggacgc cgccttcaac | 2700 |
| aaggtggtga ccaacggcct gggcaccgtg gacgaggact acaagagatg cagcaacggc | 2760 |
| agatccgtgg ccgacctggt gtgcgcccag tattacagcg gcgtgatggt gctgccaggc | 2820 |
| gtggtggacg ccgagaagct gcacatgtac agcgcctccc tgatcggcgg catggtgctg | 2880 |
| ggcggcttca cctccgccgc cgccctgccc ttcagctacg ccgtgcaggc cagactgaac | 2940 |
| tacctggccc tgcagaccga cgtgctgcag agaaaccagc agctgctggc cgagagcttc | 3000 |
| aacagcgcca tcggcaacat cacctccgcc ttcgagagcg tgaaggaggc catcagccag | 3060 |
| acctccaagg ccctgaacac cgtggcccac gccctgacca aggtgcagga ggtggtgaac | 3120 |
| tcccagggcg ccgccctgac ccagctgacc gtgcagctgc agcacaactt ccaggccatc | 3180 |
| tccagctcca tcgacgacat ctactccagg ctggacatcc tgtccgccga cgtgcaggtg | 3240 |
| gacagactga tcaccggcag actgtccgcc ctgaacgcct tcgtggccca gacccctgacc | 3300 |
| aagtacaccg aggtgcaggc ctccagaaag ctggcccagc agaaggtgaa cgagtgcgtg | 3360 |
| aagtcccaga gccagagata cggcttctgc ggcggcgacg gcgagcacat cttctccctg | 3420 |
| gtgcaggccg ccccacaggg cctgctgttc ctgcacaccg tgctggtgcc aggcgacttc | 3480 |
| atcgacgtga tcgccatcgc cggcctgtgc gtgaacgacg agatcgccct gacccctgaga | 3540 |
| gagcccggcc tggtgctgtt cacccacgag ctgcagaacc acaccgccac cgagtatttc | 3600 |
| gtgagctcca cggatgtt cgagccaaga aagcccaccg tgagcgactt cgtgcagatc | 3660 |
| gagtcctgcg tggtgaccta cgtgaacctg accagagacc agctgccaga cgtgatccca | 3720 |
| gactacatcg acgtgaacaa gaccctggac gagatcctgg cctccctgcc aaacagaacc | 3780 |
| ggccccagcc tgcccctgga cgtgttcaac gccaccacc tgaacctgac cggcgagatc | 3840 |
| gccgacctgg agcagagaag cgagtccctg agaaacacca ccgaggagct gcagtccctg | 3900 |
| atctacaaca tcaacaacac cctggtggac ctggagtggc tgaacagagt ggagacctac | 3960 |
| atcaagtggc catggtgggt gtggctgatc gtgttcatcg tgctgatctt cgtggtgtcc | 4020 |
| ctgctggtgt tctgctgcat ctccaccggc tgctgcggct gctgcggctg ctgctgcgcc | 4080 |
| tgcttcagcg gctgctgtag aggaccccgg ctccagcccg ctgaggtgtt tgagaaagtg | 4140 |
| agagtgcagt ga | 4152 |

<210> SEQ ID NO 12
<211> LENGTH: 4155
<212> TYPE: DNA
<213> ORGANISM: porcine epidemic diarrhea virus

<400> SEQUENCE: 12

| | |
|---|---|
| atgaaatccc tcaactactt ctggctcttc ctcccgtgc tctccaccct cagcctccct | 60 |
| caggatgtca agatgcca gtccacaatc aacttcagac ggttcttctc caagttcaac | 120 |
| gtgcaggccc ccgccgtggt ggtgctgggc ggctacctgc aagcatgaa ctccagctcc | 180 |
| tggtactgcg gcaccggcct ggagaccgcc tccggcgtgc acggcatctt cctgagctac | 240 |
| atcgacgccg ccagggcttt cgagatcggc atcagccagg agcccttcga cccaagcggc | 300 |
| taccagctgt acctgcacaa ggccaccaac ggcaaccaca cgccatcgc caggctgaga | 360 |

```
atctgccagt tccccaacaa caagaccctg ggccccaccg tgaacgacgt gaccaccggc    420
agaaactgcc tgttcaacaa ggccatccca gcctacatgc aggacggcaa gaacatcgtg    480
gtgggcatca cctgggacaa cgacagagtg accgtgttcg ccgacaagat ctaccacttc    540
tacctgaaga acgactggtc cagagtggcc accaggtgct acaacaagcg agctgcgcc     600 atgcagtacg tgtacacccc aacctactac atgctgaacg tgaccagcgc cggcgaggac    660
ggcatctact acgagccctg caccgccaac tgcagcggct acgccgtgaa cgtgttcgcc    720
accgacagca acggccacat ccccgagggc ttctccttca caactggtt cctgctgagc     780 aacgactcca ccctgctgca cggcaaggtg tgtccaacc agccactgct ggtgaactgc     840
ctgctggcca tcccaaagat ctacggcctg gccagttct tcagcttcaa ccagaccatg     900
gacggcgtgt gcaacggcgc cgccgcccag agggccccag aggccctgag attcaacatc    960
aacgacacct ccgtgatcct ggccgagggc agcatcgtgc tgcacaccgc cctgggcacc   1020
aacctgagct tcgtgtgctc caacagctcc gaccccacc tggccacctt caccatccca   1080
ctgggcgcca cccaggtgcc atactactgc ttcctgaagg tggacaccta caacagcaac   1140
gtgtacaagt tcctggccgt gctgccaccc accgtgagag agatcgtgat caccaagtac   1200
ggcgacgtgt acgtgaacgg cttcggctac ctgcacctgg gcctgctgga cgccgtgacc   1260
atcaacttca ccggccacgg caccgacgac gacgtgagcg gcttctggac catcgcctcc   1320
accaacttcg tggacgccct gatcgaggtg cagggcaccg ccatccagcg catcctgtac   1380
tgcgacgacc cagtgtccca gctgaagtgc agccaggtgg ccttcgacct ggacgacggc   1440
ttctacccca tcagctccag aaacctgctg agccacgagc agccaatcag cttcgtgacc   1500
ctgccatcct tcaacgacca ctccttcgtg aacatcaccg tgagcgcctc cttcggcggc   1560
cactccggcg ccaacctgat cgcctccgac accaccatca acggcttctc cagcttctgc   1620
gtggacacca ggcagttcac catcagcctg ttctacaacg tgaccaacag ctacggctac   1680
gtgagcaaga gccaggactc caactgcccc ttcaccctgc agtccgtgaa cgactacctg   1740
tccttcagca gttctgcgt gtccaccagc ctgctggcca cgcctgcac catcgacctg   1800 ttcggctacc agagttcgg ctccggcgtg aagttcacca gcctgtactt ccagttcacc   1860
gagggcgagc tgatcaccgg cacccccaaag cccctggagg gcgtgaccga cgtgagcttc   1920
atgaccctgg acgtgtgcac caagtacacc atctacggct tcaagggcga gggcatcatc   1980
accctgacca cagctcctt cctggccggc gtgtactaca cctccgacag cggccagctg   2040
ctggccttca gaacgtgac ctccggcgcc gtgtacagcg tgaccccctg ctccttcagc   2100
gagcaggccg cctacgtgga cgacgacatc gtgggcgtga tctccagcct gtcctccagc   2160
accttcaact ccaccagaga gctgccaggc ttcttctacc acagcaacga cggctccaac   2220
tgcaccgagc cagtgctggt gtactccaac atcggcgtgt gcaagagcgg ctccatcggc   2280
tacgtgccat cccagagcgg ccaggtgaag atcgcccca ccgtgaccgg caacatctcc   2340
atccccacca acttctccat gagcatcaga accgagtacc tgcagctgta caacaccccc   2400
gtgtccgtgg actgcgccac ctacgtgtgc aacggcaact ccagatgcaa gcagctgctg   2460
acccagtaca ccgccgcctg caagaccatc gagagcgccc tgcagctgag cgccaggctg   2520
gagtccgtgg aggtgaacag catgctgacc atctccgagg aggccctgca gctggccacc   2580
atcagctcct tcaacggcga cggctacaac ttcaccaacg tgctgggcgt gagcgtgtac   2640
gacccagcca gcggcagagt ggtgcagaag aggagcttca tcgaggacgc cgccttcaac   2700
```

```
aaggtggtga ccaacggcct gggcaccgtg gacgaggact acaagagatg cagcaacggc    2760
agatccgtgg ccgacctggt gtgcgcccag tattacagcg gcgtgatggt gctgccaggc    2820
gtggtggacg ccgagaagct gcacatgtac agcgcctccc tgatcggcgg catggtgctg    2880
ggcggcttca cctccgccgc cgccctgccc ttcagctacg ccgtgcaggc cagactgaac    2940
tacctggccc tgcagaccga cgtgctgcag agaaaccagc agctgctggc cgagagcttc    3000
aacagcgcca tcggcaacat cacctccgcc ttcgagagcg tgaaggaggc catcagccag    3060
acctccaagg gcctgaacac cgtggcccac gccctgacca aggtgcagga ggtggtgaac    3120
tcccagggcg ccgccctgac ccagctgacc gtgcagctgc agcacaactt ccaggccatc    3180
tccagctcca tcgacgacat ctactccagg ctggacatcc tgtccgccga cgtgcaggtg    3240
gacagactga tcaccggcag actgtccgcc ctgaacgcct tcgtggccca gaccctgacc    3300
aagtacaccg aggtgcaggc ctccagaaag ctggcccagc agaaggtgaa cgagtgcgtg    3360
aagtcccaga gccagagata cggcttctgc ggcggcgacg gcgagcacat cttctcccctg   3420 gtgcaggccg ccccacaggg cctgctgttc ctgcacaccg tgctggtgcc aggcgacttc    3480
atcgacgtga tcgccatcgc cggcctgtgc gtgaacgacg agatcgccct gaccctgaga    3540
gagcccggcc tggtgctgtt cacccacgag ctgcagaacc acaccgccac cgagtatttc    3600
gtgagctcca gacggatgtt cgagccaaga aagcccaccg tgagcgactt cgtgcagatc    3660
gagtcctgcg tggtgaccta cgtgaacctg accagagacc agctgccaga cgtgatccca    3720
gactacatcg acgtgaacaa gaccctggac gagatcctgg cctccctgcc aaacagaacc    3780
ggccccagcc tgcccctgga cgtgttcaac gccacctacc tgaacctgac cggcgagatc    3840
gccgacctgg agcagagaag cgagtccctg agaaacacca ccgaggagct gcagtccctg    3900
atctacaaca tcaacaacac cctggtggac ctggagtggc tgaacagagt gggagaccta    3960
atcaagtggc catggtgggt gtggctgatc gtgttcatcg tgctgatctt cgtggtgtcc    4020
ctgctggtgt tctgctgcat ctccaccggc tgctgcggct gctgcggctg ctgctgcgcc    4080
tgcttcagcg gctgctgtag aggaccccgg ctccagcccg ctgaggtgtt tgagaaagtg    4140
agagtgcagt gataa                                                     4155

<210> SEQ ID NO 13
<211> LENGTH: 4245
<212> TYPE: DNA
<213> ORGANISM: Artificial Sequence
<220> FEATURE:
<223> OTHER INFORMATION: DNA reverse complement of SEQ ID NO:8

<400> SEQUENCE: 13
cttaggactc aggtagtcca gcagcaccat gaaatccctc aactacttct ggctcttcct      60
ccccgtgctc tccacccctca gcctccctca ggatgtcaca agatgccagt ccacaatcaa    120
cttcagacgg ttcttctcca agttcaacgt gcaggccccc gccgtggtgg tgctgggcgg    180
ctacctgcca agcatgaact ccagctcctg gtactgcggc accggcctgg agaccgcctc    240
cggcgtgcac ggcatcttcc tgagctacat cgacgccggc cagggcttcg agatcggcat    300
cagccaggag cccttcgacc caagcggcta ccagctgtac ctgcacaagg ccaccaacgg    360
caaccacaac gccatcgcca ggctgagaat ctgccagttc cccaacaaca agaccctggg    420
ccccaccgtg aacgacgtga ccaccggcag aaactgcctg ttcaacaagg ccatcccagc    480
ctacatgcag gacggcaaga acatcgtggt gggcatcacc tgggacaacg acagagtgac    540
cgtgttcgcc gacaagatct accacttcta cctgaagaac gactggtcca gagtggccac    600
```

```
caggtgctac aacaagcgga gctgcgccat gcagtacgtg tacacccaa cctactacat    660
gctgaacgtg accagcgccg gcgaggacgg catctactac gagccctgca ccgccaactg    720
cagcggctac gccgtgaacg tgttcgccac cgacagcaac ggccacatcc ccgagggctt    780
ctccttcaac aactggttcc tgctgagcaa cgactccacc ctgctgcacg gcaaggtggt    840
gtccaaccag ccactgctgg tgaactgcct gctggccatc ccaaagatct acggcctggg    900
ccagttcttc agcttcaacc agaccatgga cggcgtgtgc aacggcgccg ccgcccagag    960
ggccccagag gccctgagat caacatcaa cgacacctcc gtgatcctgg ccgagggcag   1020
catcgtgctg cacaccgccc tgggcaccaa cctgagcttc gtgtgctcca acagctccga   1080
cccccacctg gccaccttca ccatcccact gggcgccacc caggtgccat actactgctt   1140
cctgaaggtg acacctaca acagcaacgt gtacaagttc ctggccgtgc tgccacccac   1200
cgtgagagag atcgtgatca ccaagtacgg cgacgtgtac gtgaacggct cggctacct   1260
gcacctgggc ctgctggacg ccgtgaccat caacttcacc ggccacgca ccgacgacga   1320
cgtgagcggc ttctggacca tcgcctccac caacttcgtg gacgccctga tcgaggtgca   1380
gggcaccgcc atccagcgca tcctgtactg cgacgaccca gtgtcccagc tgaagtgcag   1440
ccaggtggcc ttcgacctgg acgacggctt ctaccccatc agctccagaa acctgctgag   1500
ccacgagcag ccaatcagct tcgtgaccct gccatccttc aacgaccact ccttcgtgaa   1560
catcaccgtg agcgcctcct cggcggcca ctccggcgcc aacctgatcg cctccgacac   1620
caccatcaac ggcttctcca gcttctgcgt ggacaccagg cagttcacca tcagcctgtt   1680
ctacaacgtg accaacagct acggctacgt gagcaagagc caggactcca actgcccctt   1740
caccctgcag tccgtgaacg actacctgtc cttcagcaag ttctgcgtgt ccaccagcct   1800
gctggccagc gcctgcacca tcgacctgtt cggctaccca gagttcggct ccggcgtgaa   1860
gttcaccagc ctgtacttcc agttcaccga gggcgagctg atcaccggca ccccaaagcc   1920
cctggagggc gtgaccgacg tgagcttcat gaccctggac gtgtgcacca gtacaccat   1980
ctacggcttc aagggcgagg gcatcatcac cctgaccaac agctccttcc tggccggcgt   2040
gtactacacc tccgacagcg gccagctgct ggccttcaag aacgtgacct ccggcgccgt   2100
gtacagcgtg accccctgct ccttcagcga gcaggccgcc tacgtggacg acgacatcgt   2160
gggcgtgatc tccagcctgt cctccagcac cttcaactcc accagagagc tgccaggctt   2220
cttctaccac agcaacgacg gctccaactg caccgagcca gtgctggtgt actccaacat   2280
cggcgtgtgc aagagcggct ccatcggcta cgtgccatcc cagagcggcc aggtgaagat   2340
cgccccccacc gtgaccggca acatctccat ccccaccaac ttctccatga gcatcagaac   2400
cgagtacctg cagctgtaca caccccgt gtccgtggac tgcgccacct acgtgtgcaa   2460
cggcaactcc agatgcaagc agctgctgac ccagtacacc gccgcctgca agaccatcga   2520
gagcgccctg cagctgagcg ccaggctgga gtccgtggag gtgaacagca tgctgaccat   2580
ctccgaggag gccctgcagc tggccaccat cagctccttc aacggcgacg gctacaactt   2640
caccaacgtg ctgggcgtga gcgtgtacga cccagccagc ggcagagtgg tgcagaagag   2700
gagcttcatc gaggacgccg ccttcaacaa ggtggtgacc aacggcctgg gcaccgtgga   2760
cgaggactac aagagatgca gcaacggcag atccgtggcc gacctggtgt gcgcccagta   2820
ttacagcggc gtgatggtgc tgccaggcgt ggtggacgcc gagaagctgc acatgtacag   2880
cgcctccctg atcggcggca tggtgctggg cggcttcacc tccgccgccg ccctgccctt   2940
```

| | |
|---|---|
| cagctacgcc gtgcaggcca gactgaacta cctggccctg cagaccgacg tgctgcagag | 3000 |
| aaaccagcag ctgctggccg agagcttcaa cagcgccatc ggcaacatca cctccgcctt | 3060 |
| cgagagcgtg aaggaggcca tcagccagac ctccaagggc ctgaacaccg tggcccacgc | 3120 |
| cctgaccaag gtgcaggagg tggtgaactc ccagggcgcc gccctgaccc agctgaccgt | 3180 |
| gcagctgcag cacaacttcc aggccatctc cagctccatc gacgacatct actccaggct | 3240 |
| ggacatcctg tccgccgacg tgcaggtgga cagactgatc accggcagac tgtccgccct | 3300 |
| gaacgccttc gtggcccaga ccctgaccaa gtacaccgag gtgcaggcct ccagaaagct | 3360 |
| ggcccagcag aaggtgaacg agtgcgtgaa gtcccagagc cagagatacg gcttctgcgg | 3420 |
| cggcgacggc gagcacatct tctccctggt gcaggccgcc cacagggcc tgctgttcct | 3480 |
| gcacaccgtg ctggtgccag cgacttcat cgacgtgatc gccatcgccg gcctgtgcgt | 3540 |
| gaacgacgag atcgccctga ccctgagaga gcccggcctg gtgctgttca cccacgagct | 3600 |
| gcagaaccac accgccaccg agtatttcgt gagctccaga cggatgttcg agccaagaaa | 3660 |
| gcccaccgtg agcgacttcg tgcagatcga gtcctgcgtg gtgacctacg tgaacctgac | 3720 |
| cagagaccag ctgccagacg tgatcccaga ctacatcgac gtgaacaaga ccctggacga | 3780 |
| gatcctggcc tccctgccaa acagaaccgg ccccagcctg cccctggacg tgttcaacgc | 3840 |
| cacctacctg aacctgaccg gcgagatcgc cgacctggag cagagaagcg agtccctgag | 3900 |
| aaacaccacc gaggagctgc agtccctgat ctacaacatc aacaacaccc tggtggacct | 3960 |
| ggagtggctg aacagagtgg agacctacat caagtggcca tggtgggtgt ggctgatcgt | 4020 |
| gttcatcgtg ctgatcttcg tggtgtccct gctggtgttc tgctgcatct ccaccggctg | 4080 |
| ctgcggctgc tgcggctgct gctgcgcctg cttcagcggc tgctgtagag gaccccggct | 4140 |
| ccagcccgct gaggtgtttg agaaagtgag agtgcagtga taaatattca agaccagtcc | 4200 |
| tgcatcagtc aacaattatc attctaaact cattataaaa aactt | 4245 |

<210> SEQ ID NO 14
<211> LENGTH: 5153
<212> TYPE: DNA
<213> ORGANISM: Artificial Sequence
<220> FEATURE:
<223> OTHER INFORMATION: comprises SEQ ID NO:13

<400> SEQUENCE: 14

| | |
|---|---|
| ccgcggtaat cggaaggaca gtggtattac tctgggctca aaaggtcaac tattgagaga | 60 |
| cctccagctg aaacccattg acaaagagtc tagctcggca atcggataca aaccaaagga | 120 |
| taccgcacct tctaaagctg tacttgcatc attgatcaga tcaagcagag ttgatcaaag | 180 |
| tcacaaacat aacatgctgg ttctgcttaa aaatatcaag ggagatgaca acctaaacga | 240 |
| gttctaccag atggtcaaga gtattactca tgcttaatct gtagcgttga ctaatctact | 300 |
| aaccggcgca aaactgcttt cactatcgct taaaagcaat tataaaaaac ttaggactca | 360 |
| ggtagtccag cagcaccatg aaatccctca actacttctg gctcttcctc cccgtgctct | 420 |
| ccacccctcag cctccctcag gatgtcacaa gatgccagtc acaatcaac ttcagacggt | 480 |
| tcttctccaa gttcaacgtg caggccccg ccgtggtggt gctgggcggc tacctgccaa | 540 |
| gcatgaactc cagctcctgg tactgcggca ccggcctgga gaccgcctcc ggcgtgcacg | 600 |
| gcatcttcct gagctacatc gacgccggcc agggcttcga gatcggcatc agccaggagc | 660 |
| ccttcgaccc aagcggctac cagctgtacc tgcacaaggc caccaacggc aaccacaacg | 720 |
| ccatcgccag gctgagaatc tgccagttcc ccaacaacaa gaccctgggc cccaccgtga | 780 |

```
acgacgtgac caccggcaga aactgcctgt tcaacaaggc catcccagcc tacatgcagg      840
acggcaagaa catcgtggtg ggcatcacct gggacaacga cagagtgacc gtgttcgccg      900
acaagatcta ccacttctac ctgaagaacg actggtccag agtggccacc aggtgctaca      960
acaagcggag ctgcgccatg cagtacgtgt acacccaac  ctactacatg ctgaacgtga     1020
ccagcgccgg cgaggacggc atctactacg agccctgcac cgccaactgc agcggctacg     1080
ccgtgaacgt gttcgccacc gacagcaacg gccacatccc cgagggcttc tccttcaaca     1140
actggttcct gctgagcaac gactccaccc tgctgcacgg caaggtggtg tccaaccagc     1200
cactgctggt gaactgcctg ctggccatcc caaagatcta cggcctgggc cagttcttca     1260
gcttcaacca ccatggac ggcgtgtgca acggcgccgc cgcccagagg ccccagagg        1320 ccctgagatt caacatcaac gacacctccg tgatcctggc cgagggcagc atcgtgctgc     1380
acaccgccct gggcaccaac ctgagcttcg tgtgctccaa cagctccgac ccccacctgg     1440
ccaccttcac catcccactg ggcgccaccc aggtgccata ctactgcttc ctgaaggtgg     1500
acacctacaa cagcaacgtg tacaagttcc tggccgtgct gccacccacc gtgagagaga     1560
tcgtgatcac caagtacggc gacgtgtacg tgaacggctt cggctacctg cacctgggcc     1620
tgctggacgc cgtgaccatc aacttcaccg ccacggcac cgacgacgac gtgagcggct      1680
tctggaccat cgcctccacc aacttcgtgg acgccctgat cgaggtgcag ggcaccgcca     1740
tccagcgcat cctgtactgc gacgacccag tgtcccagct gaagtgcagc caggtggcct     1800
tcgacctgga cgacggcttc tacccatca gctccagaaa cctgctgagc cacgagcagc      1860
caatcagctt cgtgaccctg ccatccttca acgaccactc cttcgtgaac atcaccgtga     1920
gcgcctcctt cggcggccac tccggcgcca acctgatcgc ctccgacacc accatcaacg     1980
gcttctccag cttctgcgtg gacaccaggc agttcaccat cagcctgttc tacaacgtga     2040
ccaacagcta cggctacgtg agcaagagcc aggactccaa ctgccccttc acctgcagt      2100 ccgtgaacga ctacctgtcc ttcagcaagt tctgcgtgtc caccagcctg ctggccagcg     2160
cctgcaccat cgacctgttc ggctacccag agttcggctc cggcgtgaag ttcaccagcc     2220
tgtacttcca gttcaccgag ggcgagctga tcaccggcac cccaaagccc ctggagggcg     2280
tgaccgacgt gagcttcatg accctggacg tgtgcaccaa gtacaccatc tacggcttca     2340
agggcgaggg catcatcacc ctgaccaaca gctccttcct ggccggcgtg tactacacct     2400
ccgacagcgg ccagctgctg gccttcaaga acgtgacctc cggcgccgtg tacagcgtga     2460
ccccctgctc cttcagcgag caggccgcct acgtggacga cgacatcgtg ggcgtgatct     2520
ccagcctgtc ctccagcacc ttcaactcca ccagagagct gccaggcttc ttctaccaca     2580
gcaacgacgc ctccaactgc accgagccag tgctggtgta ctccaacatc ggcgtgtgca     2640
agagcggctc catcggctac gtgccatccc agagcggcca ggtgaagatc gcccccaccg     2700
tgaccggcaa catctccatc cccaccaact tctccatgag catcagaacc gagtacctgc     2760
agctgtacaa caccccgtg tccgtggact gcgccaccta cgtgtgcaac ggcaactcca     2820
gatgcaagca gctgctgacc cagtacaccc ccgcctgcaa gaccatcgag agcgccctgc     2880
agctgagcgc caggctggag tccgtggagg tgaacagcat gctgaccatc tccgaggagg     2940
ccctgcagct ggccaccatc agctccttca acggcgacgg ctacaacttc accaacgtgc     3000
tgggcgtgag cgtgtacgac ccagccagcg gcagagtggt gcagaagagg agcttcatcg     3060
aggacgccgc cttcaacaag gtggtgacca acggcctggg caccgtggac gaggactaca     3120
```

| | |
|---|---|
| agagatgcag caacggcaga tccgtggccg acctggtgtg cgcccagtat tacagcggcg | 3180 |
| tgatggtgct gccaggcgtg gtggacgccg agaagctgca catgtacagc gcctccctga | 3240 |
| tcggcggcat ggtgctgggc ggcttcacct ccgccgccgc cctgcccttc agctacgccg | 3300 |
| tgcaggccag actgaactac ctggccctgc agaccgacgt gctgcagaga aaccagcagc | 3360 |
| tgctggccga gagcttcaac agcgccatcg gcaacatcac ctccgccttc gagagcgtga | 3420 |
| aggaggccat cagccagacc tccaagggcc tgaacaccgt ggcccacgcc ctgaccaagg | 3480 |
| tgcaggaggt ggtgaactcc cagggcgccg ccctgaccca gctgaccgtg cagctgcagc | 3540 |
| acaacttcca ggccatctcc agctccatcg acgacatcta ctccaggctg acatcctgt | 3600 |
| ccgccgacgt gcaggtggac agactgatca ccggcagact gtccgccctg aacgccttcg | 3660 |
| tggcccagac cctgaccaag tacaccgagt gcaggcctc cagaaagctg gcccagcaga | 3720 |
| aggtgaacga gtgcgtgaag tcccagagcc agagatacgg cttctgcggc ggcgacggcg | 3780 |
| agcacatctt ctccctggtg caggccgccc cacagggcct gctgttcctg cacaccgtgc | 3840 |
| tggtgccagg cgacttcatc gacgtgatcg ccatcgccgg cctgtgcgtg aacgacgaga | 3900 |
| tcgccctgac cctgagagag cccggcctgg tgctgttcac ccacgagctg cagaaccaca | 3960 |
| ccgccaccga gtatttcgtg agctccagac ggatgttcga gccaagaaag cccaccgtga | 4020 |
| gcgacttcgt gcagatcgag tcctgcgtgg tgacctacgt gaacctgacc agagaccagc | 4080 |
| tgccagacgt gatcccagac tacatcgacg tgaacaagac cctggacgag atcctggcct | 4140 |
| ccctgccaaa cagaaccggc cccagcctgc ccctggacgt gttcaacgcc acctacctga | 4200 |
| acctgaccgg cgagatcgcc gacctggagc agagaagcga gtccctgaga aacaccaccg | 4260 |
| aggagctgca gtccctgatc tacaacatca acaaccccct ggtggacctg agtggctga | 4320 |
| acagagtgga gacctacatc aagtggccat ggtgggtgtg gctgatcgtg ttcatcgtgc | 4380 |
| tgatcttcgt ggtgtccctg ctggtgttct gctgcatctc caccggctgc tgcggctgct | 4440 |
| gcggctgctg ctgcgcctgc ttcagcggct gctgtagagg accccggctc cagcccgctg | 4500 |
| aggtgtttga gaaagtgaga gtgcagtgat aaatattcaa gaccagtcct gcatcagtca | 4560 |
| acaattatca ttctaaactc attataaaaa acttaggaca caagagccta agtcctctcc | 4620 |
| taaaaaatga ctgaggtgta cgacttcgat cagtcttctt gggacaccaa gggcttattg | 4680 |
| gcccctattt tgcctaccac ttatcccgat ggtaggctca tacccaagt cagagtaata | 4740 |
| gatccaggac tcggcgatag gaaagatgaa tgcttcatgt atattttct actgggtata | 4800 |
| atagaagaca atgatggcct cggacccca attggaagaa catttggatt gctgccttg | 4860 |
| ggagttgggc gtactacagc cagacctgag gagttattga agaagccac cctgttggat | 4920 |
| attgtggtaa ggcgaactgc aggtgtcaag gaacaactgg tatttataa taacacccca | 4980 |
| ttgcacatct taactccgtg gaaaaaggtc cttacgagtg gaagtgtgtt cagtgcaaat | 5040 |
| caagtctgta acgcagtcaa tctaatacca ttagacatag cacaaagatt cagggtggta | 5100 |
| tatatgagca tcactcgact atcagacgat ggaagttaca gaattccccg cgg | 5153 |

<210> SEQ ID NO 15
<211> LENGTH: 1388
<212> TYPE: PRT
<213> ORGANISM: porcine epidemic diarrhea virus

<400> SEQUENCE: 15

Met Lys Ser Leu Thr Tyr Phe Trp Leu Phe Leu Pro Val Leu Ser Thr
1               5                   10                  15

```
Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
```

-continued

```
            435                 440                 445
Ala Leu Ile Glu Val Gln Gly Thr Ala Ile Gln Arg Ile Leu Tyr Cys
450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
                500                 505                 510

Val Asn Ile Thr Val Ser Ala Ser Phe Gly Gly His Ser Gly Ala Asn
            515                 520                 525

Leu Ile Ala Ser Asp Thr Thr Ile Asn Gly Phe Ser Ser Phe Cys Val
530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
            595                 600                 605

Phe Gly Ser Gly Val Lys Phe Thr Ser Leu Tyr Phe Gln Phe Thr Lys
610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
                660                 665                 670

Gly Val Tyr Tyr Thr Ser Asp Ser Gly Gln Leu Leu Ala Phe Lys Asn
            675                 680                 685

Val Thr Ser Gly Ala Val Tyr Ser Val Thr Pro Cys Ser Phe Ser Glu
            690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
                740                 745                 750

Asn Ile Gly Val Cys Lys Ser Gly Ser Ile Gly Tyr Val Pro Ser Gln
            755                 760                 765

Ser Gly Gln Val Lys Ile Ala Pro Thr Val Thr Gly Asn Ile Ser Ile
            770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
                820                 825                 830

Ile Glu Ser Ala Leu Gln Leu Ser Ala Arg Leu Glu Ser Val Glu Val
            835                 840                 845

Asn Ser Met Leu Thr Ile Ser Glu Glu Ala Leu Gln Leu Ala Thr Ile
850                 855                 860
```

-continued

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Gln Lys Arg Ser Phe
            885                 890                 895

Ile Glu Asp Ala Ala Phe Asn Lys Val Val Thr Asn Gly Leu Gly Thr
            900                 905                 910

Val Asp Glu Asp Tyr Lys Arg Cys Ser Asn Gly Arg Ser Val Ala Asp
            915                 920                 925

Leu Val Cys Ala Gln Tyr Tyr Ser Gly Val Met Val Leu Pro Gly Val
            930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Leu Pro Phe Ser Tyr
            965                 970                 975

Ala Val Gln Ala Arg Leu Asn Tyr Leu Ala Leu Gln Thr Asp Val Leu
            980                 985                 990

Gln Arg Asn Gln Gln Leu Leu Ala Glu Ser Phe Asn Ser Ala Ile Gly
            995                 1000                1005

Asn Ile Thr Ser Ala Phe Glu Ser Val Lys Glu Ala Ile Ser Gln
            1010                1015                1020

Thr Ser Lys Gly Leu Asn Thr Val Ala His Ala Leu Thr Lys Val
            1025                1030                1035

Gln Glu Val Val Asn Ser Gln Gly Ala Ala Leu Thr Gln Leu Thr
            1040                1045                1050

Val Gln Leu Gln His Asn Phe Gln Ala Ile Ser Ser Ser Ile Asp
            1055                1060                1065

Asp Ile Tyr Ser Arg Leu Asp Ile Leu Ser Ala Asp Val Gln Val
            1070                1075                1080

Asp Arg Leu Ile Thr Gly Arg Leu Ser Ala Leu Asn Ala Phe Val
            1085                1090                1095

Ala Gln Thr Leu Thr Lys Tyr Thr Glu Val Gln Ala Ser Arg Lys
            1100                1105                1110

Leu Ala Gln Gln Lys Val Asn Glu Cys Val Lys Ser Gln Ser Gln
            1115                1120                1125

Arg Tyr Gly Phe Cys Gly Gly Asp Gly Glu His Ile Phe Ser Leu
            1130                1135                1140

Val Gln Ala Ala Pro Gln Gly Leu Leu Phe Leu His Thr Val Leu
            1145                1150                1155

Val Pro Ser Asp Phe Val Asp Val Ile Ala Ile Ala Gly Leu Cys
            1160                1165                1170

Val Asn Asp Glu Ile Ala Leu Thr Leu Arg Glu Pro Gly Leu Val
            1175                1180                1185

Leu Phe Thr His Glu Leu Gln Asn His Thr Ala Thr Glu Tyr Phe
            1190                1195                1200

Val Ser Ser Arg Arg Met Phe Glu Pro Arg Lys Pro Thr Val Ser
            1205                1210                1215

Asp Phe Val Gln Ile Glu Ser Cys Val Val Thr Tyr Val Asn Leu
            1220                1225                1230

Thr Arg Asp Gln Leu Pro Asp Val Ile Pro Asp Tyr Ile Asp Val
            1235                1240                1245

Asn Lys Thr Leu Asp Glu Ile Leu Ala Ser Leu Pro Asn Arg Thr
            1250                1255                1260

```
Gly Pro Ser Leu Pro Leu Asp Val Phe Asn Ala Thr Tyr Leu Asn
    1265                1270                1275

Leu Thr Gly Glu Ile Ala Asp Leu Glu Gln Arg Ser Glu Ser Leu
    1280                1285                1290

Arg Asn Thr Thr Glu Glu Leu Gln Ser Leu Ile Tyr Asn Ile Asn
    1295                1300                1305

Asn Thr Leu Val Asp Leu Glu Trp Leu Asn Arg Val Glu Thr Tyr
    1310                1315                1320

Ile Lys Trp Pro Trp Trp Val Trp Leu Ile Ile Phe Ile Val Leu
    1325                1330                1335

Ile Phe Val Val Ser Leu Leu Val Phe Cys Cys Ile Ser Thr Gly
    1340                1345                1350

Cys Cys Gly Cys Cys Gly Cys Cys Ala Cys Phe Ser Gly Cys
    1355                1360                1365

Cys Arg Gly Pro Arg Leu Gln Pro Ala Glu Val Phe Glu Lys Val
    1370                1375                1380

Arg Val Gln Cys Gly
    1385

<210> SEQ ID NO 16
<211> LENGTH: 1386
<212> TYPE: PRT
<213> ORGANISM: porcine epidemic diarrhea virus

<400> SEQUENCE: 16

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
                    20                  25                  30

Arg Arg Phe Phe Ser Lys Phe Asn Val Gln Ala Pro Ala Val Val Val
                35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
                100                 105                 110

Thr Asn Gly Asn Thr Asn Ala Thr Ala Arg Leu Arg Ile Cys Gln Phe
            115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala Tyr Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
                180                 185                 190

Ala Thr Lys Cys Tyr Asn Ser Gly Gly Cys Ala Met Gln Tyr Val Tyr
            195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240
```

-continued

```
Val Phe Ala Thr Glu Pro Asn Gly His Ile Pro Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Gly Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Gly Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
        515                 520                 525

Leu Ile Ala Ser Asp Thr Thr Ile Asn Gly Phe Ser Ser Phe Cys Val
    530                 535                 540

Asp Thr Arg Gln Phe Thr Ile Ser Leu Phe Tyr Asn Val Thr Asn Ser
545                 550                 555                 560

Tyr Gly Tyr Val Ser Asn Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655
```

```
Phe Lys Gly Glu Gly Ile Ile Thr Leu Thr Asn Ser Ser Phe Leu Ala
            660                 665                 670

Gly Phe Tyr Tyr Thr Ser Asp Ser Gly Gln Leu Leu Ala Phe Lys Asn
        675                 680                 685

Val Thr Ser Gly Ala Val Tyr Ser Val Thr Pro Cys Ser Phe Ser Glu
    690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
            755                 760                 765

Ser Gly Gln Val Lys Ile Ala Pro Thr Val Thr Gly Asn Ile Ser Ile
770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
            820                 825                 830

Ile Glu Ser Ala Leu Gln Leu Ser Ala Arg Leu Glu Ser Val Glu Val
            835                 840                 845

Asn Ser Met Leu Thr Ile Ser Glu Glu Ala Leu Gln Leu Ala Thr Ile
    850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Leu Leu Phe Asn Lys Val Val Thr Asn Gly Leu Gly Thr
            900                 905                 910

Val Asp Glu Asp Tyr Lys Arg Cys Ser Asn Gly Arg Ser Val Ala Asp
    915                 920                 925

Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Ala Leu Pro Phe Ser Tyr
                965                 970                 975

Ala Val Gln Ala Arg Leu Asn Tyr Leu Ala Leu Gln Thr Asp Val Leu
            980                 985                 990

Gln Arg Asn Gln Gln Leu Leu Ala Glu Ser Phe Asn Ser Ala Ile Gly
            995                 1000                1005

Asn Ile Thr Ser Ala Phe Glu Ser Val Lys Glu Ala Ile Ser Gln
        1010                1015                1020

Thr Ser Lys Gly Leu Asn Thr Val Ala His Ala Leu Thr Lys Val
        1025                1030                1035

Gln Glu Val Val Asn Ser Gln Gly Ala Ala Leu Thr Gln Leu Thr
        1040                1045                1050

Val Gln Leu Gln His Asn Phe Gln Ala Ile Ser Ser Ser Ile Asp
        1055                1060                1065

Asp Ile Tyr Ser Arg Leu Asp Ile Leu Ser Ala Asp Val Gln Val
```

```
            1070                1075                1080

Asp Arg Leu Ile Thr Gly Arg Leu Ser Ala Leu Asn Ala Phe Val
        1085                1090                1095

Ala Gln Thr Leu Thr Lys Tyr Thr Glu Val Gln Ala Ser Arg Lys
        1100                1105                1110

Leu Ala Gln Gln Lys Val Asn Glu Cys Val Lys Ser Gln Ser Gln
        1115                1120                1125

Arg Tyr Gly Phe Cys Gly Gly Asp Gly Glu His Ile Phe Ser Leu
        1130                1135                1140

Val Gln Ala Ala Pro Gln Gly Leu Leu Phe Leu His Thr Val Leu
        1145                1150                1155

Val Pro Gly Asp Phe Val Asp Val Ile Ala Ile Ala Gly Leu Cys
        1160                1165                1170

Val Asn Asp Glu Ile Ala Leu Thr Leu Arg Glu Pro Gly Leu Val
        1175                1180                1185

Leu Phe Thr His Glu Leu Gln Asn His Thr Ala Thr Glu Tyr Phe
        1190                1195                1200

Val Ser Ser Arg Arg Met Phe Glu Pro Arg Lys Pro Thr Val Ser
        1205                1210                1215

Asp Phe Val Gln Ile Glu Ser Cys Val Val Thr Tyr Val Asn Leu
        1220                1225                1230

Thr Arg Asp Gln Leu Pro Asp Val Ile Pro Asp Tyr Ile Asp Val
        1235                1240                1245

Asn Lys Thr Leu Asp Glu Ile Leu Ala Ser Leu Pro Asn Arg Thr
        1250                1255                1260

Gly Pro Ser Leu Pro Leu Asp Val Phe Asn Ala Thr Tyr Leu Asn
        1265                1270                1275

Leu Thr Gly Glu Ile Ala Asp Leu Glu Gln Arg Ser Glu Ser Leu
        1280                1285                1290

Arg Asn Thr Thr Glu Glu Leu Gln Ser Leu Ile Tyr Asn Ile Asn
        1295                1300                1305

Asn Thr Leu Val Asp Leu Glu Trp Leu Asn Arg Val Glu Thr Tyr
        1310                1315                1320

Ile Lys Trp Pro Trp Trp Val Trp Leu Ile Ile Phe Ile Val Leu
        1325                1330                1335

Ile Phe Val Val Ser Leu Leu Val Phe Cys Cys Ile Ser Thr Gly
        1340                1345                1350

Cys Cys Gly Cys Cys Gly Cys Cys Ala Cys Phe Ser Gly Cys
        1355                1360                1365

Cys Arg Gly Pro Arg Leu Gln Pro Tyr Glu Ala Phe Glu Lys Val
        1370                1375                1380

His Val Gln
        1385

<210> SEQ ID NO 17
<211> LENGTH: 1386
<212> TYPE: PRT
<213> ORGANISM: porcine epidemic diarrhea virus

<400> SEQUENCE: 17

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30
```

Arg Arg Phe Phe Ser Lys Phe Asn Val Gln Ala Pro Ala Val Val
         35                  40                  45

Leu Gly Gly Tyr Leu Pro Ile Gly Glu Asn Gln Gly Val Asn Ser Thr
 50                  55                  60

Trp Tyr Cys Ala Gly Gln His Pro Thr Ala Ser Gly Val His Gly Ile
 65                  70                  75                  80

Phe Val Ser His Ile Arg Gly Gly His Gly Phe Glu Ile Gly Ile Ser
                 85                  90                  95

Gln Glu Pro Phe Asp Pro Ser Gly Tyr Gln Leu Tyr Leu His Lys Ala
                100                 105                 110

Thr Asn Gly Asn Thr Asn Ala Thr Ala Arg Leu Arg Ile Cys Gln Phe
            115                 120                 125

Pro Ser Ile Lys Thr Leu Gly Pro Thr Ala Asn Asn Asp Val Thr Thr
            130                 135                 140

Gly Arg Asn Cys Leu Phe Asn Lys Ala Ile Pro Ala Tyr Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Lys Asn Asp Trp Ser Arg Val
            180                 185                 190

Ala Thr Lys Cys Tyr Asn Ser Gly Gly Cys Ala Met Gln Tyr Val Tyr
            195                 200                 205

Glu Pro Thr Tyr Tyr Met Leu Asn Val Thr Ser Ala Gly Glu Asp Gly
            210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
            275                 280                 285

Lys Ile Tyr Gly Leu Gly Gln Phe Phe Ser Phe Asn Gln Thr Ile Asp
            290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Gly Pro His Leu Ala Thr Phe Ala Ile Pro Leu Gly Ala Thr Gln
            355                 360                 365

Val Pro Tyr Tyr Cys Phe Leu Lys Val Asp Thr Tyr Asn Ser Thr Val
            370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Gly Asp Val Ser Gly Phe Trp Thr Ile Ala Ser Thr Asn Phe Val Asp
            435                 440                 445

Ala Leu Ile Glu Val Gln Gly Thr Ala Ile Gln Arg Ile Leu Tyr Cys

```
        450             455             460
Asp Asp Pro Val Ser Gln Leu Lys Cys Ser Gln Val Ala Phe Asp Leu
465                 470              475             480

Asp Asp Gly Phe Tyr Pro Ile Ser Ser Arg Asn Leu Leu Ser His Glu
                485             490              495

Gln Pro Ile Ser Phe Val Thr Leu Pro Ser Phe Asn Asp His Ser Phe
            500             505             510

Val Asn Ile Thr Val Ser Ala Ser Phe Gly Gly His Ser Gly Ala Asn
        515             520             525

Leu Ile Ala Ser Asp Thr Thr Ile Asn Gly Phe Ser Ser Phe Cys Val
530             535             540

Asp Thr Arg Gln Phe Thr Ile Ser Leu Phe Tyr Asn Val Thr Asn Ser
545             550             555             560

Tyr Gly Tyr Val Ser Asn Ser Gln Asp Ser Asn Cys Pro Phe Thr Leu
                565             570             575

Gln Ser Val Asn Asp Tyr Leu Ser Phe Ser Lys Phe Cys Val Ser Thr
            580             585             590

Ser Leu Leu Ala Ser Ala Cys Thr Ile Asp Leu Phe Gly Tyr Pro Glu
        595             600             605

Phe Gly Ser Gly Val Lys Phe Thr Ser Leu Tyr Phe Gln Phe Thr Lys
    610             615             620

Gly Glu Leu Ile Thr Gly Thr Pro Lys Pro Leu Glu Gly Val Thr Asp
625             630             635             640

Val Ser Phe Met Thr Leu Asp Val Cys Thr Lys Tyr Thr Ile Tyr Gly
                645             650             655

Phe Lys Gly Glu Gly Ile Ile Thr Leu Thr Asn Ser Ser Phe Leu Ala
            660             665             670

Gly Phe Tyr Tyr Thr Ser Asp Ser Gly Gln Leu Leu Ala Phe Lys Asn
            675             680             685

Val Thr Ser Gly Ala Val Tyr Ser Val Thr Pro Cys Ser Phe Ser Glu
        690             695             700

Gln Ala Ala Tyr Val Asp Asp Ile Val Gly Val Ile Ser Ser Leu
705             710             715             720

Ser Ser Ser Thr Phe Asn Ser Thr Arg Glu Leu Pro Gly Phe Phe Tyr
            725             730             735

His Ser Asn Asp Gly Ser Asn Cys Thr Glu Pro Val Leu Val Tyr Ser
            740             745             750

Asn Ile Gly Val Cys Lys Ser Gly Ser Ile Gly Tyr Val Pro Ser Gln
            755             760             765

Ser Gly Gln Val Lys Ile Ala Pro Thr Val Thr Gly Asn Ile Ser Ile
            770             775             780

Pro Thr Asn Phe Ser Met Ser Ile Arg Thr Glu Tyr Leu Gln Leu Tyr
785             790             795             800

Asn Thr Pro Val Ser Val Asp Cys Ala Thr Tyr Val Cys Asn Gly Asn
                805             810             815

Ser Arg Cys Lys Gln Leu Leu Thr Gln Tyr Thr Ala Ala Cys Lys Thr
            820             825             830

Ile Glu Ser Ala Leu Gln Leu Ser Ala Arg Leu Glu Ser Val Glu Val
            835             840             845

Asn Ser Met Leu Thr Ile Ser Glu Glu Ala Leu Gln Leu Ala Thr Ile
        850             855             860

Ser Ser Phe Asn Gly Asp Gly Tyr Asn Phe Thr Asn Val Leu Gly Val
865             870             875             880
```

-continued

Ser Val Tyr Asp Pro Ala Ser Gly Arg Val Val Gln Lys Arg Ser Phe
            885                 890                 895

Ile Glu Asp Ala Ala Phe Asn Lys Val Val Thr Asn Gly Leu Gly Thr
    900                 905                 910

Val Asp Glu Asp Tyr Lys Arg Cys Ser Asn Gly Arg Ser Val Ala Asp
        915                 920                 925

Leu Val Cys Ala Gln Tyr Tyr Ser Gly Val Met Val Leu Pro Gly Val
    930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Leu Pro Phe Ser Tyr
                965                 970                 975

Ala Val Gln Ala Arg Leu Asn Tyr Leu Ala Leu Gln Thr Asp Val Leu
        980                 985                 990

Gln Arg Asn Gln Gln Leu Leu Ala Glu Ser Phe Asn Ser Ala Ile Gly
            995                 1000                1005

Asn Ile Thr Ser Ala Phe Glu Ser Val Lys Glu Ala Ile Ser Gln
        1010                1015                1020

Thr Ser Lys Gly Leu Asn Thr Val Ala His Ala Leu Thr Lys Val
        1025                1030                1035

Gln Glu Val Val Asn Ser Gln Gly Ala Ala Leu Thr Gln Leu Thr
        1040                1045                1050

Val Gln Leu Gln His Asn Phe Gln Ala Ile Ser Ser Ser Ile Asp
        1055                1060                1065

Asp Ile Tyr Ser Arg Leu Asp Ile Leu Ser Ala Asp Val Gln Val
        1070                1075                1080

Asp Arg Leu Ile Thr Gly Arg Leu Ser Ala Leu Asn Ala Phe Val
        1085                1090                1095

Ala Gln Thr Leu Thr Lys Tyr Thr Glu Val Gln Ala Ser Arg Lys
        1100                1105                1110

Leu Ala Gln Gln Lys Val Asn Glu Cys Val Lys Ser Gln Ser Gln
        1115                1120                1125

Arg Tyr Gly Phe Cys Gly Gly Asp Gly Glu His Ile Phe Ser Leu
        1130                1135                1140

Val Gln Ala Ala Pro Gln Gly Leu Leu Phe Leu His Thr Val Leu
        1145                1150                1155

Val Pro Gly Asp Phe Val Asp Val Ile Ala Ile Ala Gly Leu Cys
        1160                1165                1170

Val Asn Asp Glu Ile Ala Leu Thr Leu Arg Glu Pro Gly Leu Val
        1175                1180                1185

Leu Phe Thr His Glu Leu Gln Asn His Thr Ala Thr Glu Tyr Phe
        1190                1195                1200

Val Ser Ser Arg Arg Met Phe Glu Pro Arg Lys Pro Thr Val Ser
        1205                1210                1215

Asp Phe Val Gln Ile Glu Ser Cys Val Val Thr Tyr Val Asn Leu
        1220                1225                1230

Thr Arg Asp Gln Leu Pro Asp Val Ile Pro Asp Tyr Ile Asp Val
        1235                1240                1245

Asn Lys Thr Leu Asp Glu Ile Leu Ala Ser Leu Pro Asn Arg Thr
        1250                1255                1260

Gly Pro Ser Leu Pro Leu Asp Val Phe Asn Ala Thr Tyr Leu Asn
        1265                1270                1275

```
Leu Thr Gly Glu Ile Ala Asp Leu Glu Gln Arg Ser Glu Ser Leu
    1280                1285                1290

Arg Asn Thr Thr Glu Glu Leu Gln Ser Leu Ile Tyr Asn Ile Asn
    1295                1300                1305

Asn Thr Leu Val Asp Leu Glu Trp Leu Asn Arg Val Glu Thr Tyr
    1310                1315                1320

Ile Lys Trp Pro Trp Trp Val Trp Leu Ile Ile Phe Ile Val Leu
    1325                1330                1335

Ile Phe Val Val Ser Leu Leu Val Phe Cys Cys Ile Ser Thr Gly
    1340                1345                1350

Cys Cys Gly Cys Cys Gly Cys Cys Ala Cys Phe Ser Gly Cys
    1355                1360                1365

Cys Arg Gly Pro Arg Leu Gln Pro Ala Glu Ala Phe Glu Lys Val
    1370                1375                1380

Arg Val Gln
    1385

<210> SEQ ID NO 18
<211> LENGTH: 29
<212> TYPE: DNA
<213> ORGANISM: Artificial Sequence
<220> FEATURE:
<223> OTHER INFORMATION: probe sequence

<400> SEQUENCE: 18
acagagcctg tgttggtgta tagtaacat                                    29

<210> SEQ ID NO 19
<211> LENGTH: 23
<212> TYPE: DNA
<213> ORGANISM: Artificial Sequence
<220> FEATURE:
<223> OTHER INFORMATION: primer sequence

<400> SEQUENCE: 19
tatagtgggt gttatttcta gtt                                          23

<210> SEQ ID NO 20
<211> LENGTH: 21
<212> TYPE: DNA
<213> ORGANISM: Artificial Sequence
<220> FEATURE:
<223> OTHER INFORMATION: primer sequence

<400> SEQUENCE: 20
gccaatactg ccagatttac a                                            21

<210> SEQ ID NO 21
<211> LENGTH: 170
<212> TYPE: DNA
<213> ORGANISM: Artificial Sequence
<220> FEATURE:
<223> OTHER INFORMATION: ultramer sequence

<400> SEQUENCE: 21
tgatgatata gtgggtgtta tttctagttt gtctagctcc acttttaaca gtactaggga   60
gttgcctggt ttcttctacc attctaatga tggctctaat tgtacagagc ctgtgttggt   120
gtatagtaac ataggtgttt gtaaatctgg cagtattggc tatgtcccat             170
```